United States Patent
Lei

(10) Patent No.: US 11,541,072 B2
(45) Date of Patent: Jan. 3, 2023

(54) AAV-CRISPR/CAS9 GENOME EDITING OF VEGFR2 FOR TREATING OCULAR DISEASES

(71) Applicant: Massachusetts Eye and Ear Infirmary, Boston, MA (US)

(72) Inventor: Hetian Lei, West Roxbury, MA (US)

(73) Assignee: Massachusetts Eye and Ear Infirmary, Boston, MA (US)

(*) Notice: Subject to any disclaimer, the term of this patent is extended or adjusted under 35 U.S.C. 154(b) by 48 days.

Patent file contains an affidavit/declaration under 37 CFR 1.130(b).

(21) Appl. No.: 16/621,889

(22) PCT Filed: Jun. 27, 2018

(86) PCT No.: PCT/US2018/039699
§ 371 (c)(1),
(2) Date: Dec. 12, 2019

(87) PCT Pub. No.: WO2019/005926
PCT Pub. Date: Jan. 3, 2019

(65) Prior Publication Data
US 2020/0113926 A1  Apr. 16, 2020

Related U.S. Application Data

(60) Provisional application No. 62/525,545, filed on Jun. 27, 2017.

(51) Int. Cl.
| | | |
|---|---|---|
| C12N 15/11 | (2006.01) | |
| A61K 31/7105 | (2006.01) | |
| A61K 9/00 | (2006.01) | |
| A61K 35/761 | (2015.01) | |
| A61K 38/46 | (2006.01) | |
| A61K 48/00 | (2006.01) | |
| C12N 15/113 | (2010.01) | |
| C12N 15/86 | (2006.01) | |
| C12N 15/90 | (2006.01) | |
| A61K 45/06 | (2006.01) | |

(52) U.S. Cl.
CPC ........ *A61K 31/7105* (2013.01); *A61K 9/0048* (2013.01); *A61K 35/761* (2013.01); *A61K 38/465* (2013.01); *A61K 48/005* (2013.01); *A61K 48/0075* (2013.01); *C12N 15/1138* (2013.01); *C12N 15/86* (2013.01); *C12N 15/907* (2013.01); *A61K 45/06* (2013.01); *C12N 2320/32* (2013.01); *C12N 2750/14143* (2013.01)

(58) Field of Classification Search
CPC ................................................ C12N 2310/20
See application file for complete search history.

(56) References Cited

U.S. PATENT DOCUMENTS

| 2009/0247604 A1 | 10/2009 | Tang et al. |
| 2016/0145611 A1* | 5/2016 | Suhy .......................... A61P 9/00 514/44 A |
| 2016/0153006 A1 | 6/2016 | Zhang et al. |
| 2016/0237455 A1 | 8/2016 | Glucksmann et al. |
| 2016/0346359 A1 | 12/2016 | Buchlis et al. |

FOREIGN PATENT DOCUMENTS

| WO | WO 2008/109368 | 9/2008 |
| WO | WO 2015/048577 | 4/2015 |

OTHER PUBLICATIONS

Huang et al., Inactivation of VEGFR2 using CRISPR/Cas9 provides superior inhibition to the anti-VEGF drugs, Investigative Ophthalmology & Visual Science, vol. 57, abstract No. 5024, submitted for the 2016 ARVO Annual Meeting, held in Seattle, Washington, May 1-5, 2016. (Year: 2016).*
Wu et al., Application of CRISPR-Cas9 in eye disease, Experimental Eye Research, vol. 161, pp. 116-123. (Year: 2017).*
Bainbridge et al., "Effect of gene therapy on visual function in Leber's congenital amaurosis," N Engl J Med, May 22, 2008, 351(21):2231-2239.
Bergers et al., "Matrix metalloproteinase-9 triggers the angiogenic switch during carcinogenesis," Nat Cell Biol., Oct. 2000, 2(10):737-744.
Chakravarthy et al., "Alternative treatments to inhibit VEGF in age-related choroidal neovascularisation: 2-year findings of the IVAN randomized controlled trial," Lancet, Oct. 12, 2013, 382:1258-1267.
Chitranshi et al., "Exploring the Molecular Interactions of 7,8-Dihydroxyflavone and Its Derivatives with TrkB and VEGFR2 Proteins," Int. J. Mol. Sci., 2015, 16(9):21087-21108.
Connor et al., "Quantification of oxygen-induced retinopathy in the mouse: a model of vessel loss, vessel regrowth and pathological angiogenesis," Nat Protoc, 2009, 4(11):1565-1573.
Cox et al., "Therapeutic genome editing: prospects and challenges," Nat Med, Feb. 2015, 21(2):121-131.
Dai et al., "Identification of synthetic endothelial cell-specific promoters by use of a high-throughput screen," Journal of Virology, Jun. 2004, 78(12):6209-6221.
Deyle et al., "Adeno-associated virus vector integration," Curr Opin Mol Ther., Aug. 2009, 11(4):442-447.

(Continued)

*Primary Examiner* — Dana H Shin
(74) *Attorney, Agent, or Firm* — Fish & Richardson P.C.

(57) ABSTRACT

Editing of VEGFR2 abrogated angiogenesis in two mouse models of oxygen-induced retinopathy (OIR) and laser-induced choroid neovascularization (CNV). Provided are compositions, e.g., Adeno-Associated Virus (AAV) Vectors comprising sequences encoding CRISPR/Cas9 proteins and guide RNA, and methods of use thereof for editing of Vascular endothelial growth factor receptor 2 (VEGFR2) gene to treat ocular disease associated with pathological angiogenesis, e.g., neovascular age-related macular degeneration (AMD), proliferative diabetic retinopathy (PDR) and retinopathy of prematurity (ROP).

8 Claims, 13 Drawing Sheets

Specification includes a Sequence Listing.

(56) References Cited

OTHER PUBLICATIONS

Duan et al., "The Clustered, Regularly Interspaced, Short Palindromic Repeats-associated Endonuclease 9 (CRISPR/Cas9)-created MDM2 T309G Mutation Enhances Vitreous-induced Expression of MDM2 and Proliferation and Survival of Cells," The Journal of Biological Chemistry, Jul. 29, 2016, 291(31):16339-16347.

Ellis et al., "A survey of ex vivo/in vitro transduction efficiency of mammalian primary cells and cell lines with Nine natural adeno-associated virus (AAV1-9) and one engineered adeno-associated virus serotype," Virology Journal, 2013, 10(74):1-10.

Ferris et al., "Age-related macular degeneration and blindness due to neovascular maculopathy," Archives of Ophthalmology, 1984, 102(11):1640-1642.

Folkman, "Angiogenesis in cancer, vascular, rheumatoid and other disease," Nature Medicine, 1995, 1(1):27-30.

Fraser-Bell et al., "Update on treatments for diabetic macular edema," Current Opinion in Ophthalmology, 2008, 19(3):185-189.

Gaudet et al., "Efficacy and long-term safety of alipogene tiparvovec (AAV1-LPLS447X) gene therapy for lipoprotein lipase deficiency: an open-label trial," Gene Therapy, 2013, 20:361-369.

Gaudet et al., "Gene therapy for lipoprotein lipase deficiency," Current Opinion in Lipidology, 2012, 23(4):310-320.

Giani et al., "In vivo evaluation of laser-induced choroidal neovascularization using spectral-domain optical coherence tomography," Invest Ophthalmol Vis Sci., May 2011, 52:3880-3887.

Giraudo et al., "An amino-bisphosphonate targets MMP-9-expressing macrophages and angiogenesis to impair cervical carcinogenesis," J Clin Invest., 2004, 114(5):623-633.

Gragoudas et al., "Pegaptanib for neovascular age-related macular degeneration," N Engl J Med, Dec. 30, 2004, 351(27):2805-2816.

Grieger et al., "Production and characterization of adeno-associated viral vectors," Nat Protoc, 2006, 1(3):1412-1428.

Hauswirth et al., "Treatment of Leber congenital amaurosis due to RPE65 mutations by ocular subretinal injection of adeno-associated virus gene vector: short-term results of a phase I trial," Human Gener Therapy, Oct. 2008, 19:979-990.

Holmes et al., "Vascular endothelial growth factor receptor-2: structure, function, intracellular signaling and therapeutic inhibition," Cellular Signaling, 2007, 19:2003-2012.

Huang et al., "Editing VEGFR2 blocks VEGF-induced activation of akt and tube formation, Biochemistiy and Molecular Biology," Feb. 2017, 52(2):1228-1236.

Jessup et al., "Calcium Upregulation by Percutaneous Administration of Gene Therapy in Cardiac Disease (CUPID): a phase 2 trial of intracoronary gene therapy of sarcoplasmic reticulum Ca2+-ATPase in patients with advanced heart failure," Circulation, Jul. 2011, 124(9):304-313.

Jinek et al., "A programmable dual-RNA-guided DNA endonuclease in adaptive bacterial immunity," Science, 17 Science 2012, 337(6096):816-821.

Kawamoto et al., "Therapeutic potential of ex vivo expanded endothelial progenitor cells for myocardial ischemia," Circulation, Feb. 6, 2001, 103(5):634-637.

Lambert et al., "Laser-induced choroidal neovascularization model to study age-related macular degeneration in mice," Nat Protcol., 2013, 8(11):2197-2211.

Lei et al., "Heat shock protein 90alpha-dependent translocation of annexin II to the surface of endothelial cells modulates plasmin activity in the diabetic rat aorta," Circulation Research, Apr. 16, 2004, 94(7), 902-909.

Lei et al., "RasGAP promotes autophagy and thereby suppresses platelet-derived growth factor receptor-mediated signaling events, cellular responses, and pathology," Molecular and Cellular Biology, May 2015, 35(10):1673-1685.

Maguire et al., "Safety and efficacy of gene transfer for Leber's congenital amaurosis," N Engl J Med, May 22, 2008, 358(21):2240-2248.

Mintz-Hittner et al., "Efficacy of intravitreal bevacizumab for stage 3+ retinopathy of prematurity," N Engl J Med, Feb. 17, 2011, 364(7):603-615.

Muller et al., "Vascular endothelial growth factor: crystal structure and functional mapping of the kinase domain receptor binding site," Proc. Natl. Acad. Sci., Jul. 1997, 94:7192-7197.

PCT International Preliminary Search Report on Patentability in International Appln No. PCT/US/2018/369699, dated Dec. 31, 2019, 10 pages.

PCT International Search Report and Written Opinion in International Applin No. PCT/US2018/39699, dated Sep. 25, 2018, 11 pages.

Pillay et al., "An essential receptor for adeno-associated virus infection," Nature, Feb. 4, 2016, 530(7588):108-112.

Ruan et al., "Axl is essential for VEGF-A-dependent activation of PI3K/Akt. EMBO J 31," The EMBO Journal, 2012 31:1692-1703.

Saint-Geniez et al., "PGC-1alpha regulates normal and pathological angiogenesis in the retina," The American Journal of Pathology, Jan. 2013, 182(1):255-265.

Senger et al., "Tumor cells secrete a vascular permeability factor that promotes accumulation of ascites fluid," Science, 219(4587):983-985.

Shima et al., "Hypoxic induction of endothelial cell growth factors in retinal cells: identification and characterization of vascular endothelial growth factor (VEGF) as the mitogen," Molecular Medicine, Jan. 1995, 1(2): 182-193.

Stahl et al., "The mouse retina as an angiogenesis model," Invest Ophthalmol & Vis Sci, Jun. 2010, 52(6):2813-2826.

Suzuki et al., "Predictive factors for non-response to intravitreal ranibizumab treatment in age-related macular degeneration," Br J Ophthalmol, 2014, 98:1186-1191.

Sweich et al., "In vivo interrogation of gene function in the mammalian brain using CRISPR-Cas9," Nat Biotechnol, Jan. 2015, 33(1):102-106.

Tabebordbar et al., "In vivo gene editing in dystrophic mouse muscle and muscle stem cells," Science, Jan. 22, 216, 351(6271):407-411.

Takeda et al., "CCR3 is a therapeutic and diagnostic target for neovascular agerelated macular degeneration," Nature, Jul. 9, 2009, 460(7252):225-230.

Wang et al., "The role of anti-inflammatory agents in age-related macular degeneration (AMD) treatment, Eye," 2011, 25:127-139.

Williams et al., "Epidemiology of diabetic retinopathy and macular oedema: a systematic review," Eye, 2004, 18:963-983.

Yanai et al., "Cytochrome P450-generated metabolites derived from ω-3 fatty acids attenuate neovascularization," Proc Natl Acad Sci, Jul. 1, 2014, 111(26):9603-9608.

Zhang et al., "CRISPR-Cas9: Prospects and Challenges. Human gene therapy 26," Human Gene Therapy, 2015, 26(7):409-410.

* cited by examiner

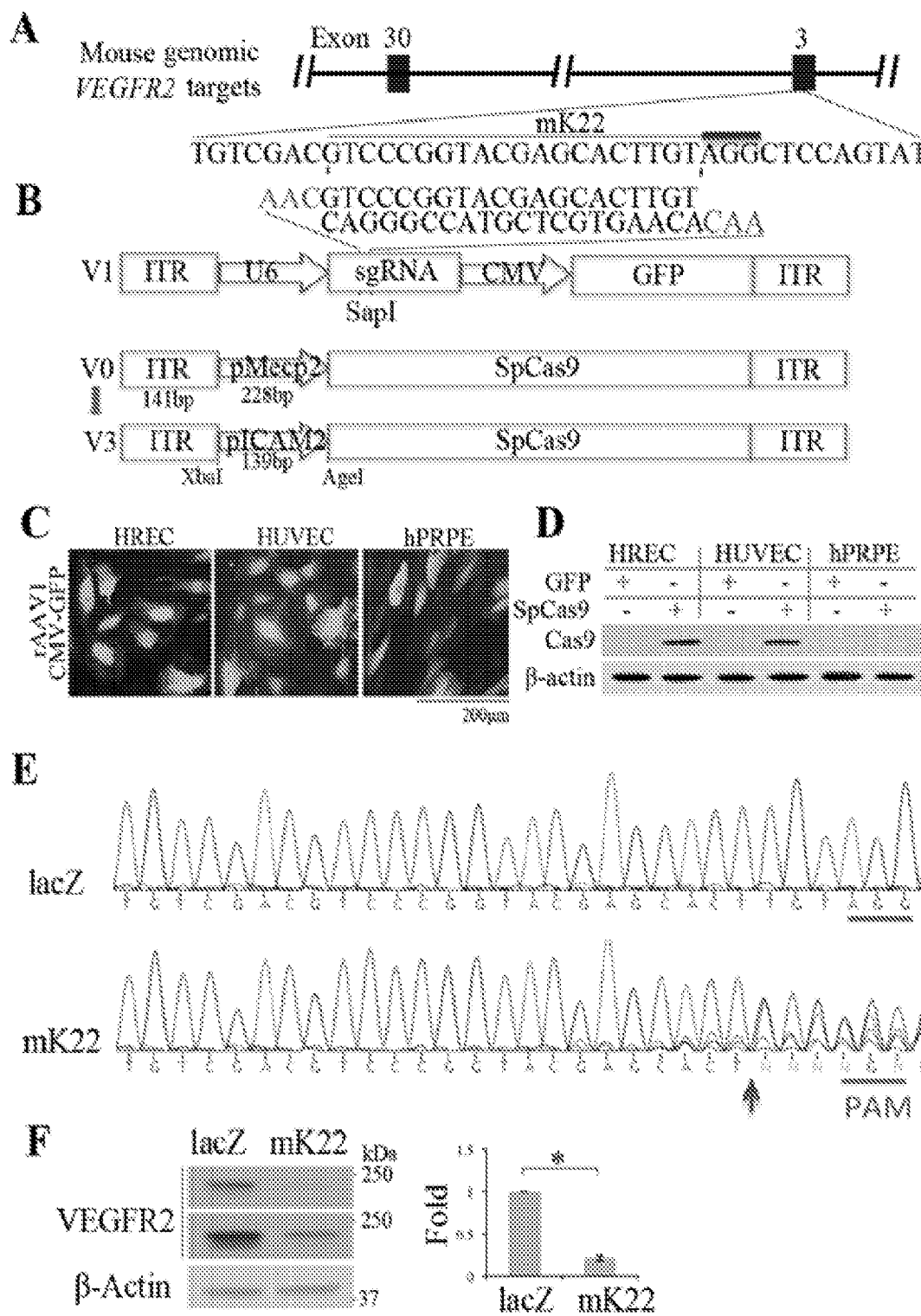
FIGs. 1A-F

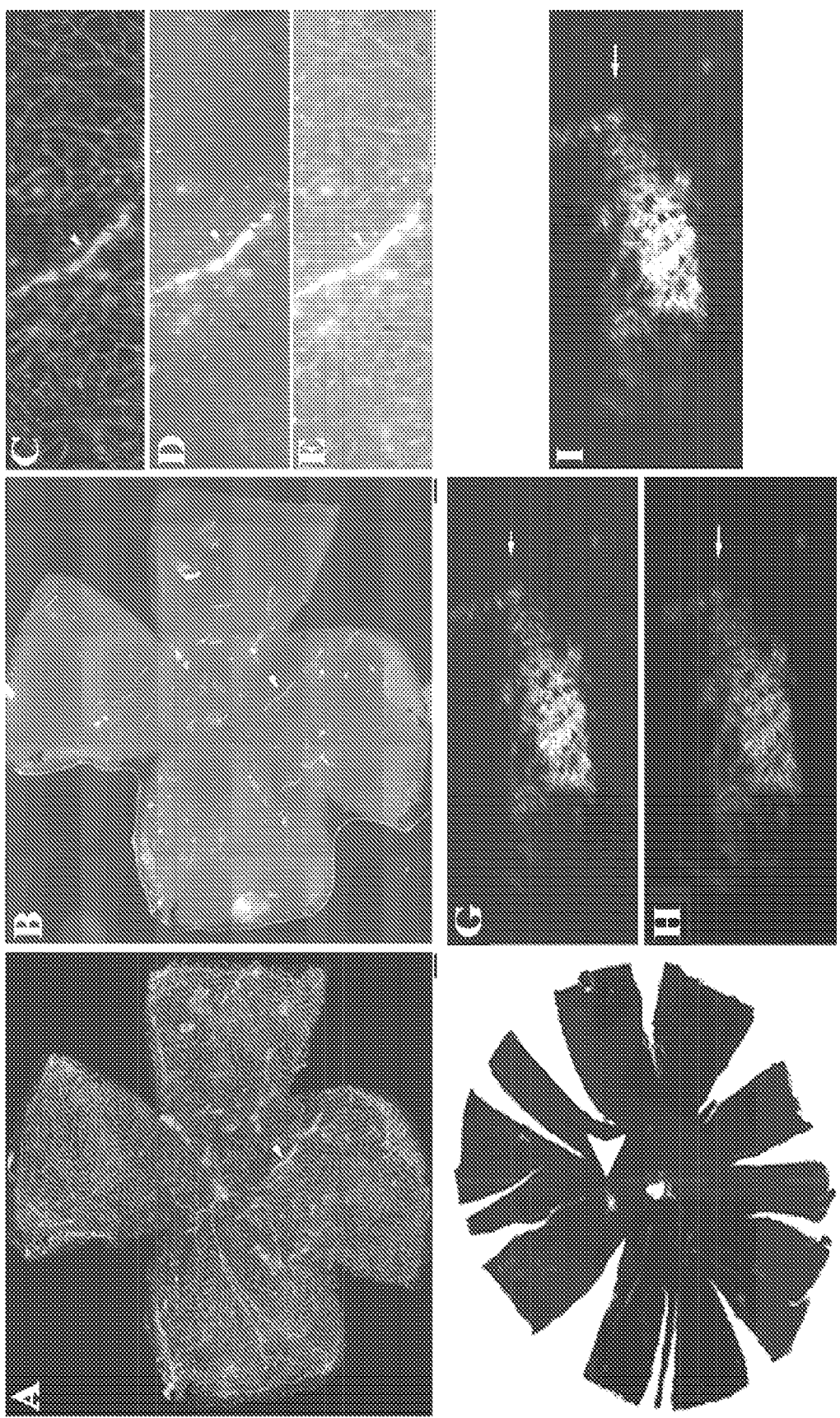
FIGs. 2A-I

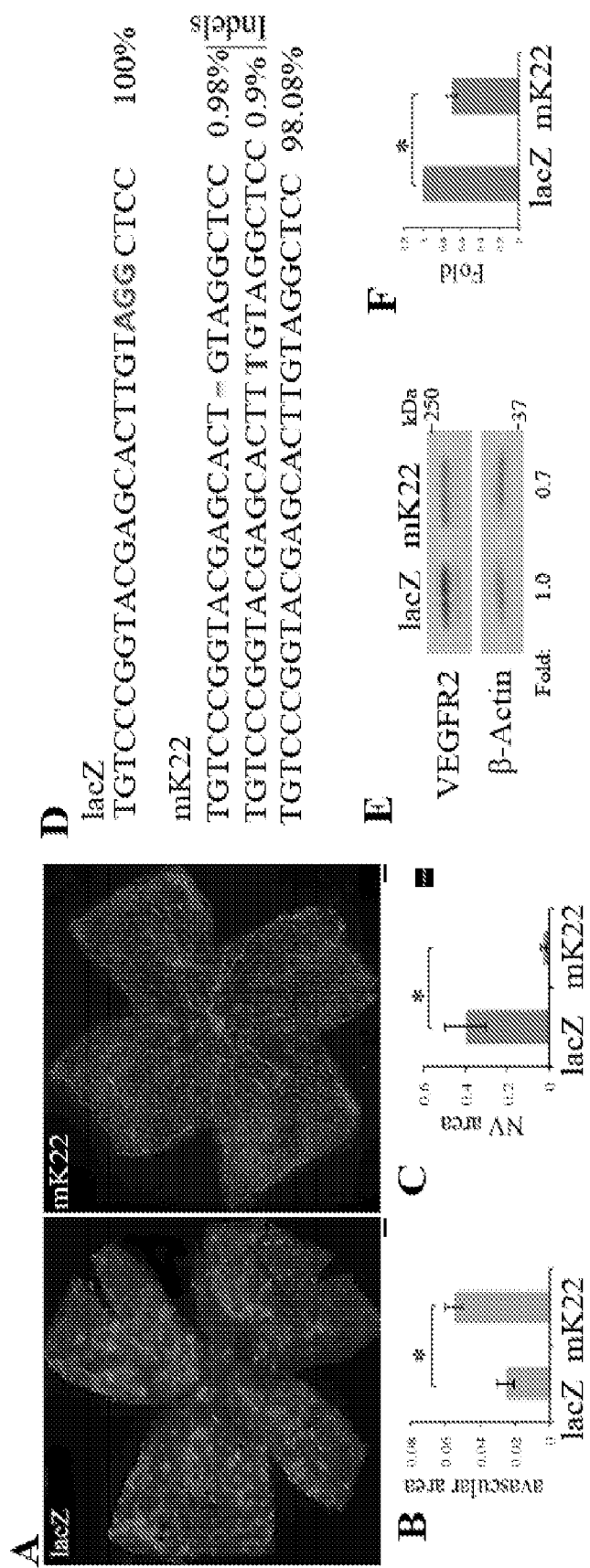
FIGs. 3A-F

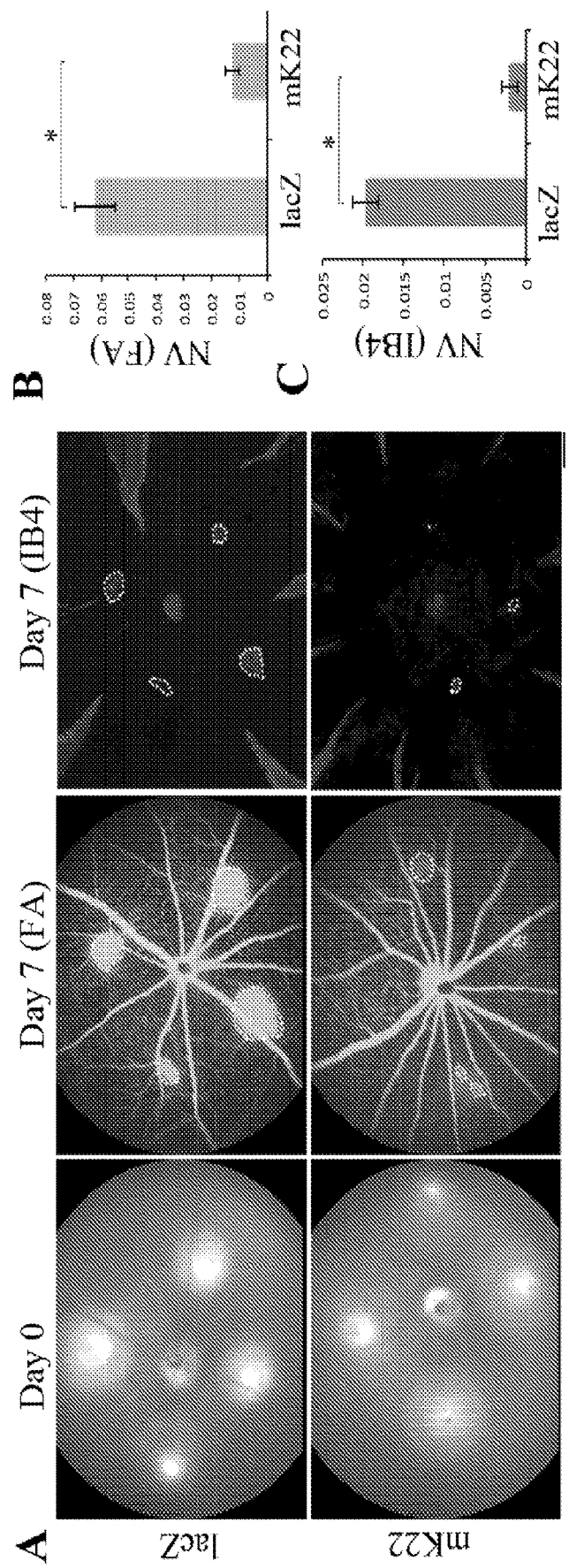
FIGs. 4A-C

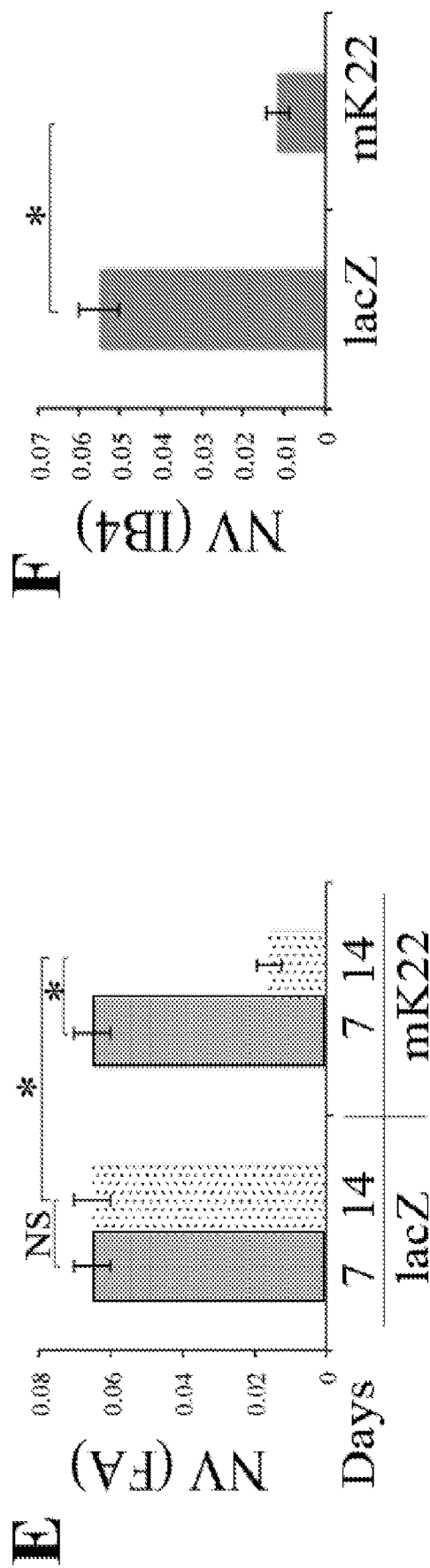
FIGs. 4E-F

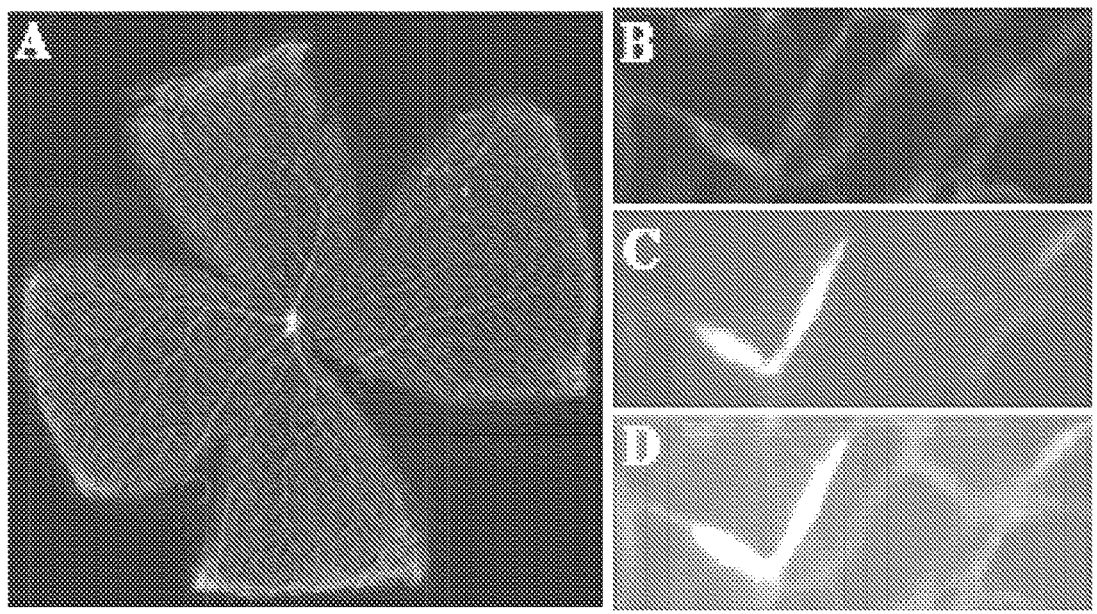
FIGs. 7A-D
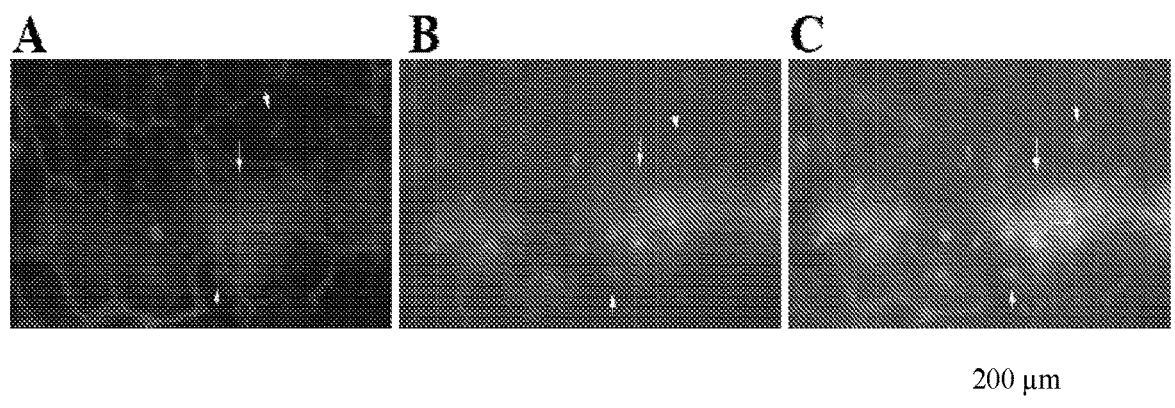
200 μm
FIGs. 8A-C

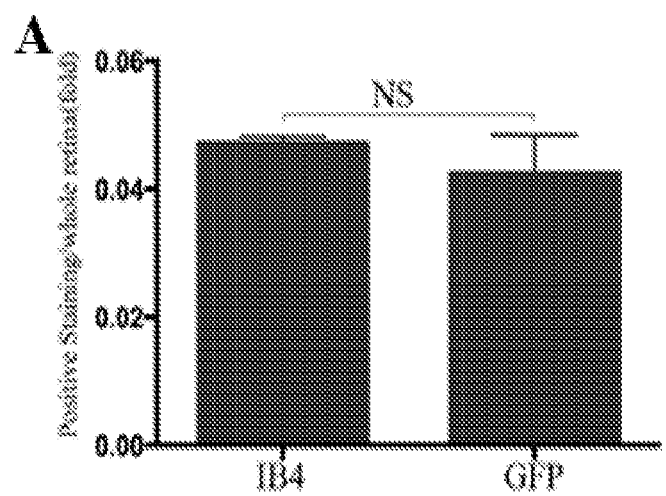
FIG. 9A
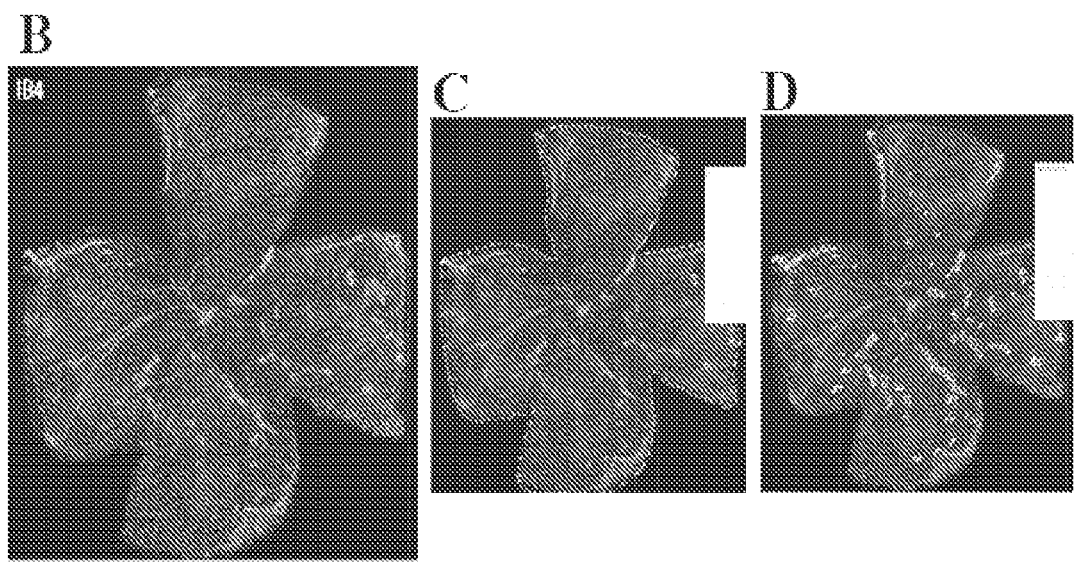
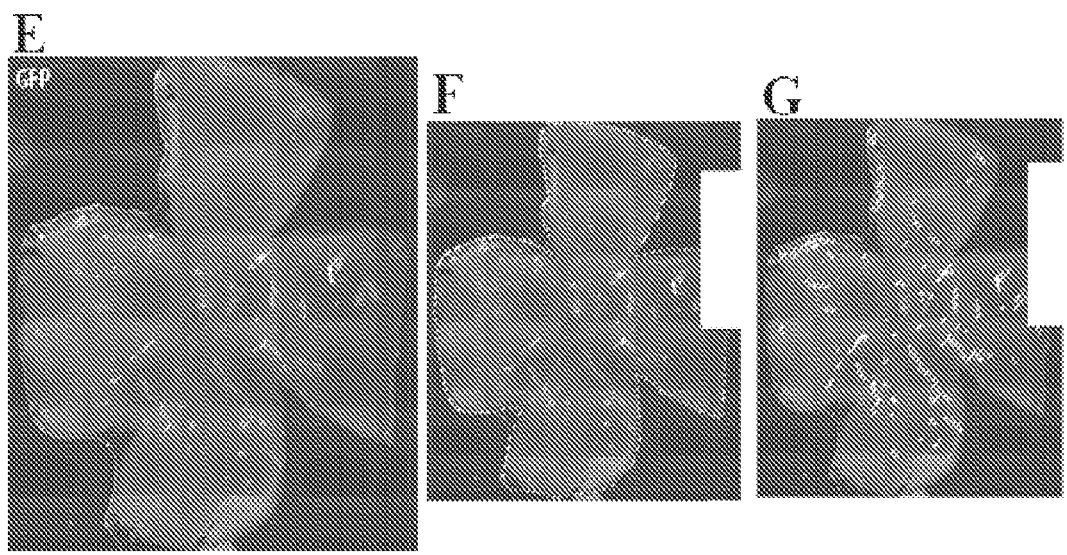
FIGs. 9B-G

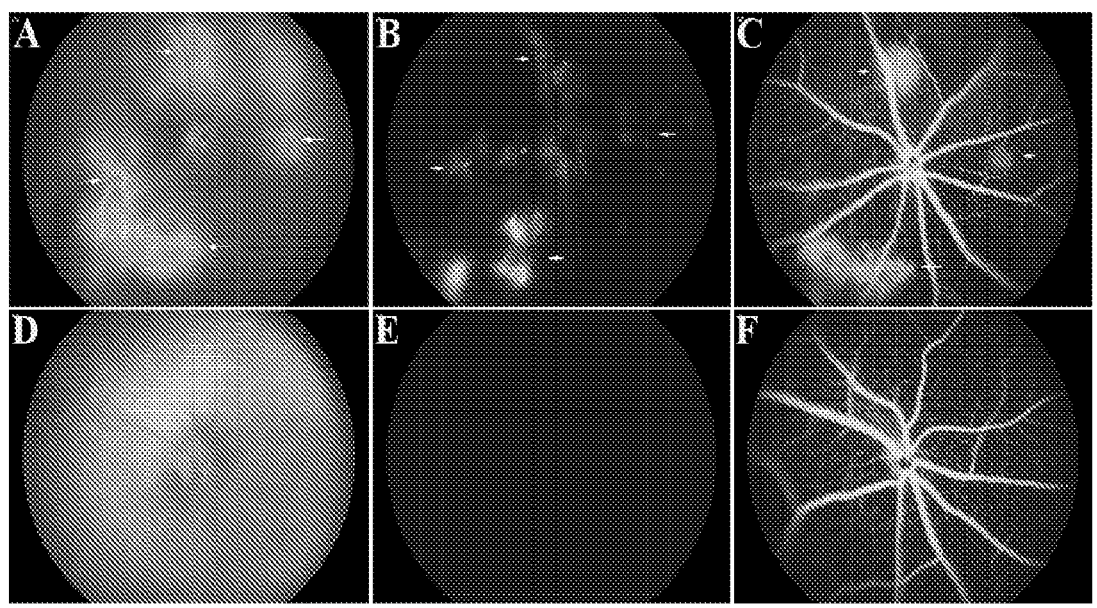
FIGs. 10A-F

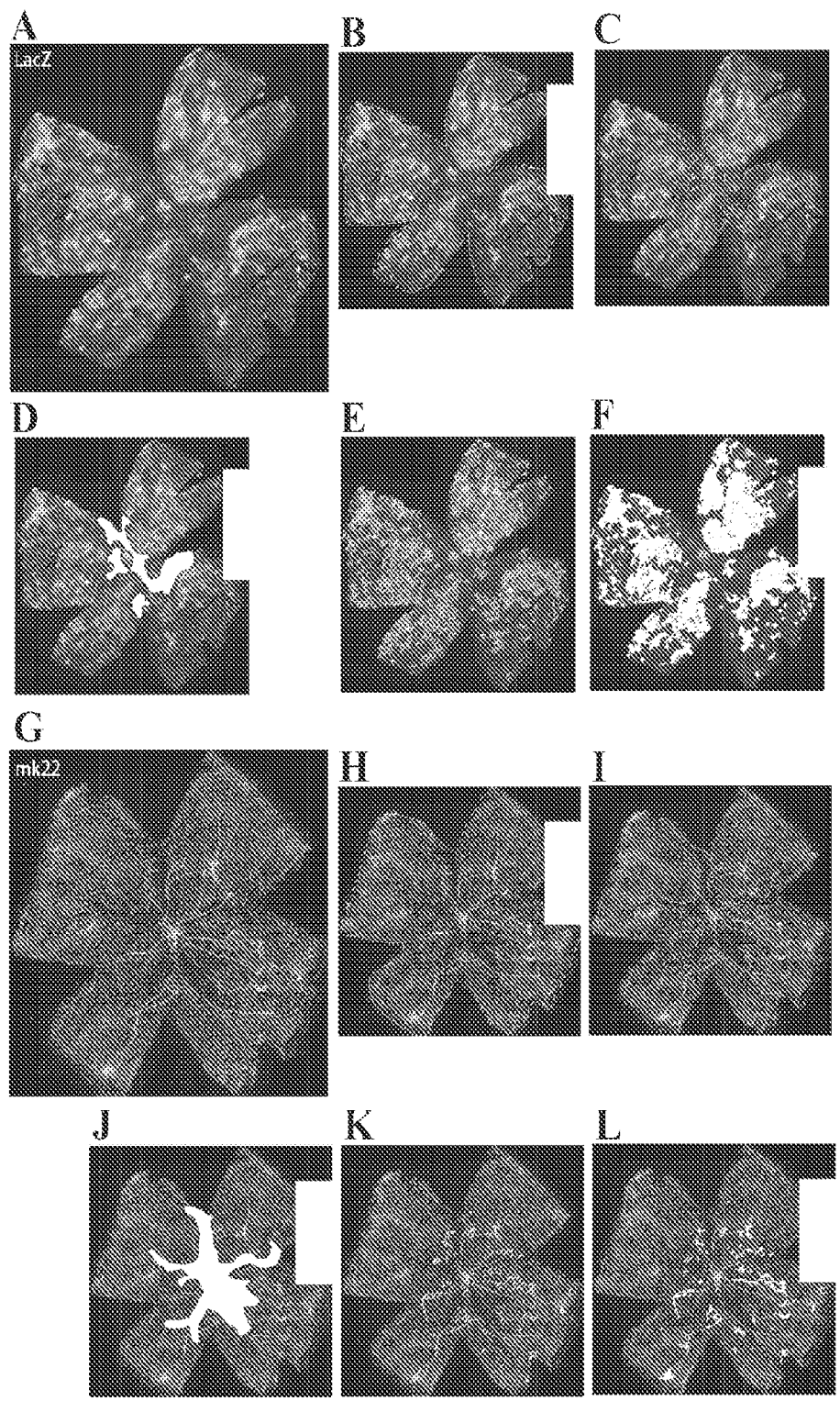
FIGs. 11A-L

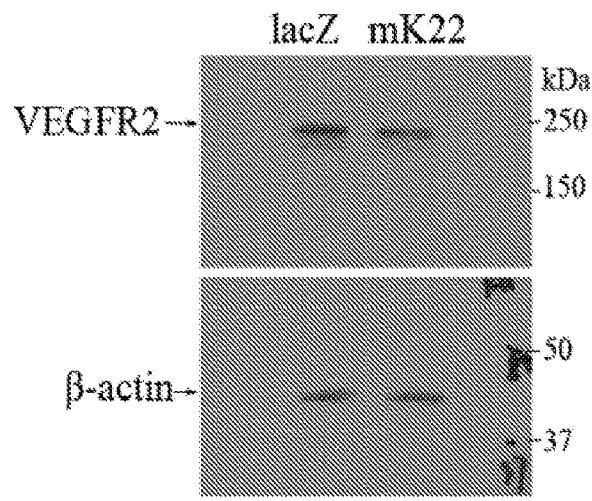
FIG. 12
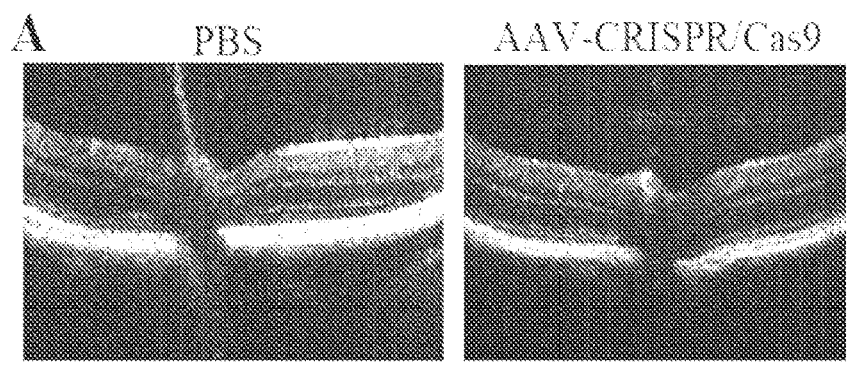
FIG. 13A
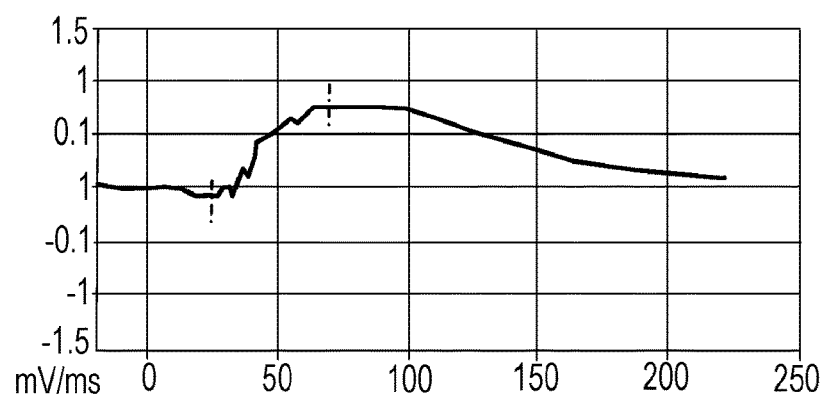
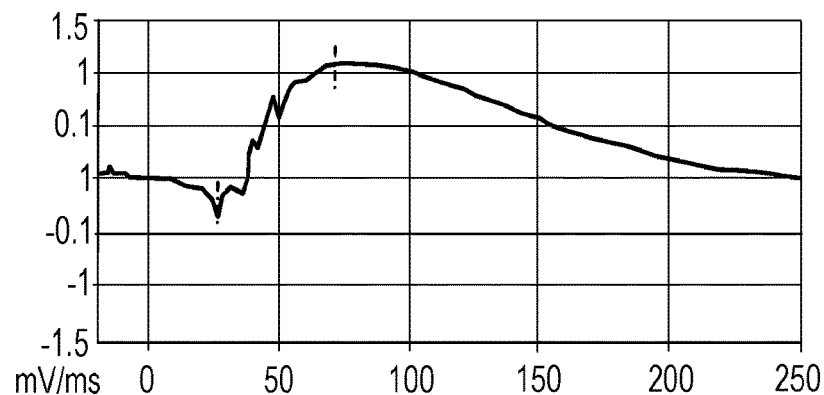
FIG. 13B

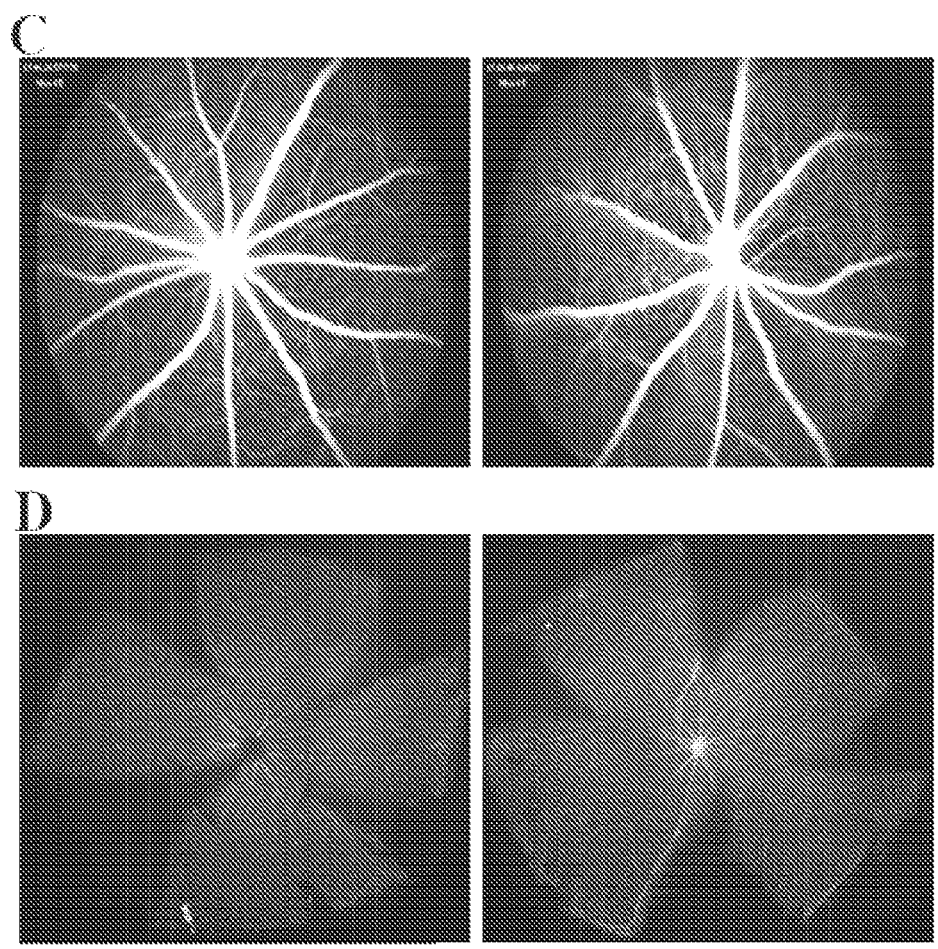
FIGs. 13C-D though methods and materials similar or equivalent to those described herein can be used in the practice or testing of the present invention, suitable methods and materials are described below.

AAV-CRISPR/CAS9 GENOME EDITING OF VEGFR2 FOR TREATING OCULAR DISEASES

CLAIM OF PRIORITY

This application is a 371 U.S. National Phase Application of PCT/US2018/039699, filed on Jun. 27, 2018, which claims the benefit of U.S. Application No. 62/525,545, filed on Jun. 27, 2017. The entire contents of the foregoing are hereby incorporated by reference.

FEDERALLY SPONSORED RESEARCH OR DEVELOPMENT

This invention was made with Government support under Grant No. EY012509 awarded by the National Institutes of Health. The Government has certain rights in the invention.

SEQUENCE LISTING

The instant application contains a Sequence Listing that has been submitted electronically in ASCII format and is hereby incorporated by reference in its entirety. Said ASCII copy, created on Nov. 17, 2021, is named "Sequence Listing" and is 87 bytes in size.

TECHNICAL FIELD

Described herein are compositions, e.g., Adeno-Associated Virus (AAV) Vectors comprising sequences encoding CRISPR/Cas9 proteins and guide RNA, and methods of use thereof for editing of vascular endothelial growth factor receptor 2 (VEGFR2) gene to treat ocular disease associated with pathological angiogenesis, e.g., neovascular age-related macular degeneration (wet AMD), retinopathy of prematurity (ROP), and proliferative diabetic retinopathy (PDR).

BACKGROUND

Vascular endothelial growth factor (VEGF) plays a critical role in angiogenesis, the process by which new blood vessels grow from pre-existing vessels [1-3]. Among the VEGF receptors 1, 2, and 3 (VEGFR1, 2, and 3), VEGFR2 mediates nearly all known VEGF-induced output, including microvascular permeability and neovascularization (NV) [4]. NV is critical for supporting the rapid growth of solid tumors beyond 1-2 $mm^3$ and for tumor metastasis [5]. Abnormal angiogenesis is also associated with a variety of other human diseases such as proliferative diabetic retinopathy (PDR) [6, 7], retinopathy of prematurity (ROP) [8], and wet age-related macular degeneration (AMD) [9, 10]. PDR accounts for the highest incidence of acquired blindness in the working-age population [6, 7]; ROP is a major cause of acquired blindness in children[8]; AMD represents the leading cause of blindness in people over the age of 65 afflicting 30-50 million people globally [10]. Preventing VEGF-stimulated activation of its receptors with neutralizing VEGF antibodies (ranibizumab & bevacizumab) and the extracellular domains of VEGFR1 & 2 (aflibercept) is currently an important therapeutic approach to angiogenesis in these eye diseases but requires chronic treatment[8, 10]. Although these anti-VEGF agents can reduce neo-vascular growth and lessen vascular leakage, there are still therapeutic challenges to a significant number of patients with these eye diseases [11].

SUMMARY

Angiogenesis, in which vascular endothelial growth factor receptor (VEGFR) 2 plays an essential role, is associated with a variety of human diseases including proliferative diabetic retinopathy (PDR) and wet age-related macular degeneration. Described herein is a system of adeno-associated viruses (AAVs)-mediated clustered regularly interspaced short palindromic repeats (CRISPR)— associated endonuclease (Cas)9 from *Streptococcus pyogenes* (SpCas9) used to deplete VEGFR2 in vascular endothelial cells (ECs), where expression of SpCas9 is driven by an endothelial-specific promoter of intercellular adhesion molecule 2 (ICAM2). Recombinant AAV serotype 1 (rAAV1) preferentially transduces pathologic vessels, and editing of genomic VEGFR2 locus using rAAV1-mediated CRISPR/Cas9 abrogated angiogenesis in mouse models of oxygen-induced retinopathy and laser-induced choroid neovascularization. This work establishes genome editing as a strategy to treat angiogenesis-associated ocular diseases.

Thus in a first aspect, provided herein are methods for treating an ocular disease associated with angiogenesis in a subject. The methods include administering to the subject a CRISPR/Cas9 editing complex comprising a guide RNA targeting a VEGFR2 gene, wherein the administering is using an adeno-associated virus 1 (AAV1) vector.

In some embodiments, the methods include administering an AAV1 vector comprising a sequence encoding *Streptococcus pyogenes* (SpCas9) under the control of an endothelial cell-specific promoter. In some embodiments, the endothelial cell-specific promoter is an ICAM-2 promoter.

In some embodiments, the methods include administering an AAV1 vector comprising (i) a sequence encoding *Streptococcus pyogenes* (SpCas9) under the control of an endothelial cell-specific promoter, and (ii) a sequence encoding the guide RNA targeting the VEGFR2 gene. In some embodiments, the endothelial cell-specific promoter is an ICAM-2 promoter.

In some embodiments, the AAV1 is administered by intraocular injection.

In some embodiments, the guide RNA targets exon 3 of the VEGFR2 gene. In some embodiments, the guide RNA targets SEQ ID NO:14.

In some embodiments, the subject has proliferative diabetic retinopathy (PDR), retinopathy of prematurity (ROP), or wet age-related macular degeneration (AMD).

Also provided herein are compositions comprising (i) an AAV1 vector comprising a sequence encoding *Streptococcus pyogenes* (SpCas9) under the control of an endothelial cell-specific promoter, and (ii) a sequence encoding a guide RNA targeting a VEGFR2 gene. In some embodiments, the endothelial cell-specific promoter is an ICAM-2 promoter. In some embodiments, the composition or AAV1 is formulated to be administered by intraocular injection. In some embodiments, the guide RNA targets exon 3 of the VEGFR2 gene. In some embodiments, the guide RNA targets SEQ ID NO:14.

Also provided are the compositions described herein for use in treating an ocular disease associated with angiogenesis in a subject. In some embodiments, the subject has proliferative diabetic retinopathy (PDR), retinopathy of prematurity (ROP), or wet age-related macular degeneration (AMD).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIGS. 1A-F. AAV-CRISPR/Cas9-mediated depletion of VEGFR2 in vitro. (A) Schematic of AAV-SpGuide (V1)[15]. Graphical representation of the mouse VEGFR2-targeted locus (TGTCGACGTCCCGGTACGAGCACTTGTAGG-CTCCAGTAT, SEQ ID NO:17). The oligos of mK22 and its compliment were annealed and cloned into the V1 vector by SapI. The PAM (AGC) is marked with a dark bar. ITR: inverted terminal repeat; U6: a promoter of polymerase III; CMV: a promoter of cytomegalovirus; GFP: green fluorescent protein. (B) Schematic of AAV-SpCas9 (V3). pMecp2: a neuron-specific promoter for methyl CpG binding protein in V0 was substituted for pICAM2 [19] by XbaI/AgeI. (Sequences shown, AACGTCCCGGTACGAGCACTTGT, SEQ ID NO:18; AACACAAGTGCTCGTACCTTTAC, SEQ ID NO:19) (C) Transduction of cultured cells with rAAV1. HRECs, HUVECs and hPRPE cells in a 48-well plate to 50% confluence were infected with rAAV1-CMV-GFP [2 µl/well, 3.75×10$^{12}$ viral genome-containing particles (vg)/ml]. Three days later the cells were photographed under an immunofluorescence microscope. Three independent experiments showed rAAV1 transduction efficiency in HRECs, HUVECs and hPRPE cells of 85.6±2.2%, 88.5±2.3% and 86.8±2.6%, respectively. Scale bar: 200 µm. (D) pICAM2-driven expression of SpCas9 in ECs. After transduction with rAAV1-CMV-GFP (GFP) or rAAV1-pICAM2-SpCas9 (SpCas9) (2 µl/well, 3.75×10$^{12}$ vg/ml) in a 48-well plate for four days, cell lysates were subjected to western blot analysis with antibodies against Cas9 and β-actin. Data shown are representative of three independent experiments. kDa:kilodalton. (E) Sanger DNA sequencing was conducted on PCR products amplified from the genomic VEGFR2 loci of MVECs, which were transduced by rAAV1-SpCas9 plus rAAV1-lacZ (lacZ; TGTCGAC-GTCCCGGTACGAGCACTTGTAGGC, SEQ ID NO:20) or rAAV1-mK22 (mK22; TGTCGACGTCCCGGTAC-GAGCACTNNNNGNN, SEQ ID NO:21). (F) Depletion of VEGFR2 expression using AAV-CRISPR/Cas9. Total cell lysates from the transduced MVECs were subjected to western blot analysis with antibodies against VEGFR2 and β-actin. The bar graphs are mean±standard deviation (SD) of three independent experiments. "*" indicates a significant difference between the compared two groups using an unpaired t test. p<0.05.

FIGS. 2A-I. Transduction of ECs with rAAV1 in vivo. (A-B) On P7, C57BL/6J litters were exposed to 75% oxygen until P12 [23, 37] when the pups were injected intravitreally with rAAV1-CMV-GFP (1 µl, 3.75×10$^{12}$ vg/ml). After return to room air (21% oxygen) for five days, and whole mount retinas from the euthanized mice were stained with IB4. Images were taken under TxRed channel (A & C), GFP channel (B & D). E: merged image of A1 & B1. Scale bar: 200 µm. (F & I) Four lesions were induced in an eight-week-old mouse on the Bruch's membrane using a 532-nm green laser. rAAV1-CMV-GFP (1 µl, 3.75×10$^{12}$ vg/ml) was injected intravitreally into the mouse. Seven days later, the whole-mount choroid was stained with IB4, and images were taken under GFP channel (F & G) and Txred channel (H). I: a merged image of G and H. Scale bar: 200 µm in E & I, and 500 µm in A, B & F. Each figure represents at least six ones from different mice.

FIGS. 3A-F. Editing genomic VEGFR2 abrogated hypoxia-induced angiogenesis. (A) Litters of P12 mice that had been exposed to 75% oxygen for five days were injected intravitreally with 1 µl (3.75×10$^{12}$ vg/ml) containing equal rAAV1-SpCas9 and rAAV1-lacZ (lacZ) or rAAV1-mK22 (mK22). On P17, whole-mount-retinas were stained with IB4. lacZ and mK22 indicate retinas from the rAAV1-SpCas9/lacZ and mK22-injected mice, respectively. Scale bar: 500 µm (B) Analysis of avascular areas from the IB4 stained retinas (n=6). (C) Analysis of NV areas from the IB4 stained retinas (n=6). (D) NGS analysis of indels. The DNA fragments around the PAM sequences were PCR amplified from genomic DNA of the rAAV1-SpCas9/lacZ or -mK22-injected retinas, and then subjected to NGS. (Sequences shown, TGTCCCGGTACGAGCACTTGTAGGCTCC, SEQ ID NO:22; TGTCCCGGTACGAGCACTG-TAGGCTCC, SEQ ID NO:23; TGTCCCGGTACGAGC-ACTTTGTAGGCTCC, SEQ ID NO:24.) (E) The lysates of the rAAV1-SpCas9/lacZ or -mK22-injected retinas were subjected to western blot analysis using indicated antibodies. (F) A bar graph with data showing mean±SD expression in three retinas. "*" indicates significant difference using an unpaired t test. p<0.05.

FIGS. 4A-F. AAV-CRISPR/Cas9 targeting genomic VEGFR2 suppressed NV in laser-induced choroid NV in mice. After laser injury of Bruch's membrane, fundus images (day 0) were taken using the Micron III system, and the mice were injected intravitreally with 1 µl (3.75×10$^{12}$ vg/ml) containing equal rAAV1-SpCas9 and rAAV1-lacZ or -mK22 right immediately after the laser injury (A) or seven days of the laser injury (D). Scale bar: 500 µm. Seven days after AAV1 injection, the mice were injected intraperitoneally with fluorescein, and the FA images were taken using the Micron III system. Subsequently, whole mounts of choroids were stained with IB4, and the images were taken under an immunofluorescence microscope. Areas of NV were analyzed based on the images of FA (B & E) and IB staining (C & F) (n=6). "*" indicates significant difference between the compare two groups using an unpaired t test. p<0.05.

FIGS. 7A-D. rAAV1 transduction of ECs in the normal retinal vessel. On P12, control mice (raised in room air) were intravitreally injected with rAAV1 with a GFP gene driven by CMV) (rAAV1-CMV-GFP) (1 μl, $3.75 \times 10^{12}$ vg/ml) from the Gene Transfer Vector Core at Schepens Eye Research Institute (Boston, Mass.). On P17, after euthanasia, the mouse eyes were carefully removed and fixed in 3.7% paraformaldehyde. Retinas were dissected, whole-mounted and then stained overnight at 4° C. with murine-specific EC marker isolectin 4 (IB4)-Alexa 594 (red) [23, 38-39]. The images were taken with an EVOS FL Auto microscope. (A) Normal superficial retinal vessels from a control mouse, scale bar: 500 μm; (B-D) Partial superficial retinal vessel from one of the rAAV1-CMV-GFP injected mice raised in room air. (B) IB4 staining of ECs (TxRed channel), (C) GFP expression (GFP channel), (D) A merged image of B & C, Scale bar: 200 μm. Each figure represents six ones from different mice.

FIGS. 8A-C. rAAV1 transduction of ECs in the pathological retinal capillaries. On P12, experimental of mice (raised in 75% oxygen for five days) were intravitreally injected with rAAV1-CMV-GFP (1 μl, $3.75 \times 10^{12}$ vg/ml). On P17, after euthanasia, the mouse eyes were carefully removed and processed as for FIG. 5 [23, 38-39]. The images were taken with an EVOS FL Auto microscope. (A) IB4 staining of ECs (TxRed channel), (B) GFP expression (GFP channel), (C) A merged image of B & C, Scale bar: 200 μm.

FIGS. 9A-G. Analysis of transduced ECs and pathological retinal vessel. A. The pixels of IB4 staining in pathological vessels (IB4) or GFP positive stain (GFP) to those of the whole retinal area were folded. There was no significant difference between the quantitation of IB4 staining in pathological vessels and GFP positive staining (n=6). NS: No significant difference. Screen shots of the whole retina IB4 or GFP staining when quantitation was performed as described in Methods and previously[3]. Briefly, quantification of neovascularization (NV) at P17. (B-D) Images of retinal whole-mount stained for endothelial cells with isolectin B4-594; (E-G) Images of retinal whole-mount for GFP under green channel. Scale bar: 500 μm.

FIGS. 10A-F. rAAV1 infection of the laser-injured area. After laser photocoagulation of the eyes of eight week-old mice (C57BL/6J) using a Streampix5 laser system, rAAV1 (1 μl, $3.75 \times 10^{12}$ vg/ml) was injected into the vitreous of the left eye (A, B, and C). The right one (D, E and F) was uninjected and served as a control. On day seven, fundus images were taken using the Micron III retina imaging system with illumine (A, D) or UV light (B, E). Then 0.01 ml of 25% sodium fluorescein was injected intraperitoneally. Images of fluorescein angiography represent six ones from different mice and were taken with UV light (C, F). Scale bar: 500 μm.

FIGS. 11A-L. Analysis of vaso-obliteration and NV area at P17 (n=6) conducted as described in Methods and previously[3]. A. Image of retinal whole-mount stained for endothelial cells with isolectin B4-594 from a mouse intravitreally injected with AAV-SpCas9 and AAV-lacZ-sgRNA (mK22); (B-D) retinal whole-mount with entire avascular (vaso-obliterated) area highlighted in white. (E-F) Screenshots of retinal whole-mount with the neovascular tufts highlighted. G. Image of retinal whole-mount stained for endothelial cells with isolectin B4-594 from a mouse intravitreally injected with AAV-SpCas9 and AAV-VEGFR2-sgRNA (mK22); (H-J) retinal whole-mount with entire avascular (vaso-obliterated) area highlighted in white. (K-L) Screenshots of retinal whole-mount with the neovascular tufts highlighted. Scale bar: 500 μm.

FIG. 12. Depletion of VEGFR2 in retinas. The lysates of the rAAV1-SpCas9/lacZ—sgRNA (lacZ) or—VEGFR2-sgRNA (mK22)-injected retinas were subjected to western blot analysis using indicated antibodies. This is representative of three independent experiments.

FIGS. 13A-D. Examination of toxicity of the dual AAV-CRISPR/Cas9. Five P12 mice were injected with the dual AAV-CRISPR/Cas9 (1 μl, $3.75 \times 10^{12}$ vg/ml) or 1 μl of phosphate buffered saline (PBS) into the left eye or the right eye, respectively. After four weeks, the mice were examined by optical coherence tomography (OCT) (A), electroretinography (ERG) (B), fluorescein fundus angiography (FFA) (C) and whole-mount retinal staining with IB4 (D). Scale bar: 500 μm.

DETAILED DESCRIPTION

Figure 4D:
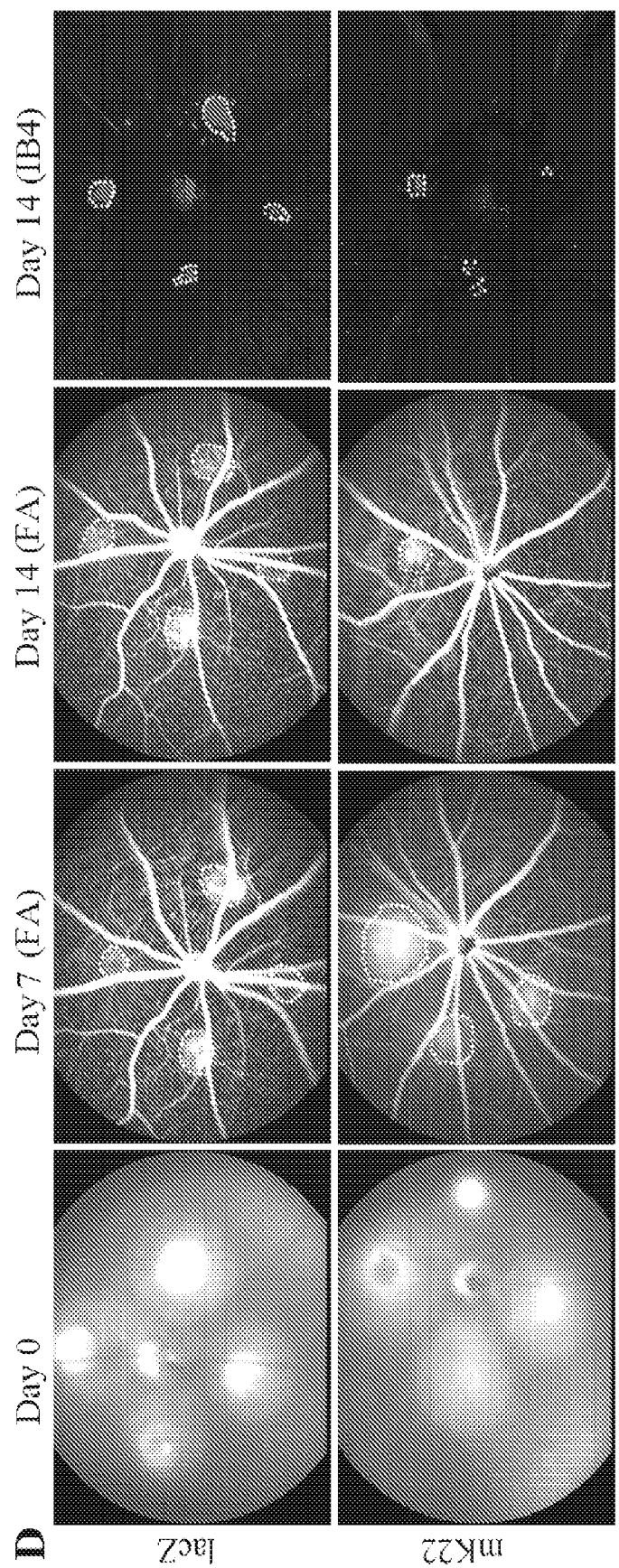

Adeno-associated viruses (AAVs) are small viruses that are not currently known to cause any disease, and their derived vectors show promise in human gene therapy [12, 13]. The clustered regularly interspersed palindromic repeats (CRISPR)-associated DNA endonuclease (Cas) 9 in *Streptococcus pyogenes* (SpCas9) processes pre-crRNA transcribed from the repeat spacers into CRISPR RNAs (crRNA) and cleave invading nucleic acids on the guidance of crRNA and trans-activating crRNA (tracrRNA) [14, 15]. A single guide RNA (sgRNA) engineered as the crRNA-tracrRNA chimeric RNA can direct sequence-specific SpCas9 cleavage of double strand DNA containing an adjacent "NGG" protospacer-adjacent motif (PAM) [14]. This CRISPR/Cas9 system is a powerful tool for the targeted introduction of mutations into eukaryotic genomes and subsequent protein depletion [16, 17].

In this study, we employed the AAV-mediated CRISPR/Cas9 system to edit genomic VEGFR2 in vivo.

We report that rAAV1 preferentially transduced vascular ECs of pathological vessels in both mouse models of OIR and laser-injury induced CNV (FIG. 3 and FIG. 9) while also transducing normal vascular ECs in the retina (FIG. 7). The preferential transduction of ECs in pathological vessels may be due to the fact the neovessels are less mature than normal vessels, and have incomplete basement membrane and weaker intercellular junctions. To date, AAV vectors has been used in a number of clinical trials such as for Leber' congenital amaurosis[25-27] and congestive heart failure[28] and has been approved for treatment of lipoprotein lipase deficiency in Europe[29, 30]. While anti-VEGF agents (e.g. ranibizumab and aflibercept) can reduce neovascularization growth and vascular leakage associated eye diseases (e.g. PDR and wet AMD), therapeutic challenges remain, including the need for chronic treatment and a significant number of patients who do not respond[11]; gene therapy targeting genomic VEGFR2 using AAV-CRIPSR/Cas9 may provide a novel alternative approach. While other genes, such as MMP9[31, 32] have been linked to various proliferative retinopathies, none has been shown to drive new vessel disease to the extent seen VEGFR2.

Success translation of genome editing technologies to the clinic must address some major obstacles, primarily in terms of the safety and efficacy; genetic modifications are permanent, and deleterious off-target mutations could create cells with oncogenic potential, reduced cellular integrity and or functional impairment [33, 34]. Our results demonstrate that expression of VEGFR2 was depleted by 80% in vitro (MVECs) (FIG. 1) and by 30% in vivo (retina) (FIG. 3) by the AAV-CRISRP/Cas9 (mK22), in which SpCas9 was driven by an endothelial cell specific promoter pICAM2 (FIG. 1). In addition, NGS analysis indicated that there was only about 2% indels around the PAM in the PCR products amplified from the treated P17 mouse retinas, and there was a significant decrease in NV in both mouse models of OIR (FIG. 3) and CNV (FIG. 4) after treatment with AAV-CRISPR-Cas9 targeting genomic VEGFR2 in comparison to targeting control lacZ. In summary, our studies show that precise and efficient gene editing of VEGFR2 using CRISPR-Cas9 systems has the potential to treat angiogenesis-associated diseases.

Subjects

The methods described herein can be used to prevent (reduce the risk of developing), or reduce the risk or rate of progression of ocular diseases associated with angiogenesis/neovascularization. For example, the methods can be used to treat, reduce the risk of developing, or reduce the risk or rate of progression of these diseases in patients. In addition, the methods can be used to treat, reduce the risk of developing, or the risk or rate of progression of, proliferative diabetic retinopathy (PDR), retinopathy of prematurity (ROP), and wet age-related macular degeneration (AMD).

The methods described herein can include identifying and/or selecting a subject who is in need of treatment for, or to prevent the development of, ocular diseases associated with intraocular pathological angiogenesis (e.g., PDR, ROP and/or wet AMD) (e.g., selecting the subject on the basis of the need of treatment). As used herein, "at risk for" means that the subject has (e.g., is determined to have using known methods) a risk of developing the condition that is statistically significantly above the risk level of the general population.

Proliferative Diabetic Retinopathy (PDR)

PDR is a common complication of diabetes mellitus and the leading cause of new blindness in persons aged 25-74 years in the United States. Signs of diabetic retinopathy (DR) include microaneurysms and hemorrhages (dot and blot, or flame-shaped); retinal edema and hard exudates; cotton-wool spots; venous loops and venous beading; and intraretinal microvascular abnormalities in a subject with diabetes (e.g., diagnosed based upon glucose and hemoglobin A1c measurements). The presence of neovascularization is a hallmark of PDR; in addition, preretinal hemorrhages, hemorrhage into the vitreous, fibrovascular tissue proliferation; traction retinal detachments, and macular edema may be present in PDR. Diagnosis is typically made by fluorescein angiography, Optical coherence tomography (OCT), or B-scan ultrasonography.

In some embodiments the methods include identifying, selecting, and/or treating a subject with diabetes who has or is at risk of developing PDR. In some embodiments, the methods include monitoring the subject for early signs of the development of PDR or DR, and administering one or more doses of a VEGFR2 editing complex as described herein. The methods can also be used to treat subjects without present signs of PDR but who are at risk for PDR.

Standard treatments can include, e.g., intravitreal administration of triamcinolone, bevacizumab, or ranibizumab; laser photocoagulation; vitrectomy; or cryotherapy.

Retinopathy of Prematurity (ROP)

ROP affects immature vasculature in the eyes of premature babies, and can be mild with no visual defects or aggressive with neovascularization that can progress to retinal detachment and blindness. In some embodiments the methods include identifying, selecting, and/or treating a pre-term infant who has or is at risk of developing ROP. In some embodiments, the methods include monitoring the subject for early signs of the development of ROP, and administering one or more doses of a VEGFR2 editing complex as described herein. The methods can also be used to treat subjects (e.g., preterm infants born before 32 weeks' gestation) without present signs of ROP but who are at risk for ROP.

Wet Age-Related Macular Degeneration (AMD)

In early stages of AMD insoluble extracellular aggregates called drusen accumulate in the retina. Advanced AMD occurs as either dry (atrophic) or wet (neovascular) AMD. In the former, geographic atrophy results in RPE atrophy, degeneration of the outer retinal layer, and sclerosis of choriocapillaris. Wet AMD is characterized by the presence of choroidal neovascularization (CNV): abnormal and immature blood vessels grow from the choroidal vasculature, through breaks in Bruch's membrane, toward the outer retina; these blood vessels leak fluid below or within the retina (Yanai et al., Proc Natl Acad Sci USA. 2014 Jul. 1; 111(26): 9603-9608; Wang et al., Eye (Lond). 2011 February; 25(2): 127-139). The two forms of AMD can occur together. Neovascular AMD accounts for 10 to 20% of AMD cases and leads to sudden and severe loss of vision (Ferris et al., Arch Ophthalmol. 1984 November; 102(11):1640-2). Current standard of care for patients with CNV/wet AMD involves targeting the proangiogenic and permeability molecule vascular endothelial growth factor-A (VEGF). However, although current anti-VEGF therapy blocks vascular permeability and angiogenesis, it does not lead to complete vascular regression (Gragoudas et al., N Engl J Med. 2004 Dec. 30; 351(27):2805-16; Yanai et al., Proc Natl Acad Sci USA. 2014 Jul. 1; 111(26): 9603-9608) and the treatment is not effective in all subjects (Takeda et al., Nature. 2009 Jul. 9; 460(7252): 225-230).

In some embodiments the methods include identifying, selecting, and/or treating a subject who has CNV or wet AMD. In some embodiments, the methods include monitoring the subject for early signs of the development of CNV or AMD (e.g., presence of drusen), and administering one or more doses of a VEGFR2 editing complex as described herein. The methods can also be used to treat subjects without present signs of CNV or wet AMD but who are at risk for CNV or wet AMD. Diagnosis of AMD or CNV can be made using known methods, e.g., Amsler grid, fluorescein angiography or Optical coherence tomography (OCT).

Methods of Treating or Reducing Risk of Ocular Neovascularization

The methods described herein include the use of a VEGFR2 editing complex in subjects who have or are at risk of developing a first or recurring ocular neovascularization, e.g., in subjects who have PDR, ROP, or wet AMD, or who are at risk for developing PDR, ROP, or wet AMD.

The methods described herein include the use of an effective amount of a VEGFR2 editing complex. An "effective amount" is an amount sufficient to effect beneficial or desired results, e.g., the desired therapeutic effect. An effective amount can be administered in one or more administrations, applications or dosages. The compositions can be administered, e.g., once per month or more after first administration. The skilled artisan will appreciate that certain factors may influence the dosage and timing required to effectively treat a subject, including but not limited to the severity of the disease or disorder, previous treatments, the general health and/or age of the subject, and other diseases present.

In some embodiments, intravitreal injections of a VEGFR2 editing complex are performed aseptically after the topical application of anaesthesia and an antiseptic agent to the conjunctival sac. In some embodiments, each subject receives an intravitreal injection of a VEGFR2 editing complex.

In some embodiments, the subjects receive a sustained release implant, e.g., as described above, that will release the VEGFR2 editing complex over time, e.g., over a week, two weeks, a month, two months, three months, six months, or a year. In some embodiments, the methods include administering subsequent implants to provide administration of the VEGFR2 editing complex for at least six months, one year, two years, or more.

In some embodiments, the VEGFR2 editing complex is administered in combination with one or more additional treatments, e.g., pharmaceutical treatments such as e.g., anti-VEGF agents (e.g., neutralizing VEGF antibodies (ranibizumab & bevacizumab) or recombinant fusion protein with the partial extracellular domains of VEGFR1 and 2 (aflibercept)) or corticosteroids (e.g., triamcinolone), or surgical treatments such as laser surgery (e.g., xenon, argon, diode), cryotherapy, pars plana vitrectomy (PPV), Retinal Detachment (RD) surgery; ERM surgery, scleral buckle surgery and/or vitrectomy.

Nucleic Acids Encoding a CRISPR VEGFR2 Editing Complex

The present methods include the delivery of nucleic acids encoding the components of a CRISPR VEGFR2 editing complex. The VEGFR2 editing complex includes a Cas9 editing enzyme and one or more guide RNAs directing the editing enzyme to VEGFR2.

Guide RNAs Directing the Editing Enzyme to VEGFR2

The gene editing complex includes guide RNAs directing the editing enzyme to VEGFR2, i.e., comprising a sequence that is complementary to the sequence of a nucleic acid encoding VEGFR2, and that include a PAM sequence that is targetable by the co-administered Cas9 editing enzyme. In some embodiments, the sequence of exon 3 of VEGFR2 is targeted by the guide RNA, i.e., comprising a sequence that is complementary to the sequence of 17-20 nucleotides of a nucleic acid encoding exon 3 of VEGFR2.

VEGFR2 is also known as kinase insert domain receptor (KDR), Fetal Liver Kinase 1 (FLK1), and cluster of differentiation 309 (CD309). The gene encoding the human VEGFR2 precursor is at nucleotides 55078259-55125595 of chromosome 4 (Assembly GRCh38.p7; see GenBank Acc. No. NC_000004.12, complement). See also RefSeqGene No. NG 012004.1, Range5001-52337. See SEQ ID NO:12, below. Exemplary guide sequences targeting human VEGFR2 include those targeting exon 3, e.g., as described in Huang et al., Invest Ophthalmol Vis Sci. 2017 February; 58(2): 1228-1236 (e.g., 5'-TTCCCGGTAGAAGCACTTGT-3' (K12) (SEQ ID NO:14)).

Although the present examples exemplify the use of SpCas9, other Cas9s from other species can also be used, as discussed below. Preferably a single guide RNA (sgRNA) is used, though a crRNA/tracrRNA pair can also be used. Suitable guide RNAs and target sequences for use with spCAS9 and other Cas9s that are specific (i.e., have few or no off-target binding sites) can readily be identified using known methods. See, e.g., Aach, et al. (2014) Flexible algorithm for identifying specific Cas9 targets in genomes. BioRxiv, Cold Spring Harbor Labs. doi: dx.doi.org/10.1101/005074; Bae et al. (2014) Cas-OFFinder: a fast and versatile algorithm that searches for potential off-target sites of Cas9 RNA-guided endonucleases. Bioinformatics. 30(10):1473-1475; Gratz, et al. (2014) Highly specific and efficient CRISPR/Cas9-catalyzed homology-directed repair in *Drosophila*. Genetics. 196(4):961-971; Heigwer et al. (2014) E-CRISP: fast CRISPR target site identification. Nat Methods. 11(2):122-123; Hsu et al. (2013) DNA targeting specificity of RNA-guided Cas9 nucleases. Nat Biotechnol. 31(9):827-832; Ma et al. (2013) A guide RNA sequence design platform for the CRISPR/Cas9 system for model organism genomes. Biomed Res Int. doi.org/10.1155/2013/270805; Montague et al. (2014) CHOPCHOP: a CRISPR/Cas9 and TALEN web tool for genome editing. Nucleic Acids Res. 42(W1):W401-W407; Liu et al. (2015) CRISPR-ERA: a comprehensive design tool for CRISPR-mediated gene editing, repression and activation. Bioinformatics. 31(22):3676-3678; Ran et al. (2015) In vivo genome editing using *Staphylococcus aureus* Cas9. Nature. 520(7546):186-191; Wu et al. (2014) Target specificity of the CRISPR-Cas9 system. Quant Biol. 2(2):59-70; Xiao et al. (2014) CasOT: a genome-wide Cas9/gRNA off-target searching tool. Bioinformatics. 30(8):1180-1182; Zetsche et al. (2015) Cpf1 is a single RNA-guided endonuclease of a Class 2 CRISPR-Cas System. Cell. 163(3):759-771; WO2014152432; WO2014144592; WO2014144288; WO2014204578; WO2014144761; WO2015099850; and U.S. Pat. No. 8,697,359, inter alia.

Cas9 Editing Enzymes

The methods include the delivery of Cas9 editing enzymes to the cancer cells. Some exemplary Cas9s, and their cognate PAMs, are shown in the following table.

| Cas9s from various species | |
| --- | --- |
| Species/Variant of Cas9 | PAM Sequence |
| SpCas9 D1135E variant | NGG (reduced NAG binding) |
| SpCas9 VRER variant | NGCG |
| SpCas9 EQR variant | NGAG |
| SpCas9 VQR variant | NGAN or NGNG |
| Streptococcus thermophilus (ST) | NNAGAAW |
| Treponema denticola (TD) | NAAAAC |
| Streptococcus pyogenes (SP); SpCas9 | NGG |
| Staphylococcus aureus (SA); SaCas9 | NNGRRT or NNGRR(N) |
| Neisseria meningitidis (NM) | NNNNGATT |

The sequences of the Cas9s are known in the art; see, e.g., Kleinstiver et al., Nature. 2015 Jul. 23; 523(7561): 481-485; WO 2016/141224; U.S. Pat. No. 9,512,446; US-2014-0295557; WO 2014/204578; and WO 2014/144761. The methods can also include the use of the other previously described variants of the SpCas9 platform (e.g., truncated sgRNAs (Tsai et al., Nat Biotechnol 33, 187-197 (2015); Fu et al., Nat Biotechnol 32, 279-284 (2014)), nickase mutations (Mali et al., Nat Biotechnol 31, 833-838 (2013); Ran et al., Cell 154, 1380-1389 (2013)), FokI-dCas9 fusions (Guilinger et al., Nat Biotechnol 32, 577-582 (2014); Tsai et al., Nat Biotechnol 32, 569-576 (2014); WO2014144288).

The SpCas9 wild type sequence is as follows:

(SEQ ID NO: 15)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NPFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD

The SaCas9 wild type sequence is as follows:

(SEQ ID NO: 16)
MKRNYILGLDIGITSVGYGIIDYETRDVIDAGVRLFKEANVENNEGRRSK

RGARRLKRRRRHRIQRVKKLLFDYNLLTDHSELSGINPYEARVKGLSQKL

SEEEFSAALLHLAKRRGVHNVNEVEEDTGNELSTKEQISRNSKALEEKYV

AELQLERLKKDGEVRGSINRFKTSDYVKEAKQLLKVQKAYHQLDQSFIDT

YIDLLETRRTYYEGPGEGSPFGWKDIKEWYEMLMGHCTYFPEELRSVKYA

YNADLYNALNDLNNLVITRDENEKLEYYEKFQIIENVFKQKKKPTLKQIA

KEILVNEEDIKGYRVTSTGKPEFTNLKVYHDIKDITARKEIIENAELLDQ

IAKILTIYQSSEDIQEELTNLNSELTQEEIEQISNLKGYTGTHNLSLKAI

NLILDELWHTNDNQIAIFNRLKLVPKKVDLSQQKEIPTTLVDDFILSPVV

KRSFIQSIKVINAIIKKYGLPNDIIIELAREKNSKDAQKMINEMQKRNRQ

TNERIEEIIRTTGKENAKYLIEKIKLHDMQEGKCLYSLEAIPLEDLLNNP

FNYEVDHIIPRSVSFDNSFNNKVLVKQEENSKKGNRTPFQYLSSSDSKIS

YETFKKHILNLAKGKGRISKTKKEYLLEERDINRFSVQKDFINRNLVDTR

YATRGLMNLLRSYFRVNNLDVKVKSINGGFTSFLRRKWKFKKERNKGYKH

HAEDALIIANADFIFKEWKKLDKAKKVMENQMFEEKQAESMPEIETEQEY

KEIFITPHQIKHIKDFKDYKYSHRVDKKPNRELINDTLYSTRKDDKGNTL

IVNNLNGLYDKDNDKLKKLINKSPEKLLMYHHDPQTYQKLKLIMEQYGDE

KNPLYKYYEETGNYLTKYSKKDNGPVIKKIKYYGNKLNAHLDITDDYPNS

RNKVVKLSLKPYRFDVYLDNGVYKFVTVKNLDVIKKENYYEVNSKCYEEA

KKLKKISNQAEFIASFYNNDLIKINGELYRVIGVNNDLLNRIEVNMIDIT

YREYLENMNDKRPPRIIKTIASKTQSIKKYSTDILGNLYEVKSKKHPQII

KKG

See also Hou, Z. et al. Efficient genome engineering in human pluripotent stem cells using Cas9 from *Neisseria meningitidis*. Proc Natl Acad Sci USA (2013); Fonfara, I. et al. Phylogeny of Cas9 determines functional exchangeability of dual-RNA and Cas9 among orthologous type II CRISPR-Cas systems. Nucleic Acids Res 42, 2577-2590 (2014); Esvelt, K. M. et al. Orthogonal Cas9 proteins for RNA-guided gene regulation and editing. Nat Methods 10, 1116-1121 (2013); Cong, L. et al. Multiplex genome engineering using CRISPR/Cas systems. Science 339, 819-823 (2013); Horvath, P. et al. Diversity, activity, and evolution of CRISPR loci in *Streptococcus thermophilus*. J Bacteriol 190, 1401-1412 (2008).

The editing enzymes can include one or more of SpCas9 D1135E variant; SpCas9 VRER variant; SpCas9 EQR variant; SpCas9 VQR variant; *Streptococcus thermophilus* (ST) Cas9 (StCas9); *Treponema denticola* (TD) (TdCas9); *Streptococcus pyogenes* (SP) (SpCas9); *Staphylococcus aureus* (SA) Cas9 (SaCas9); or *Neisseria meningitidis* (NM) Cas9 (NmCas9), as well as variants thereof that are at least 80%, 85%, 90%, 95%, 99% or 100% identical thereto that retain at least one function of the parent case, e.g., the ability to complex with a gRNA, bind to target DNA specified by the gRNA, and alter the sequence of the target DNA.

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 80% (in some embodiments, about 85%, 90%, 95%, or 100% of the length of the reference sequence) is aligned. The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch ((1970) J. Mol. Biol. 48:444-453) algorithm which has been incorporated into the GAP program in the GCG software package, using a Blossum 62 scoring matrix with a gap penalty of 12, a gap extend penalty of 4, and a frameshift gap penalty of 5.

Expression Constructs

Expression constructs encoding one or both of guide RNAs and/or Cas9 editing enzymes can be administered in any effective carrier, e.g., any formulation or composition capable of effectively delivering the component gene to cells in vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

In some embodiments, nucleic acids encoding a CRISPR VEGFR2 gene editing complex (Cas9 and/or gRNA) are entrapped in liposomes bearing positive charges on their surface (e.g., lipofectins). These delivery vehicles can also be used to deliver Cas9 protein/gRNA complexes.

In clinical settings, the gene delivery systems for the nucleic acids encoding a CRISPR VEGFR2 gene editing complex can be introduced into a subject by any of a number of methods, each of which is familiar in the art. In preferred embodiments, the nucleic acids encoding a CRISPR VEGFR2 gene editing complex are introduced by intravitreal injection. In some embodiments, the nucleic acids encoding a CRISPR VEGFR2 gene editing complex are administered during or after a surgical procedure; in some embodiments, a controlled-release hydrogel comprising the nucleic acids encoding a CRISPR VEGFR2 gene editing complex is administered to provide a steady dose of the nucleic acids encoding a CRISPR VEGFR2 gene editing complex over time.

A pharmaceutical preparation of the nucleic acids encoding a CRISPR VEGFR2 gene editing complex can consist essentially of the gene delivery system (e.g., viral vector(s)) in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

Preferably, the CRISPR VEGFR2 editing complex is specific, i.e., induces genomic alterations preferentially at the target site (VEGFR2), and does not induce alterations at other sites, or only rarely induces alterations at other sites.

In the present methods, adeno-associated virus 1 (AAV1) vectors are used as a recombinant gene delivery system for the transfer and expression of the CRISPR VEGF2 editing complex in vivo, particularly into humans. These vectors provide efficient delivery of genes into cells, and in some cases the transferred nucleic acids are stably integrated into the chromosomal DNA of the host. Protocols for producing recombinant viruses and for infecting cells in vitro or in vivo with such viruses can be found in Ausubel, et al., eds., *Gene Therapy Protocols Volume 1: Production and In Vivo Applications of Gene Transfer Vectors*, Humana Press, (2008), pp. 1-32 and other standard laboratory manuals.

Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro and Immunol. 158:97-129 (1992)). AAV vectors efficiently transduce various cell types and can produce long-term expression of transgenes in vivo. Although AAV vector genomes can persist within cells as episomes, vector integration has been observed (see for example Deyle and Russell, Curr Opin Mol Ther. 2009 August; 11(4): 442-447; Asokan et al., Mol Ther. 2012 April; 20(4): 699-708; Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989)). AAV vectors have been extensively used for gene augmentation or replacement and have shown therapeutic efficacy in a range of animal models as well as in the clinic; see, e.g., Mingozzi and High, Nature Reviews Genetics 12, 341-355 (2011); Deyle and Russell, Curr Opin Mol Ther. 2009 August; 11(4): 442-447; Asokan et al., Mol Ther. 2012 April; 20(4): 699-708. AAV vectors containing as little as 300 base pairs of AAV can be packaged and can produce recombinant protein expression. Space for exogenous DNA is limited to about 4.5 kb. In the present methods, AAV1 is used to introduce and express DNA encoding the Cas9 and guide RNA into vascular endothelial cells.

In some embodiments, expression of one or both of the Cas9 and guide RNA is driven by an ICAM2 promoter, e.g., as shown below as SEQ ID NO:13 and/or as described in Cowan et al., J Biol Chem. 1998 May 8; 273(19):11737-44 (the bold portion of SEQ ID NO:13) or in Dai et al., J. Virol. June 2004; 78(12):6209-6221 (see, e.g., FIG. 1B (ICAM2 340 bp promoter) and 1C (140 bp minimal ICAM2 promoter). In some embodiments, expression of the Cas9 protein is driven by an ICAM2 promoter, while expression of the gRNA is driven by a constitutive or other promoter, e.g., human β-actin, human elongation factor-1α (EF1A), chicken β-actin combined with cytomegalovirus early enhancer (CAGG), cytomegalovirus (CMV), simian virus 40 (SV40), human Ubiquitin C promoter (UBC), mouse phosphoglycerate kinase 1 promoter (PGK), or herpes simplex virus thymidine kinase (see, e.g., Damdindorj et al. (2014) A Comparative Analysis of Constitutive Promoters Located in Adeno-Associated Viral Vectors. PLoS ONE 9(8): e106472; Qin et al. (2010) Systematic Comparison of Constitutive Promoters and the Doxycycline-Inducible Promoter. PLoS ONE 5(5): e10611). The reverse can also be used, e.g., expression of the Cas9 protein can be driven by a constitutive promoter, while the gRNA is driven by ICAM2 promoter. Alternatively, both can be driven by the same promoter type. As an alternative to the ICAM2 promoter, a promoter from endoglin (Velasco et al., Gene Therapy (2001) 8, 897-904) or from vascular cell adhesion molecule-1 (VCAM-1), endothelial nitric oxide synthase (eNOS), von Willebrand factor (vWF), fms-like tyrosine kinase-1 (FLT-1), tyrosine kinase with immunoglobulin and epidermal growth factor homology domains (TIE), or kinaselike domain receptor (KDR/VEGFR2) (see, e.g., Nicklin et al., Hypertension. 2001; 38:65-70) can also be used.

A variety of nucleic acids have been introduced into different cell types using AAV vectors (see for example the references cited above and those cited in Asokan et al., Molecular Therapy (2012); 20 4, 699-708; and Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993)).

Pharmaceutical Compositions and Methods of Administration

The methods described herein include the use of pharmaceutical compositions comprising a VEGFR2 editing complex as an active ingredient. Thus also described herein are pharmaceutical compositions comprising a VEGFR2 editing complex formulated for intravitreal or intraocular delivery.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., anti-VEGF agents (e.g., neutralizing VEGF antibodies (ranibizumab & bevacizumab) or recombinant fusion protein with the partial extracellular domains of VEGFR1 and 2 (aflibercept)) or corticosteroids (e.g., triamcinolone). Pharmaceutical compositions are typically formulated to be compatible with its intended route of administration. Examples of routes of administration suitable for use in the present methods can include intravitreal or intraocular administration, topical administration (e.g., eye drops), and intraocular implants. Systemic administration, e.g., oral administration can also be used.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, NY). See also Short, Toxicol Pathol 36(1):49-62 (2008). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for intraocular or intravitreal injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared, e.g., by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. Nanoparticles (1 to 1,000 nm) and microparticles (1 to 1,000 μm), e.g., nanospheres and microspheres and nanocapsules and microcapsules, can also be used. These can be prepared according to methods known to those skilled in the art, for example, as described in U.S. Pat. No. 4,522,811; Bourges et al., *Ocular drug delivery targeting the retina and retinal pigment epithelium using polylactide nanoparticles*. Invest Opth Vis Sci 44:3562-9 (2003); Bourges et al., *Intraocular implants for extended drug delivery: therapeutic applications*. Adv Drug Deliv Rev 58:1182-1202 (2006); Ghate et al., *Ocular drug delivery*. Expert Opin Drug Deliv 3:275-87 (2006); and Short, *Safety Evaluation of Ocular Drug Delivery Formulations: Techniques and Practical Considerations*. Toxicol Pathol 36(1):49-62 (2008).

The pharmaceutical compositions can be included in a container, pack, or dispenser together with instructions for administration in a method described herein.

EXAMPLES

The invention is further described in the following examples, which do not limit the scope of the invention described in the claims.

Materials & Methods

The following materials and methods were used in the Examples below.

Mice

Six-eight week-old mice (C57BL/6J, male and female, 6-8 weeks old) were purchased from Jackson Laboratories (Bar Harbor, Me.). All the animal experiments followed the guidelines of the Association for Research in Vision and Ophthalmology Statement for the Use of Animals in Ophthalmic and Vision Research. There were at least three experiments for statistical analyses and investigators who conducted analysis were masked as to the treatment groups. All the mice were cared for by following the ACUC protocol approved by the Institutional Animal Care and Use Committee at Schepens Eye Research Institute.

Major Reagents

Antibodies against VEGFR2 (1:1000 for western blot) and β-Actin (1:5000 for western blot) were purchased from Cell Signaling Technology (Danvers, Mass.) and Santa Cruz Biotechnology (Santa Cruz, Calif.), respectively. Horseradish peroxidase (HRP)-conjugated goat anti-rabbit IgG (1:5000) and anti-mouse IgG (1:5000) were from Santa Cruz Biotechnology (Santa Cruz, Calif.). Enhanced chemiluminescent substrate for detection of HRP was from ThermoFisher Scientific (Waltham, Mass.). Alexa fluorescence-594-conjugated mouse endothelial specific isolectin B4 (IB4) was purchased from Life Technology (Grand Island, N.Y.). The plasmids of pAAV-pMecp2-SpCas9-spA (AAV-SpCas9)(Cat. 60957) and pAAV-U6-sgRNA(SapI)-hSyn-GFP-KASH-bGH (SpGuide acceptor)(Cat. 60958) were purchased from Addgene (Cambridge, Mass.). High-fidelity Herculase II DNA polymerases were from Agilent Technologies (Santa Clara, Calif.).

Cell Culture

C57BL/6 mouse primary brain microvascular endothelial cells (MVECs) were purchased from CellBiologics (Catalog number: C57-C57-6023, Chicago, Ill.) and cultured in the endothelial cell medium with a kit (CellBiologics). Human primary retinal microvascular endothelial cells (HRECs) were purchased from Cell Systems (Catalog number: ACBR1 181V, Kirkland, Wash.) and cultured in Endothelial Growth Medium (EGM)-2 (Lonza, Walkersville, Md.). Primary human umbilical vein endothelial cells (HUVECs, Catalog number: CC-2517) and human primary retinal pigment epithelial cells (hPRPE, Catalog number:194987) were purchased from Lonza. HUVECs were cultured in Medium 199 (Sigma) supplemented with 20% bovine calf serum (BCS; HyClone, Logan, Utah), 100 mg/ml heparin, 12 mg/ml bovine brain extract (BBE; Hammond Cell Tech, Windsor, Calif.). hPRPE cells were cultured in a 1:1 mixture of low-glucose Dulbecco's modified Eagle's medium (DMEM; Life Technologies, Grand Island, N.Y.) and Ham's F-12 Nutrient Mixture (Gibco) supplemented with 10% fetal bovine serum (FBS; Lonza, Walkersville, Md.). Tissue culture dishes were pre-coated with 0.2% gelatin in phosphate buffered saline for MVECs, HRECs and HUVECs [35]. All cells were cultured at 37° C. in a humidified 5% $CO_2$ atmosphere [36].

DNA Constructs

The 20nt target DNA sequence (5'-GTCCCGGTACGAGCACTTGT-3', mK22 (SEQ ID NO:1)) preceding a 5'-NGG PAM sequence at exon 3 in the mouse VEGFR2 genomic locus (NC_000071.6) was selected for generating single guide RNA (sgRNA) for SpCas9 using the CRISPR design tool. The control sgRNA sequence (5'-TGCGAATACGCCCACGCGATGGG-3' (SEQ ID NO:2)) was designed to target the lacZ gene of *Escherichia coli*[16]. The pAAV-U6-sgRNA-CMV-GFP vector (V1) was originated from AAV-SpCas9 (Cat. 60958) [16] by replacing the hSyn-GFP with the PCR amplified CMV-GFP from pEGFP-C1 vector (Clontech, Cat. 6084-1) using XbaI/EcoRI as described previously [15]. The pAAV-pICAM2-SpCas9 (V3) was derived from AAV-SpGuide (Cat. 60957) by replacement of the promoter pMecp2 using XbaI/AgeI with pICAM2, which was PCR amplified from genomic DNA isolated from HRECs. The PCR primers for this amplification were: forward 5' CGTCTAGAGTAGAACGAGCTGGTGCACGTGGC-3' (SEQ ID NO:3), reverse 5'-GGACCGGTC-CAAGGGCTGCCTGGAGGGAG-3' (SEQ ID NO:4). All these constructs were confirmed by DNA sequencing.

To construct SpGuides, the top oligo 5' ACC-GTCCCGGTACGAGCACTTGT) (SEQ ID NO:5) and bottom oligo: 5'-AAC-20nt-C-3'(20nt: complimentary target mK22 DNA sequences) were annealed and cloned into the V3 vector by SapI. All clones were confirmed by DNA sequencing using a primer 5'-GGACTATCATATGCT-TACCG-3' (SEQ ID NO:6) from the sequence of U6 promoter, which drives expression of sgRNAs.

Production of Adeno-Associated Virus

The recombinant AAV2/1 (rAAV1) vectors were produced as described previously [17] in the Gene Transfer Vector Core in Schepens Eye Research Institute of Massachusetts Eye and Ear (Boston, Mass.). Briefly, triple transfection of AAV package plasmid (AAV2/1), transgene plasmid (pAAV-pICAM2-SpCas9: AAV-SpCas9, pAAV-U6-mK22-CMV-GFP: AAV-mK22 or pAAV-U6-lacZ-CMV-GFP: AAV-lacZ) and adenovirus helper plasmid were performed in a 10-layer hyper flask containing confluent HEK 293 cells. At day three post transfection, the cells and culture medium were harvested and enzymatically treated with Benzonase (EMD Millipore). After high speed centrifugation and filtration, the cell debris was cleared. The viral solution was concentrated by running through tangential flow filtration, and then loaded onto an iodixional gradient column. After one round of ultracentrifugation, the pure vectors were separated and extracted, then ran through an Amicon Ultra-Centrifugal Filter device (EMD Millipore) for desalting. Both vectors were titrated by TaqMan PCR amplification (Applied Biosystems 7500, Life Technologies), with the primers and probes detecting the transgene. Sodium dodecyl sulfate-polyacrylamid gel electrophoresis (SDS-PAGE) was performed to check the purity of the vectors, which were named rAAV1-SpCas9, rAAV1-mK22, and rAAV1-lacZ.

Transduction of Cultured Cells

MVECs, HRECs, HUVECs and hPRPE cells grown to 50% confluence in a 48-well plate were changed into the fresh cultured media and added either with rAAV1-mK22, rAAV1-lacZ, rAAV1-SpCas9 individually or both of rAAV1-SpCas9 with rAAV1-mK22 or rAAV1-lacZ [2 μl/well for each rAAV1, $3.75 \times 10^{12}$ viral genome-containing particles (vg)/ml]. Three days later, the cells were photographed under an immunofluorescence microscope for determining the rAAV1 transduction efficiency. After four days, the cells were lysed with 1×sample buffer for western blotting analysis or harvested for genomic DNA isolation.

Western Blot

Cells were lysed in 1×sample buffer, which was diluted with extraction buffer (10 mM Tris-HCl, pH 7.4, 5 mM EDTA, 50 mM NaCl, 50 mM NaF, 1% Triton X-100, 20 μg/mL aprotinin, 2 mM $Na_3VO_4$, and 1 mM phenylmethylsulfonyl fluoride) from the 5×protein sample buffer (25 mM EDTA (pH=7.0), 10% sodium dodecyl sulfate (SDS), 500 mM dithiothreitol, 50% sucrose, 500 mM Tris HCl (pH=6.8), and 0.5% bromophenol blue). The lysates were boiled for five minutes and then centrifuged for 5 minutes at 13,000×g. Proteins from the samples were separated by 10% SDS polyacrylamide gel electrophoresis (PAGE), transferred to polyvinylidene difluoride membranes, and subjected to western blot analysis. Experiments were repeated at least three times. Signal intensity was determined by densitometry using NIH ImageJ software [36].

DNA Sequencing

Cells were harvested for genomic DNA extraction using the QuickExtract DNA Extraction Solution (Epicenter, Chicago, Ill.), following the manufacturer's protocol. In brief, the pelleted cells were re-suspended in the QuickExtract solution, vortexed for 15 seconds, incubated at 65° C. for six minutes, vortexed for 15 seconds and then incubated at 98° C. for 10 minutes. The genomic region around the PAM was PCR amplified with high-fidelity Herculase II DNA polymerases. The PCR primers were (forward 5'-GCTCCTGTCGGGTCCCAAGG-3' (SEQ ID NO:7)) and (reverse 5'-ACCTGGACTGGCTTTGGCCC-3' (SEQ ID NO:8)). The PCR products were separated in 2% agarose gel and purified with a gel extraction kit (Thermo Scientific) for Sanger DNA sequencing and NGS [15]. DNA sequencing was performed by the MGH DNA core facility.

A Mouse Model of Oxygen-Induced Retinopathy

C57BL/6J litters on postnatal day (P) 7 were exposed to 75% oxygen until P12 in the oxygen chamber (Biospherix). Oxygen concentration was monitored daily using an oxygen sensor (Advanced Instruments, GPR-20F)[23, 37]. On P12, the pups were anesthetized by intraperitoneal injection of 50 mg/kg ketamine hydrochloride and 10 mg/kg xylazine. During intravitreal injections, eyelids of P12 pups were separated by incision. Pupils were dilated using a drop of 1% tropicamide and the eyes were treated with topical proparacaine anesthesia. Intravitreous injections were performed under a microsurgical microscope using glass pipettes with a diameter of approximately 150 µm at the tip after the eye were punctured at the upper nasal limbus using a BD insulin syringe with the BD ultra-fine needle. One µl of rAAV1-CMV-GFP or both of rAAV1-SpCas9 with rAAV1-mK22 or rAAV1-lacZ (1 µl, $3.75 \times 10^{12}$ vg/ml) was injected. After the intravitreal injection, the eyes were treated with a triple antibiotic (Neo/Poly/Bac) ointment and kept in room air (21% oxygen). On P17, the mice were euthanized and retinas were carefully removed and fixed in 3.7% paraformaldehyde (PFA), and the mice under 6 g were excluded from the experiments. In total there were six experiments performed in this OIR model. Retinal whole mounts were stained overnight at 4° C. with murine-specific EC marker isolectin 4 (IB4)-Alexa 594 (red) [23, 38, 39]. The images were taken with an EVOS FL Auto microscope (Life Technologies).

Quantification of Vaso-Obliteration and NV

This was performed previously [23]. Briefly, retinal image was imported into Adobe Photoshop CS4, and the Polygonal Lasso tool was used to trace the vascular area of the entire retina. Once the vascular area was highlighted, the number of pixels was obtained. After selecting total retinal area, the Lasso tool and the 'subtract from selection' icon to was used to selectively remove the vascularized retina, leaving behind only the avascular area. Once the avascular region was selected, click the refresh icon again to obtain the number of pixels in the avascular area.

When analyzing NV, the original image was reopened. The magic wand tool was selected from the side tool panel on the left side of the screen. On the top tool panel, the tolerance to a level that will pick up NV was set while excluding normal vessels (beginning at 50). Regions of NV were selected by clicking on them with the magic wand tool. The areas of NV fluoresced more intensely than surrounding normal vessels. When neovessels were selected, the area of interest was zoomed in by holding the 'Alt' key on the keyboard and scrolling up. When all NV was selected and checked, the refresh icon and record the total number of pixels clicked in the NV area.

Laser-Induced Choroid Neovascularization in Mice

Ten mice (Stock number: 664, C57BL/6J, male and female, 17-22 g, 6-8 weeks old, Jackson Laboratories, Bar Harbor, Me.) were deeply anesthetized with an intraperitoneal injection of ketamine/xylazine (120 mg/kg Ketamine/20 mg/kg Xylazine). Their pupils were be dilated using a drop of 1% tropicamide and the eye were treated with topical proparacaine anesthesia drops. The mice were placed on a specialized stage with the Micron III retina imaging system (Phoenix Research Labs, Pleasanton, Calif.) using Genteal gel (Novartis, Basel, Switzerland). Under real-time observation, laser photocoagulation were applied to the eyes using a Streampix5 laser system (Meridian AG, Zürich, Switzerland) at 532 nm wavelength (100 µm of diameter, 0.1s of duration and 100 mW of power). Four lesions located at the 3, 6, 9, and 12 o'clock meridians around the optic nerve were induced. Laser-induced disruption of Bruch's membrane was identified by the appearance of a bubble at the site of photocoagulation. Fundus images were taken on the anesthetized mice using the Micron III retina imaging system with illumina light. Laser spots that did not result in the formation of a bubble were excluded from the studies. Laser spots were also be confirmed by optical coherence tomography (OCT)[24, 40]. rAAV1 (1 µl, $3.75 \times 10^{12}$ vg/ml) was injected into the vitreous using glass pipettes with fine tips after puncturing the sclera 1 mm from the limbus with a 30-gauge needle under an operation surgical microscope. On day seven or 14, animals were anesthetized as described above. Fundus images were taken using the Micron III retina imaging system with illumina light. Then 0.01 ml of 25% sodium fluorescein (pharmaceutical grade sodium fluorescein; Akorn Inc) per 5 g body weight was injected intraperitoneally. The retinal vasculature filled with dye in less than one minute following injection. Images of fluorescein angiography were taken with UV light sequentially at two and five minutes post fluorescein injection. Seven days after rAAV1 injection the mice were euthanized, and the mouse eyes were carefully removed and fixed in 3.7% paraformaldehyde (PFA). Whole-mount choroids were stained overnight at 4° C. with IB4 [23, 38, 39]. The images were taken with an EVOS FL Auto microscope.

NGS Analysis of Potential Off-Targets

To find potential off-targets for the mK22-targeted genes, the "CRISPR Design Tool" (crispr.mit.edu/) was used[16], indicating that the most potential off target sequence was CTCACGGTTGGAGCACTTGTAGG (SEQ ID NO:9) that was located at Chr7:-126856352. Based on this information, we designed PCR primers (forward primer P25F: AGCTTCATTCAGTGTCTCTGGG (SEQ ID NO:10), reverse primer P25R: GGGTATTTGTAAGGTGCTGTTGA (SEQ ID NO:11)) for PCR amplification of the DNA fragment covering the potential mK22 off targets. The PCR products from MVECs transduced by the dual AAV-CRISPR/Cas9 vectors either containing lacZ-sgRNA or VEGFR2-sgRNA (mK22) were sent for Sanger DNA sequencing and NGS.

Examination of Toxicity of the Dual AAV-CRISPR/Cas9 in Mouse Eyes

On P12, five pups were anesthetized and underwent intravitreal injections as described above. During injection, One µl of rAAV1-SpCas9 plus rAAV1-mK22 was injected.

After 4 weeks, optical coherence tomography (OCT) was performed using an spectral domain (SD-) OCT system (Bioptigen Inc., Durham, N.C.). Briefly, mice were deeply anesthetized with an intraperitoneal injection of ketamine/xylazine (100-200 mg/kg Ketamine/20 mg/kg Xylazine). The pupils were dilated with topical 1% Tropicamide to view the fundus. After anesthesia, Genteal gel was applied to both eyes to prevent drying of the cornea. The fundus camera in the optical head of the apparatus provided initial alignment for the sample light, to ensure it is delivered through the dilated pupil. Final alignment was guided by monitoring and optimizing the real time OCT image of the retina, with the whole set up procedure taking approximately 5 minutes for each mouse eye.

At week 4, after OCT, electroretinography (ERG) (by light/dark adaptation, using a DIAGNOSYS ColorDome containing an interior stimulator) was performed as followed. Following overnight dark adaptation, the animals were prepared for ERG recording under dim red light. While under anesthesia with a mixture of Ketamine (100-200 mg/kg i.p.) and Xylazine (20 mg/kg i.p.), their pupils were dilated using a drop of 1% Tropicamide followed by a drop of 1% Cyclopentolate hydrochloride applied on the corneal surface. One drop of Genteal (corneal lubricant) was applied to the cornea of the untreated eye to prevent dehydratation. A drop of 0.9% sterile saline was applied on the cornea of the treated eye to prevent dehydration and to allow electrical contact with the recording electrode (gold wire loop). A 25-gauge platinum needle, inserted subcutaneously in the forehead, served as reference electrode, while a needle inserted subcutaneously near the tail served as the ground electrode. A series of flash intensities was produced by a Ganzfeld controled by the Diagnosys Espion 3 to test both scotopic and photopic response.

The following day after ERG, fluorescein fundus angiography (FFA) was performed on the mice. Animals were anesthetized with a mixture of Ketamine (100-200 mg/kg i.p) and Xylazine (20 mg/kg i.p), and their pupils were dilated using a drop of 1% Tropicamide and the eye will be treated with topic anesthesia (Proparacaine drops). A drop of sterile saline was placed on the experimental eye to remove any debris followed by Genteal. Genteal was placed on both eyes to prevent corneal drying. Then 0.01 ml of 25% sodium fluorescein (pharmaceutical grade sodium fluorescein; Akorn Inc) 5 g body weight was injected i.p. The retinal vasculature was filled with dye in less than one minute following injection. Photos were taken sequentially at 1, 2, 3, 4, and 5 minutes post fluorescein injection. A Micron III (Phoenix Research) system was used for taking fundus photographs according to manufacturers instructions. The mice were placed in front of the Fundus camera and pictures of the retina taken for monitoring retinal function.

After the mice were euthanized, retinas were carefully removed and fixed in 3.7% paraformaldehyde (PFA). Retinal whole mounts were stained overnight at 4° C. with murine-specific EC marker isolectin 4 (IB4)-Alexa 594 (red) [23, 38, 39]. The images were taken with an EVOS FL Auto microscope (Life Technologies).

Statistics

The data from three independent experiments in which the variance was similar between the groups were analyzed using an unpaired and two tailored t test. For animal experiments at least the data from six mice were used for the statistic analysis. P values of less than 0.05 were considered statistically significant. All relevant data are available from the authors.

Example 1. CRISPR/Cas9-Mediated Depletion of VEGFR2 in Vascular ECs in Vitro

Recombinant AAV (rAAV) vectors are at present the leading candidates for virus-based gene therapy thanks to their broad tissue tropism, non-pathogenic nature and low immunogenicity [13]. In this study, we adapted a dual-AAV vector system packaging SpCas9 and SpGuide [16]. To identify an appropriate AAV serotype that could transduce vascular endothelial cells (ECs), we replaced the GFP promoter (phSyn) in the AAV-SpGuide vector [16] with a promoter of cytomegalovirus (CMV) [FIG. 1A] [15].

Figure 5:
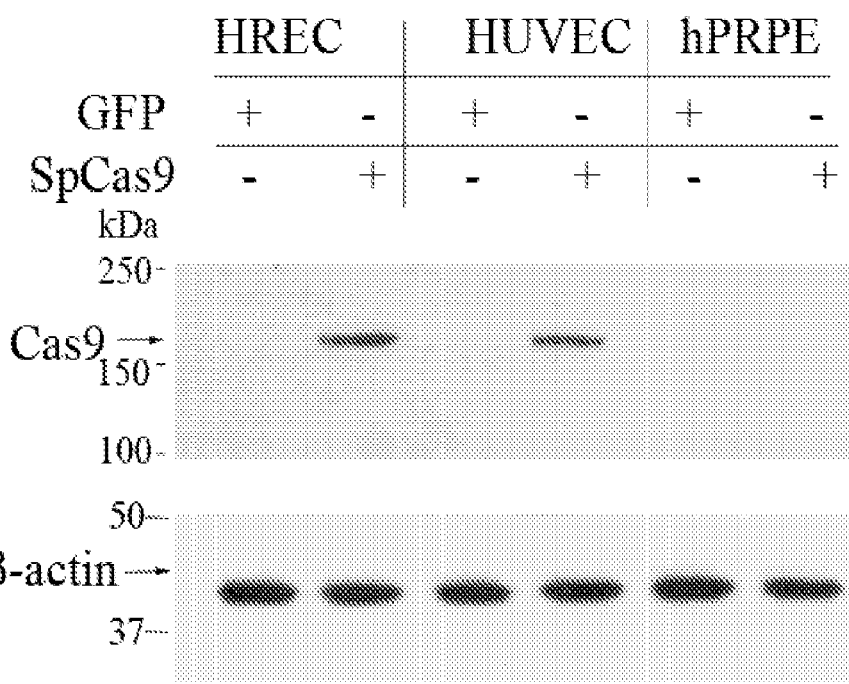
FIG. 5. pICAM2-driven expression of SpCas9 in ECs. As described in FIG. 1, after transduction with rAAV1-CMV-GFP (GFP) or rAAV1-pICAM2-SpCas9 (SpCas9) (2 µl/well, 3.75×10$^{12}$ vg/ml) in a 48-well plate for four days, cell lysates were subjected to western blot analysis with antibodies against Cas9 and β-actin. Data shown are representative of three independent experiments. kDa:kilodalton. HREC: human retinal microvascular endothelial cells, HUVEC: human umbilical vein cells, hPRPE: human primary retinal pigment epithelial cells.

A major goal of gene therapy is the introduction of genes of interest into desired cell types. To circumvent targeting VEGFR2 in photoreceptors of eye tissues [18], an endothelial specific promoter is designed to drive expression of SpCas9. Thus, we substituted the Mecp2 promoter in the AAV-pMecp2-SpCas9 vector [16] for an endothelial specific promoter of intercellular adhesion molecule 2 (pICAM2) [19] (FIG. 1B).

rAAV1 has been shown to transduce vascular ECs in high efficiency [20]. We next examined whether rAAV1 was able to deliver the CRISPR-Cas9 into ECs [20, 21]. As shown in FIG. 1C, rAAV1 was able to infect human primary retinal microvascular ECs (HRECs), human primary umbilical vein ECs (HUVECs) as well as human primary retinal pigment epithelial cells (hPRPE). Subsequently, we transduced these cells with rAAV1-pICAM2-SpCas9 (rAAV1-SpCas9) for testing if the ICAM2 promoter was able to drive SpCas9 expression in ECs specifically. Western blot analysis of the transduced cell lysates indicated that SpCas9 was expressed in HRECs and HUVECs, but not in hPRPE cells (FIG. 1D and FIG. 5), demonstrating that the dual vectors of AAV-SpCas9 and AAV-SpGuide are able to specifically target genomic loci of ECs. Then, a target mouse genomic sequence named as mK22 (FIG. 1A) corresponding to the most efficient sgRNA targeting human VEGFR2 exon 3 named as K12 among the four target sequences[22] was cloned into the SpGuide vector.

Figure 6:
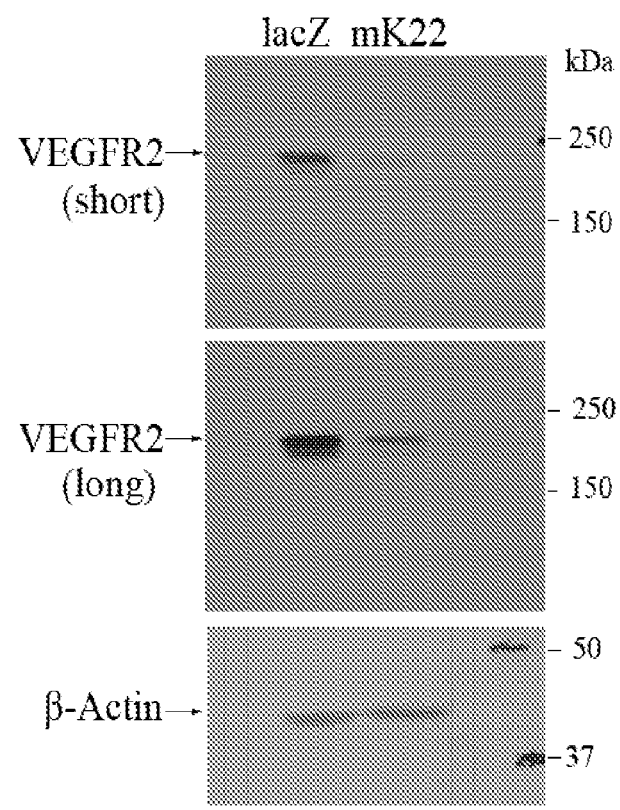
FIG. 6. Depletion of VEGFR2 expression using AAV-CRISPR/Cas9. Total cell lysates from the transduced MVECs (mouse primary brain vascular endothelial cells) were subjected to western blot analysis with antibodies against VEGFR2 (short: short exposure, long: long exposure) and β-actin. Data shown are representative of three independent experiments. lacZ: lacZ-sgRNA as a negative control, mK22: VEGFR2-sgRNA.

To assess the editing efficiency of our dual-vector system in vitro, we infected C57BL/6 mouse primary brain microvascular ECs (MVECs) using rAAV1-SpCas9 with rAAV1-mK22 or rAAV1-lacZ. After four days post infection, the genomic DNA was isolated for PCR. Sanger DNA sequencing results showed that there were mutations around the PAM sequence of PCR products from MVECs transduced with rAAV1-SpCas9 plus-mK22 but not from those with rAAV1-SpCas9 plus-lacZ (FIG. 1E), suggesting that the mK22-guided SpCas9 cleaved the VEGFR2 locus at the expected site in MVECs. To find potential off-targets for the mK22-targeted genes, the "CRISPR Design Tool" (crispr.mit.edu/) was used. NGS analysis indicated that mK22 did not influence on the most possible off target sequence in MVECs. Western blot analysis of the transduced cell lysates indicated that there was an 80% decrease in VEGFR2 from the transduced MVECs with SpCas9/mK22 compared with those with SpCas9/lacZ (FIG. 1F and FIG. 6), demonstrating that the AAV-CRISRP/Cas9 system with mK22 efficiently and specifically induced mutations within the VEGFR2 locus and subsequent protein depletion in MVECs in vitro.

Example 2. Transduction of ECs with rAAV1 In Vivo

Gene delivery to the vasculature has significant potential as a therapeutic strategy for several cardiovascular disorders including atherosclerosis and angiogenesis. However, there is a pronounced challenge in achieving successful vascular ECs gene transfer in vivo. To determine if rAAV1 was capable of transducing vascular ECs of NV in the C57BL/6 mouse models of OIR [23] and laser-induced CNV [24], we intravitreally injected rAAV1-CMV-GFP into mouse eyes at post-natal day 12 (P12) with or without experiencing the OIR model and immediately after the post-laser injury to Bruch's membranes of six-week-old mice in the CNV model, respectively. Whole mount retinas of the P17 mice from the OIR model and the whole mount choroids of the mice at day 7 after injection from the CNV model were stained with mouse endothelial specific marker isolectin 4 (IB4)-Alexa 594. The merged images of IB4 with GFP indicated that rAAV1 was able to transduce normal vascular ECs in the retinal (FIG. 7) and that preferentially transduced vascular ECs of NV induced by hypoxia and laser injury in the OIR (FIG. 2 and FIGS. 8A-C to 9A-G) and CNV models (FIG. 2 and FIGS. 10A-F), respectively.

Example 3. Editing Genomic VEGFR2 Abrogated Hypoxia-Induced Angiogenesis

To investigate whether the dual AAV system of AAV-SpCas9 and AAV-SpGuide (mK22) was able to edit VEGFR2 and inhibit pathological angiogenesis in vivo, we intravitreally injected equal amount of rAAV1-SpCas9 and rAAV1-mK22 or rAAV1-lacZ into P12 mouse eyes in the OIR mouse model [23]. In this model, P7 mouse pups with nursing mothers are subjected to hyperoxia (75% oxygen) for 5 days, which inhibits retinal vessel growth and causes significant vessel loss. On P12, mice are returned to room air and the hypoxic avascular retina triggers both normal vessel regrowth and retinal NV named as preretinal tufts, which is maximal at P17[23]. Thus, on P17 the whole mount retinas were stained with IB4. The results (FIGS. 3A-C and FIGS. 11A-L) showed that there was a dramatic decrease in the number of preretinal tufts and significantly more avascular areas from mice injected with rAAV1-SpCas9/mK22 than those with rAAV1-SpCas9/lacZ, suggesting that genome editing of VEGFR2 by SpCas9/mK22 inhibits retinal NV in this OIR mouse model. Next generation sequencing results (FIG. 3D) confirmed that there was about 2% insertion/deletions (indels) around the PAM from genomic DNA of the retinas treated with AAV-SpCas9/mK22, but none with AAV-SpCas9/lacZ. In addition, western blot analysis of the retinal lysates showed that there was an about 30% reduction in VEGFR2 from mice treated with rAAV1-SpCas9/mK22 compared with controls (FIGS. 3E & F and FIG. 12). Taken together, these data demonstrate that editing genomic VEGFR2 locus with SpCas9/mK22 abrogates hypoxia-induced angiogenesis in this OIR mouse model. In addition, the intravitreal injection of SpCas9/mK22 did not cause detectable damage to the retina morphology and function examined by optical coherence tomography (OCT), electroretinography (ERG), fluorescein fundus angiography (FFA) and whole-mounted retina staining by IB4 at the time point of four-weeks (FIGS. 13A-D).

Example 4. AAV-CRISPR/Cas9 Targeting Genomic VEGFR2 Suppressed NV in Laser-Induced Choroid NV in Mice We also assessed whether the rAAV1-SpCas9/mK22 could inhibit NV in the laser-injury-induced CNV mouse model, which has been used extensively in studies of the exudative form of human AMD [24]. First, we intravitreally injected rAAV1-SpCas9 with rAAV1-mK22 or rAAV1-lacZ into mouse eyes following the laser injury. In this model, NV grows from choroid vessels after laser injury on Bruch's membrane, and on day seven there is the maximal CNV, which begins to regress spontaneously after 14-21 days [24]. Hence, on day seven, fluorescein was injected into the mice intraperitoneally, and images of fluorescein angiography (FA) were taken. Subsequently, the flat-mount choroids were stained by IB4 for analysis of laser-injury-induced CNV. As shown in FIG. 4A-C, there was less NV in the eyes injected with rAAV1-SpCas9/mK22 than those with rAAV1-SpCas9/lacZ on day seven.

To examine if editing genomic VEGFR2 could promote regression of CNV, rAAV1s were intravitreally injected on day seven in the mouse CNV. On day 14, the images of FA and IB4 staining showed that there was less CNV from the mice injected with rAAV1-SpCas9/mK22 than those with rAAV1-SpCas9/lacZ (FIG. 4D-F). These data indicate that editing the genomic VEGFR2 locus with SpCas9/mK22 suppresses NV in this laser-injury-induced CNV model. Taken together, our data establish a strong foundation for genome editing as a novel therapeutic approach to angiogenesis-associated diseases.

```
>NG_012004.1:5001-52337 Homo sapiens kinase insert domain
receptor (KDP), RefSeqGene on chromosome 4
                                                         (SEQ ID NO: 12)
ACTGAGTCCCGGGACCCCGGGAGAGCGGTCAATGTGTGGTCGCTGCGTTTCCTCTGCCTGCGCCGGGCA

TCACTTGCGCGCCGCAGAAAGTCCGTCTGGCAGCCTGGATATCCTCTCCTACCGGCACCCGCAGACGCC

CCTGCAGCCGCGGTCGGCGCCCGGGCTCCCTAGCCCTGTGCGCTCAACTGTCCTGCGCTGCGGGGTGCC

GCGAGTTCCACCTCCGCGCCTCCTTCTCTAGACAGGCGCTGGGAGAAAGAACCGGCTCCCGAGTTCTGG

GCATTTCGCCCGGCTCGAGGTGCAGGATGCAGAGCAAGGTGCTGCTGGCCGTCGCCCTGTGGCTCTGCG

TGGAGACCCGGGCCGCCTCTGTGGGTAAGGAGCCCACTCTGGAGGAGGAAGGCAGACAGGTCGGGTGAG

GGCGGAGAGGACCTGAAAGCCAGATCTAACTCGGAATCGTAGAGCTGGAGAGTTGGACAGGACTTGACA

TTTTGCGATCTTTCATTTACCAGTGGGGAAACTGAGGCTCAGAGACTGGCCCAAGATTACCCAGCGAGT

CTGTGGTCGCCTGTGCTCTAGCCCAGTTCCTTTTCTAGGACTCTGGTTTGCGACAGGGACCTCGGCTGG

AGCATGTCCTGAGATGCCGACACACCCTCAGGCTCTTGGGAGGCTGGGGTGGGAAGGCGCCTGGGGTTG

GCAGGCAGGAGGTGCCTCCGCAGGCGAGAACAGGCGGTGAAAAGTTGTCTGGCTGCGCGCAACATCCTA

GTCCGGGCCCGGGGAAGAAAACCTTGCCGGAATCTCAGGCCGGGTCTCCCGGATCGGACGGTACACTCG

GTTCTGCCTCTTTGCGGGACCCGGCCCGTTGTTGTCTTCATGCTCGAACACACTTGCACACCACTGTGT

GAAGTGGGGTCTGGAGCGGAGAGAAACTTTTTTTCCTTCCTTGGTGCAGGACGCCGCTCTCCTTGCAGA
```

-continued

```
GCGAAGAAGGGGGGGAATAGGGACTTGTCCTGGGGGCTTTGACAGCTTCCCCAAGGGTCTCCAAGTAAC

AGCCAACTGTCCTGCGTAAAGCATTGCACATCTTTCAAAGCGCTGTGGTCCTTGGTGTAAGCGCATAGT

CAGAAGTTCAAGCTCCGAAAACCTTTCCTGTGGGCCTTGGTACCTAGCTTTAGTGCCATTCCTTCCTCT

CCCTGCCGCCTAAAATTTCCGTCTCCTTCAATTAGGAACACACACGTTCTTCATGCAATAGCTGTCTGT

CTTTTCTTCCTCACTTTCCTTTCTCTCTCAACCCCTTAGATAATATTTCTTTCCTGCAGCCAGTTTGCT

GATATCCAGATTTCCACCCTTTGCAGGGTGAGAAAGGGGAAAGGGTCAGAGAAAGAAAAAAAAAAAGTC

GAATAATTCAGGGAAAAAAATTTCTTACTCCCTAAGACAAGAATCACATGTCTTAGAAGACACTCACAC

CCACATACAGTACCAGGATCATCTGTCCATGGTTACTGAATTTTCTTTATAATGACTTGGTTCAACGGG

TCCAGTCCACCATGGACACTCATTTGTCCCAGACAAGCCCTCTCTCTCCCCCTTTCTGGGCAGAGAATG

AAGGTCTGGAACATGTGGTTGCTCTGTATTCCACAAAGAAGTGAGTTGCTTTTAAGCCTGGGGTGTTTC

CTAGCGTAGTAGTAACGGCAGGCCGGTCGCCCTGAATATAATGGTGAACTTGCCCTTTTGGAGTGCATT

ACTTGCTTAATTGGATTGGGCTGTAATTGGTGCCATCAAATTCTAGAGACAGAGGCACTGTTGTTTTTC

CTTCCCGTCTTTGAGCTGGAAGGGTAACAGTGCACAAATTAATTAATATTGGTTATGGGATTTGAACAT

AGAAGGGCTTTTTATTGAGTAGTAGCATGTGTACCTCTTACAGTTATTTCTTTAGAACTTTCTGAAGAG

TCCAGCTCAAGCTTGCCAATGAAAACGAATGACATTTAATGGAGCAAAAACAAAAAACAAAAAACTATG

TTGGTCTACAAATATGAATTTGAAGTTATTGAGAGCCTTGTTGAATAGATTTTTGTTGTAAACGTGTCT

CTAGAATAGTATGGCATAGTCTCAGCTTCCTATGAATGAAGGACATACCTTTTCTTTTTTAAAATATTT

GTTACACAGGAAAGTGTGTCTAGAATGTGATCTGTGGCAATAAATTATGAGAGACCTTCAAGAGTTTCT

GATTTTGGTAGCCGAGTGGGCACAGTTTATTGAGAATCATTTTTACTGCCATTTGTTTTCTCACAAGAA

TGTGCCCAAATAATGGTTTTTTTCTCATTTGGATGGCAGTGTGAATTGTACATCATGTTTTCAGCATCT

TTCTCAACCTAGTGTTCCCCAGTCAAGTTTGAAATCTGTGTTATCCAAATGAATTGTTTTCATTTTCCT

TTTCTTAGACAAAGTGGGACTCCAGGTTTCATTTTGCTTTTAAACATTTTGGTTTTTTGTTTGCCTGTT

TTGGGGGCAGTTATTTCTTTCATATTAAAAAGTACTGTGCAGGCTGGGTGCAGTGGCTCATTCCTGTAA

TCCCAGCACTTAGGGAAGCAGAGGCAGGAGGATCGCTTGAGTCCAGGAGTTCAAGAAGTGCCTGGGCAA

CATAGCGAGACCCCATTCTCTATTTAAAACATAAATGTAACCCCCGTTCCACGCACAAAGTACTGTGCA

AATTAATTAAACATGACCACCCAGACCAGCAACTGTCCAAGAGTGGCCCATAGACCATCTGTGGTAGGA

TAATTTGAAATGCTTGTTAAAATGCAGATTTGTAGACCCAGGGATATTCTGACAGAGTCTAAAGTCTTA

AGAACAAAACTGTTCTAAACATAAGTCAGTACCAATGCCAGTTAATTTCTGAGATATATTGATATAACT

TAGTTTCCAGTTTTTTAAAAACCATATTATTGACTTAAAAACCATGATATTGACCAGTTATGTCAGTAA

CTTATTTTGCACATCTGTGTGGTGTGTGAGAACATGTGCAGTCACTTATTCATTTTGCCTGCATTTGTT

CATATTGGGATCCTCAGATTCAATGCACTGGATGTTTGCACTGGGTATTTACTTATACTCTCTCTATTT

ATTCCGTCTCATACTTCGTCCTATTTGTTCATACTCTCTTATTTGCCCAGCAAGGTCAATGCCAGTTTA

GGCCTAGGGAGTCATTTTTTCTTAGTTGATATGACTTAGAAAGCTTGGGAGCCTGCCCAACATCAATTA

GTAGAGTGACCCATGGTGAGGAATCTATGCCATGGTACTTTTCTGGTTCTTATCCCTTATAGGTAAAGA

CAAGTTTCTTATGTCTGAAGCTTGATGTCAGGATGAGTTCAGGGCTTTGATGAATAAGTTCAGATCTCC

CAATTGTAATTCATTAGCATTGCACTTAAAAAAATTTATATACGTTTTTAAAAAAGGGTAATGCTAATG

AATTACAATAGAGAGAAAGTACATTAGTTTGCATGTATGTGTGAAACTGGGAAAATTTTTCACGAAAA

TATTCATATACTTTTTAAAAAAAGGGTAATGCTAATGAATTACAGTAGACAGAAAAGTATATTAATTTG

CACATATGTGTAAAATTGGGAAAATTCCACACATACATAAAGTATATTAATATGCATGTATGTGTGGA

ATTGGGGAATGTTTTCTCTTCCTCAGTTTCTCTCCCTTGCTTTTAATGTACAGTCTTTATGAGCCATTA

TTTCAGCTGTGGCAGTTTGGTTACCAGGGGAAGCGCACTAGAAAATTGATAAAGGAAAATGAGACAAGG
```

-continued

```
TCATAGATTCTCTCACTCCCTTCAGGGTACGTAGATGAACTATATAAAAATCCGTCTAAGTGGGATTCG

TTAATCAGCAATTTAGTCAAATGTGTACATCCTATGTTCTATAAGAAATGTCAGTGGGTCCTTTCCCAA

GGGAGTGAGATCATCAGATGAAGGTTCATTTGGTTTCAATGTCCCGTATCCTTTTGTAAGACCTTGAAG

TTGGCAATGCAGGAAAACAGGAACTCCACCCTAGCTCCATGAATTGCAGAACTGTTGTGTTGGTTTATG

ACCATCTGCCCATTCTTCCTGTTATGACACAGCTTGTGAACTTTTACTGAGAATGGTGAAAAGTAAATT

CCCAGTTTTATACAATGAATTGCTGAAGAGGCCTTTTAAAGTATAGAGTATGCATTGTTTATGGAAGGT

GTTTCCTATTAGGTCTAACTCAGTGGCAACTACATTCATTTATTTAATTTGTTTCTAGGTTTGCCTAGT

GTTTCTCTTGATCTGCCCAGGCTCAGCATACAAAAAGACATACTTACAATTAAGGCTAATACAACTCTT

CAAATTACTTGCAGGTAAGGATTCATTCTAGATCTAGATTTCTTGTGTTAAGTAACTGATTGTTTATTG

AGTGGAAATAATTTCCAGTAGAGCAGAATTATAATAGAGCTTGTAGTAATTGTTCATAAGTGGTGAGGT

TTCTAAGAACTGATGTAATAATGGAAAATGAGAAGAATTTTCTCTCAAAAATTCTGTACAATTTTGCTG

GTGTTTTATACTATTCTCTGCCAACATGCATACACACACACACACACACACGCACACAAATACACACC

CACACCCACATTCCAATAACCAGTACAGCCACCTGGCGTATAGTAGACATACGCTCAATAAATATGAAT

GAATAAATGAAGTTGAGGGCATACATTTAAGGAATAGAGTTGAAAAAATTTGGGACTATATTTATTATG

CTTGGTATGATTCTTGAACACTTATTATCCCTTTCCAAAAACTTTGCTTTATAAGAAATTTATTACTAT

AATTACTTAGGCAGTAATATTTAATAGCAATTTAATATTTAGTGGGTAATATTACTGAGCGCATGATCT

ACATAAATAATGGACTTCGGGCCCTGCCTTGATATTCTGGAATGCATCTTTCCCCACTTGCTAGCAAGA

AGTCATGCTATTGATTTTTGATAACTGGAGAAGTAGACTTCTTTGTCAAGAAGAAGAGGCCTTTAAATT

TTGCCTTTCAACCCTTACCCCAGGACGAAAGATAGAAGACCCTTGGGTTTAACATAGTGATCACACACG

AAAGGCATGGAGCCTTCTTAGGACCTGTGTGTTTTTGGTAGAGACTGTGACAAGTGGAGGTGATGTTAC

CCTCCTGGAAGAGTGCTGGGGGTCCACAAAGGACCTTGGGTAGGTTATTGCCATTGCTTCATACTTGTT

GAATACTAAGCATTAAACCGAATGACATACATCTATTTTAGACTGCAGTATAAAGAATACCCTAGCCCC

TTACCAATACCCAGCCCTTGGGAAAAAACACAGTAGCAGGTGCTGTTTCTCTAGCTTTACTTGTTTAAG

ACACATTTCCCATTAGATTTTCCTTTTACCGACCCTCGATAACAAGGTTATTTGAAATCCCCAAGGATC

CCATGCTCCCTTTTTAAAACTCTGCATAAACATTTCTTATGTTCTGAAAAAAACCATGGAGTGTGTTAA

AAGTAACTTCATTGATTTAGCTGCAACTTCCTGGAAATTTTAAGTTCTTTGAATGAAGGGCCAATAATG

TTACATTCTTCTTGATGTTGACTATCTTCTTATCTTCCTTGGGGCCTTGTAGAGAAATGCTGCAGTACA

AGCCATCTATGTTTTAATGCGAGGTCCTTACAAGGTCCTGAGGGACTCTTACTTGCACCTCCTTCCTTC

CTAACCTCACTTCTTACTCCCCTTTGCTCACTCTTACCTGGCTGCTCTGGTTTCCTGGCTGTTCCCTTA

ATACTCCAGATATGCACCTGCTCCAGGGCCTTTCCATGTGCTGTTTTTGCTCCTGTAATACTGCTCTTC

ATGATGTTCCTATGGCTAGCTTTATCAAGACCACCTCCTGCAAAATTCTTTACTCTTTTCTTTGTATCT

TCTATATTTTTCTCCATAGTACTAAACACTATCTTTTATACAATAAACTTTCCTTACTTTTTAATTGCC

TGTTTTCTCCAGTTAGACTGAGGTTCCATAAAGGCATTGATTTTTGTCTGATTTGTTCACTGCTCTTTC

TCTAGTCCTTAACAAGTTTGGCACATAGTAGATGCTTAATAGATATTTGTTGAAAGAAAGAATGCATTA

ATTAATGGAAAACTCAGGAATCTTTATAAGTGACTTCTGAAGCTGAGTTTATAACTTTTCATCATATGT

CAATCTGACTTGTTGGTAGAAGACTTTGTTTTTTTTTTTGAGGCAGGGTTGCCCTCTTGCCCAGGCT

GAAGTGCAGTGGTGTGATTTTGGCTCACTGCAACCTCCACCTCCCGGGTTCAAGCAATTCTCATGCCTC

AGCCTCCTGAGTAGCTGGGATTACAGGCATGCGCCACCACACCTGGCTCATTTTTGTATTTTTAGTAGA

GACAGGGTTTTACCATGTTGCCCAGCCTGGTCTCGAACTCCTGGCCTCAGGTGATCCATCCGCCTTGGC

CTCCCAAAGTGCTGGGATTATAGGCATGAGCCACCATGCCTGGCCGGTAGAAGACTGACTGTGTCTGTT
```

-continued

```
GAAGAGTTTATTTAAGTTTCAAAACCAAATTTTCTCTTTTCTTAGAAATAGCCTCACAGTCTGGCACTT

CATATTAATACCTCCCTGAAATTAATTTTTCAGGGGACAGAGGGACTTGGACTGGCTTTGGCCCAATAA

TCAGAGTGGCAGTGAGCAAAGGGTGGAGGTGACTGAGTGCAGCGATGGCCTCTTCTGTAAGACACTCAC

AATTCCAAAAGTGATCGGAAATGACACTGGAGCCTACAAGTGCTTCTACCGGGAAACTGACTTGGCCTC

GGTCATTTATGTCTATGTTCAAGGTAAGTGGTGAAATAAAATTCATTTCCCACGTCTCTTTACCAGTTA

TAAAAGACAATAGGCTCAAAGAAGAATTGAGTACAACAAAGGGCTTGCTCTAAAGGCTGTTTGCCAAGA

GGAATACACACAATTCTTCTCTCCTGAGGCTTTCTCTGAGAAATAAGACTCATTGATTCTGGAGCTTGG

GCCGTGTTACCTCTTTTTTGCCCAGTTAGTTTGGGTCTGATCTTTGTTTCCAAGGTAAATCTGTGTTCA

CTGTTGGCCATTGAGACTTATAAAAAGTCTTCCTATGTTTGAGAAGAAAACCTAAAATTCTTGAAATCG

AGGAAGATTTGGGGGTGAATTATGGAGAAATTTCTGTGGAGAGATAAGTTATCTACAGCAGAGTAGGAG

ATTTTCCCAAGAATGCATAGGAAAGCATTTTTTGCCAAGGGCTCTGGAGTTTTTTGCACATAGGAACCT

TTTTTTCTTACTAGTATTTCATAAAAAACAATTCCCATACTCATGTGCAAATAAAGACATTGCTTCAGA

CTCTTTTCAGGACAATGTTTCTTTCCTTTGCTTGTTTGGTCTGAGATCTTGGATGATATGCTGTATCTT

TCTAGGATGTGCAGTTTGGGATTGATATTATGAAGGCTGACTTAACATCCATATAGTATAAAATAAATG

TCACACATATTCTGCATTTATAATGAGTTATGCATTCTTTTGTGTTTCAAAAATCTTACACTATCTTAT

CTTTTCTGTGAAAACCTAACTTAACTAATGAGATCCCTATGATATAAATTTAAGGAATGTAAGGGCTGC

ATCATAGTTTGGTTGGATGTACCAAATATTTTTCTTTTCAGTGAAGATAAACAGACATTTTATGTATTT

ACGTATATGCCTTTTTACATCCCAGAGTATTTGAGACAGGTGAAGATGACTTAGACTTTTTTCCCAGAA

GCAGCTTTTACAGGGCAAGAATTTCATCAGCTTTGGGAAACACACTTGCATATCTCTGCTTACATTTCA

GTAGTGTAATATGGTCAGTGCAATGAAAAAGTGGAGACCACATCAAAATAACCTATGCCACTGGATTCA

CAATGTTTGAGAAATATCTTTGCCCAGAGTAAGCACTGTCAAAGATAGAATTCTGTGCCCTCCTCCTTC

CCTCCACAAGATTTGAAAGAGACAAGGCTCACATCTTGGAGAATTTCTGGCTCCTTTTGACCTGGCAGT

CTTGAGAGATGCAGCTCGGTCAGAAGATTGCAAGGATTTCCTGCTTTCAGCCTGTCTAGAAATACTACA

AGATGAACATCCCCCATATCTCATTATTTACTTCTTCCTAAGTCAGGAAACTTGGAGACATGTGAAAAT

TCATTTCATGAGTTTCAGTAAATATTTTATTTTGAGAGGCTGGGTGGTGGTTTGGGTTTCTTTTGTTTA

TTTCCTTTTTTTGAGATACCGAAATAGAATTGATTTACTAAATAGGTTTAGTCTTACGTCAAAGGGTTA

ATTTAGCTTCCAAAGGCTTGCTCTGTAAGCAAGTTATGTAATATTTCATAACATGTGGATGAAAGGTAG

GCAATATTAAGAAGTGGCAATCCCTAGCACTGTTTATTGGTACACTGCCTGTCTTTGGGTATACCATTA

AATTCTGCTTCCTGTCTAAGCTTAAAGTTCTAGGAGTTGGGCTGTCCAAGATTTTGGCCATGAAGTTAA

ACAATGGGAAGGAAACACTGAAGTATTCTCTATGGATAGGTGTTTAATGTCCCCTCTGGTCGCCACCT

TACTTCCCTAGTCTTCTGACCCCATTCTCTTCAGCAATGGATGGAGCCAGGAAGTGAGCCCTGGCCTCA

TAAGATAATGGCTATGGCATGTGGTGGGCTAGATTGGCTGCTTTTCTGTGCTTTCCAGCTGGGAAGGAA

ATCAAACTTCTGCTGTTGCAGGGAATTAGCTGCCTTTGTCCCCTGTGGTTTAATTAACTCTTTCTTCAC

TTTGACTGACTATTATGAAGCACTCTGAGAATGCTTGATGGGATGTGTTGGGCATAGCAATGTGAAATG

TTATCTCTCTGAGATTTCAAGCATGACTCCACACCACATCATCTCTATCTCTGAGGAATGGACTAGGTT

TCCAGCAGCATGTTAACATTGTATGAGTAATGTTTGATTGGCCTTGAAATCTTTTTTTTTTTTTTTT

TGAGACGGAGTTTTGCTCTTGTTGCCCAGGCTAAAGTGCAGTGGTGCTATCTCAGCTCACTGCAACTTC

TGCCCCCCGGTTCAAATGATTCTCCTGCCTCAGCCTCTGAAATAGCTGGGACTACAGGTGCGTGCCATC

ATGCCTGGCTAATTTTTTGTATTTTTCGTAGAGATGGGGTTTTGCCACGTTGGTCAGGCTGGTCTCAAA

CTCCTGACCTCAAGTGATCCACCTGCCTCAGCCTCCCAAAGTGCTGGGATTACAGGCGTGAGCCAAGAA

CCCAGTCAGAATCTCTTCAGTTTTCTTCTCAGTCTTTGGAGTGGTGACTTTTCAAATGTTTGTCATTGA
```

-continued

```
AGATATCAATGACTGCTAAATGTTAAACTAAATGCAAAAACAATTAAACATGGTTTTAGAAAGAATCAT

ATCCCTAGTCTTCAGAATCTTAAAATGCTCACATGAATGGTCCTCTTGAATAACCAAATTCAAAGTGT

TAGCTGTTTCCTGTTAATCTAAAGATCCTTTGGGATCCATTCATTTATTTTCATGGAATTTACATTATT

TACCTAAAGAGAGAGCACATGAGTATTTTAAATATTAGTAAAACTTGTCGGTAAAGTGTATAGATTTAA

CTTTAAATTTTAAAGTAAATATTATCCTTCATTTTGAAAAAATTATAATGATTAATCTTTTAAAATGTG

AAATCTATAAAAATATATTCTGCTTGTCAATAAACCTTGTGAAAGGAGTCAATCTCAATTGGGAGTTTT

TTTTCAAAATTTTTATACACACAGATATATACACATGCATGTGCATGCACAAACACACACACACACATA

CACACACACCCTCATGTAGCACAGATATCTATCAGCAGAATAATCTGTGGATGCCTTTGGTTGTGTGAG

GTGTCCCTTCCAGTCATTCACTTGTCTGGTTAGAGTTTAGGAACCTGAAAAATGACCAACTTTTCTAGT

AAATACTATTAACTCATTAATAAAACTAAATTTTCTTCTAGATTACAGATCTCCATTTATTGCTTCTGT

TAGTGACCAACATGGAGTCGTGTACATTACTGAGAACAAAAACAAAACTGTGGTGATTCCATGTCTCGG

GTCCATTTCAAATCTCAACGTGTCACTTTGTGCAGTAAGTTGCATCTCCTCCAATCGTCTCTTAAGTTT

TTATAATTTTAAGCTAATATTAAGATGGGTAACCTGTTTATAATATTCACAATGAGTTTTAAGGATCCT

TTAGGAAGGGTCAAATGCAATGAATAAAACTAATTAGTATTCTTAAAAATAAGATGAATTCTTCAGTGA

TCATTGTACATGGCTCTCATTTTTGGTACTGGATTAAATATTTGATATGTCTTTTTATTACCCAGAGAT

ACCCAGAAAAGAGATTTGTTCCTGATGGTAACAGAATTTCCTGGGACAGCAAGAAGGGCTTTACTATTC

CCAGCTACATGATCAGCTATGCTGGCATGGTCTTCTGTGAAGCAAAAATTAATGATGAAAGTTACCAGT

CTATTATGTACATAGTTGTCGTTGTAGGTAAGAGGACATTTCCTTTCCATATCATTAATAACATATCCT

TGTATTAAGATCTTGGAGATAACAACATAGAGTGAAGAAGGATATTGAAAAGTATAGGAACTCAGGATA

TGGTGTTGGGCAATTCATCTGCTCTTCTCTACCAAATAAACCCATGTGCAATTGAGGTTGTCTCTTTTC

TTGCCAAGATTAAGGAAGAAAAAGAAAACTTTTTAAAAAAAGGATGAAAGCGAATGGTATTACTCGAGC

ACATTTTATGAAGAATTCAATGTTCAGAGCATTGCTTGCTATCAATTATTTCAATTATGACTATTTTAT

GGAAACTTCAGCAATTTGCTAAAGCTGGCCCTACTGGCCTAGGGCTACTGACCACTGAAAGTTTACTAC

TTTTCTGTCCACTGGGTTACAACATCTTTGAGATCTGTGAAGGTAGTGCTTTGTAAACCTCTGTTGGCC

ATTTTCCTGGGAGCTACCAAGTATTGGTGAGGCCTGCAGGGAAAAACAATGTGGCATGTTTTAAAGTTG

CATTACTTTAAAAAATAAATCTGTGCAAAGTTATAGGCTTATTTGCTCTCTCATCTTCTCTTTTTTCAA

TTTACTTGCTCTAGGGTATAGGATTTATGATGTGGTTCTGAGTCCGTCTCATGGAATTGAACTATCTGT

TGGAGAAAAGCTTGTCTTAAATTGTACAGCAAGAACTGAACTAAATGTGGGATTGACTTCAACTGGGA

ATACCCTTCTTCGAAGGTAACGCTAATGATTCAAAGCCAGACCTCCAAATACTTAGATAATAAGCCCCA

GTGAAGTTTGCTTGAGAGATAGGGGCCTCTTTGGCCAGATAAAATGTAAGAGCCTTAAACACACACACA

TACACACCCACTCACACACACATACACACACACAATTTAAGGGAATTGCAGAACAGATAGCACCCAC

CAAAAGGTGAAATACCAGGAATTTTGTCCTATTCTGCAATAGCCAGGCTATGAATATTAGTTTTCTCTA

GGTGATTACATCTTTCCACATTATGTCATTTCTCTGTTCTCCAAAGTTTTTGATCTACATTCCTTTTAA

GGGAATTTCTCTTTAAGAGGTGGCATGAGATACACTGCTCCTTAAACAGTGGTCACATTTACTTGTCTT

TCTGCAGTTTATATCCATCTCACTTTCACCACGTGAGGTTTTAAAAATCCTAATTCAGTTGGTTCCATT

TATTTCTCCTGAAACAAAATATATTTGTTGTCTGCATGAGGTTAAAAGTTCTGGTGTCCCTGTTTTTAG

CATTAAATAATGTTTACCAAAGCCCAGATTTAATTCTGTGTGTTACTAGAAGTTATTGGGTAATGTTAT

ATGCTGTGCTTTGGAAGTTCAGTCAACTCTTTTTTTCAGCATCAGCATAAGAAACTTGTAAACCGAGAC

CTAAAAACCCAGTCTGGGAGTGAGATGAAGAAATTTTTGAGCACCTTAACTATAGATGGTGTAACCCGG

AGTGACCAAGGATTGTACACCTGTGCAGCATCCAGTGGGCTGATGACCAAGAAGAACAGCACATTTGTC
```

-continued

```
AGGGTCCATGGTAAGCTATGGTCTTGGAAATTATTCTGTGCCTTGACAAGTGAGATAATTTAAATAAAT
TTAGGTCACTTAGTGATTCCTATTTTCTTCATTCAGAAGATAGTTTCTAGTTTTTCTTGTTAGGGAGGC
CACATGACCTAGAGGTCAAGAGCATAGCTTTGTAGTCAGGAACTTGGGTTCAAACCTCAACTTTAAAGA
TGAGATGTGCTGATATACAGTAAGAGTTCATTTAGTATTACTTATTATAGTTATTGCTGCTATTAGGAT
TGTTACTATGATAAATAGTATTAGCTAAGGTAGTTTTTAAATTTTCATTTTATTGCAAGGCTGAGAGGC
CTACTTGAATAAGCATGAGCTTTGCAAACTGGGGAAACATTTAGCAATATACAGTTGACCTGTGAGCAA
CTCAGGGATTGGGGGAACTCAGGGGAGTTCCCCTAACTTTCCCTCCTCTGCAGTCAAAAATCCATCTAT
AGGCCGGGCGCGGTGGCTCACGCCTGTAATCCCAACACTTTGGGAGTCTGAGGTGGGTGGATCACCTGA
GATCAGGAGTTCGAAACCAGCCTGGTCAACATGGTGGAACCCCATCTCTACTAAAAATCCAAAAAATTA
GCCTGGTGTGGTGGTGGGAGCTTGTAATCCCAGCTACTCAGGAGGCTGAGGCAGGAGAATTGCTTGAAC
CCAGGAGGTGGAGGTTGCAGTGAGCCAAGATCGTGCCATTGTACCCCAGCCTGGGCAACAAGAGTGAAA
CTCCTTCTCAAAAAAAAAAAAAAAAAAAAATCAAGGTATAACTTTTGACTTCCACAAAACATAACTAA
TGGCCTACTGTTGACTGGAAGCCCTACTGATAACATAAACAGTCAATTAACACATATTTTATATGTTAT
ATGTATTATATACTGTATTCTTCCAATAAAGCTAGAGAAAAGAAAATGTTATTAAGAAAATTGTAAGGA
AGAGAAAATATATTTACTATTCATTAAGTGTAAGTGGATCATCATAAAGGTCTTCATCCTTGTCTTCAC
GTTGAGTAGGCTGAGGAAAAGGGGAAGAGGAGGGGTGGTTTTGCTGTCTCAGGGGTGGCAGAGGTGG
AAGAAAATCTGCTTATAAGTGGACTCATGTAGTTCAAGTTTGTGTTATTTAAGGGTCAACTGTAATTGA
ACTGGAATTAAATTGAACTGGCCTTGAGAAAATCACCTTAATTTTTGTTTATTCTCTTTCATTTACAT
AAATGTCTGAGTTTACATGGTAATTTGTGTGGCATCCTACTTATAAGCCTTGGAAAGGATTTTGGAGTT
TATATTATGAGAATGCATCAATACAGTGAAATTTTAAAAATACCTTAGATAATGCTATTTATTAGAGTT
GTAATCATAAAGTGGCAACAACTATAACAAGTATGATTTAGTGAGCACTTACTTTATTAGCTCATCTC
ATCTTTGAAGCTGAGATTGGAACTCAAGTTCCTGACTACAAAGCTATGCTCTTGACCTCTAGGTCACGT
GGCATCCCTAGCAAGAACTTGAAAATTTCTTCTGAATGAACAAAATAGAAATCACTAAGTGTCCTAAAT
TTATTTAAATTATTTCACTTGCCAAGATGCACTTGTCAAAATACACAGAGAGATGTGCTCTGGCTTA
TGTTTTTATAGAATTACTTTTGTTTTCCAGAATACTTCAGGGAAATAGGGGCAGAAATAAGGAGGTCAG
TTGGGAGGCTAATTGCAGTTATCCAAGTGAGAGTTGAGGGGTGGCTTAGACAAGGGTAGTTGAGGTGGA
GGTAGTGAGAGGTGATCTGCTTCTGGATATATTTTGAAGGTAGAGTCAACAGGGTCCGCTGATCAATTC
ATTGGTTGTGGAGTATAAGAGAAAAAGAGTGGAAGATGACTCGAGCGTTAGCATGAGCAACTGAGTAAA
TGATGGTGTTATTTACTGAGATGGCAAAGATCGAGAAGGCAGTGAGATTTAGGGAAACAGTGTTAGATA
TGTTTATCTGGAGATGCCTGTTAAACATCCAAGTGGAGATATTTAACATATCAACCCGGAACCCAGAGG
AGTCAGGGCAGAAGATAACACATTTAGGAGGTACGTGAATGATACTTTAAACCTGAGGCTAGAGGAAGG
TGTAAATAAAGAGGAGGTCTGAGGACTGAGTCCTGGGGCCTCATGGTGGAAGAGGTGTGTGGAGGCTGT
CATGGGAGCAGAGGAGAAGGAGCACCCAAGCATCCCTGGGGGACTTAGAGAAAGCTGCACAGAGGAGCA
AGTGTTTGAGTTGAGACTTGAGCAATCACTAGGCTTGTGGGAGTGCACTAGCGGGGAGAGAAAAGCAAA
TGCAAACACAGGAGGTGTGGGAGAAACACGGGAGGTGTGGGAGAAGCTGAAAAGTGACCCACTGAAAGA
TAGTACAGGAAATCTTGGAACTGCAGCTACTCAGACCCTCAAGGTCTTTGACGTTTCACTTGAAATGAA
AAACTAAATCAAATGACCATTTACAGTAAGTTGACCTTTTTTTTTTTATTTTCTTCCAGAAAAACCT
TTTGTTGCTTTTGGAAGTGGCATGGAATCTCTGGTGGAAGCCACGGTGGGGAGCGTGTCAGAATCCCT
GCGAAGTACCTTGGTTACCCACCCCCAGAAATAAAATGGTAACTACTGGAAATAAATGCAAAGCATCAT
TTCGTGTGAGAGCAAATCCTTTGACTATACTAATTCCTGAGAATTTTTTTTCATAGGTATAAAAATGGA
ATACCCCTTGAGTCCAATCACACAATTAAAGCGGGGCATGTACTGACGATTATGGAAGTGAGTGAAAGA
```

-continued

```
GACACAGGAAATTACACTGTCATCCTTACCAATCCCATTTCAAAGGAGAAGCAGAGCCATGTGGTCTCT
CTGGTTGTGTATGGTGAGTCCATTCAATTTTCCTCTCTGCCCAAGATTTATTATGATACATTGTCTTCC
AAATCAGCCAAACCACCGTTCCTCTGCCTCCTGCTGCTTCACTCATATCATGGCTGGGCCTGCGTACAA
AAGTCATCTGGCGTGGTGAAGCTGAAGTGAAACGTAGGACCATGTGCTCTGGCCATGTTTGTTTAAGAG
GCCGTGTAAATGAGCTTTGTGGTGGACAAATGCAAGATTAAAGTAGTGATACCCTCGATAGCTAAATGT
TGTGAAATAAGAATGCCCACAGGGACAGTTGTCAAGCTAAGTTATACTACCATGTTCCCCTCTCATGGA
ATTGCCCACCTGGTACACAGATGTGTAAGACCCTTCTCCTTAGATTTTGTGCAAAGCTTCTAGTTTGAT
GTTGTAGTTGATGTATCAGAGATGTGCAGGCACGTTCCAACTCTGAAGGCTTTTGAAGTTGACACTGTT
GGCTTGGTTGGGAGCTTTTCTTTTTTCCTTTTTGACAGGAGTTCAGGATCTGATTTTGAGTCTGTAAAG
GAAAGATAGTAAGTTTTTGATGTAAAGATAATTTGAACTTTGTTTTCTGAAACTGAAAGGTACAAATAA
GTGTTTGGAATGGAGTGGGGAGAAGGGTGCCATGGTCAAGTGAGTGTGAGAGGTGCTAAGGTGATGTGT
AGATGTGTAACAGGTTTCTTTATTGCAGGACTTCGCAGAACCTTTTATATGCTAATGTATATTGGTATT
CTCCAGGAGGAGAGACATAGAGTATTCAAGGTTTAACAAACCTATTTGACCAGAGCACCTTTTTTCCCC
TGAGCAAATTCATTAATCTCTCACTCCAAACAGTTTGAGAAATGCTTCTCTGTTGTAATTCTTTGTTCC
CCCTTCTGGTACGGCATATTAAAACTTCAGGATATTTTCCCATGACATTAAGGTGCTTCCCTACGTGTC
CTGATACTCTTCTGTAGGCCGCTGAACTTGGCTTTATTATTTTTTTCAGGGAATATTTTAAAGATAGG
CTGGGTGCCGTGGTTTGCATCTGTAATCCCAGCACTTTGGGAGGCCGAGGCGGATGGATCACCTGAGGT
CAGGAGTTCGAGACCAGCCTGGCCAACATGATGAAAACCCGTCTCTACTAAAAATATAAAAATTAGCCA
GGCATGGTGGTGGGCACCTGTAATCCCAGCTACTTGGGAGGCTGAGGCAGGAGAATCACTTGAACCCAG
GAGGTGGAGGTTGCAGATAGCCGAGATCGCACCATTGTACTCCAGCCTGGTGACAAGAGCAAAACTCCG
TCTCAAAAAAAAAGTTAACAGGTTCCAAAAAGGTTGTTTAGAAGCAGCATAGGTGTAGGGGACTGGGGA
GAGGAGAAACTGGAAAGTGTATAAGTAGGATGGGAGGAGGAAATGAACAGGAAATAAAAACAAAACACG
GACAGCAAATAGCCCATTTCATCAGTTCATGAAGCCACTAAATATTTTATTCACTTTAGCAAATTCTCT
GCTATATGAAATAAACATAAAAAAGAAGTCAAGTCTTCAAAGCATAATCTGAGGCTTTAGGTTGACAGT
AATAAGGAAATAGTTTTGACTTTGGAGTCAAAAAGAAAGAAAGGAAAAAGGGAGAGAAGAAAGAAGGA
AGTGAGAGAAGGGAGAAGGAAGAAAGGGGAAGAGGGAAAGGGAGTGGAGAGGGAGGGAGGGAGGAAGAG
GGAGAGAGAATGAAAAACTCAGATGATGGTGGCAGGAATGCATTCTCTAAAGATTTACACCTTCCTTTA
ACATGAGGTGGTTTACGTGTTTGGGTTCAGAAGTCAGAGTGTCTAGGTTTGTTCCAGGTTTTGCCGTTC
GTTAACTGAGTGACCTTGGGCGAGTCATTTTTTTCTGTTTCATTTTTTTCTCACGTATAAAGCTGTGGA
CAGTAATAGTGGTTGTGAGGATTAAGTGAATGAATTCATGCAAAGCACTTCAAACAATGCTTGGCACAT
AATAAATGTATTTACTGTGCTATTTCAGCTGTTTTCTGTAGCCTTTCCCTGATCTCCTAAACTTGAGAG
GACAGAGAGAACTATCTCTGTAATACAGATGAGAGGCACAGGATTTCAACACTTCCATAAAGTCATTCA
GCTTGTTAGTTTATTATTATTATTAGCTTATTGTCATTTTTATTTTATTTCGTTACTTTATTCCTTTTT
TTTTTTTTTGGTAGAGATGGGGTCTCACCATGTGGCCCAGGCTGGTCTTGATCTCCTGGGCTTAAGCGA
TCCACCTACCTTGGCGTCCCAAAATACTGAGATTACAGGCATAAGCCCCCATGCCTGGCTAGTTGTTAT
TTTTATGAGTATCACTAGAACTCAGGTCTCTTGTTTCCACATCTAGGTGTTCTTCGAAAAAGAAAGTGG
AAGCAAAATCATATGCTTAAAGAAAGTCAGCTTTAGTTGCTAAAATCCTCTATTTCCCATTCTTCAAAG
CTGACTGACAATTCAAAGTTGTTTTTCCCATCTTCAGTCCCACCCCAGATTGGTGAGAAATCTCTAAT
CTCTCCTGTGGATTCCTACCAGTACGGCACCACTCAAACGCTGACATGTACGGTCTATGCCATTCCTCC
CCCGCATCACATCCACTGGTATTGGCAGTTGGAGGAAGAGTGCGCCAACGAGCCCAGGTGAGTAAGGCC
```

```
ACATGCTCTTTGCTTTCCTGCCATCTTGCATTTCTTACAGCTGAGCTATGATATGACTCCATCCTAAAT
GGAGAAGCCTAAACCAAAAAAAGTTTTCTCTCAAGAGGTAGCCTGAATCTCCATCCATCTTTCTCTGTG
TCTTACATTTTAGGGGATGTCTTTGCTTGGAGTATCCTCCTTTGGGGTTAGCTAAGCTCAGCCTTGTTA
GGTTAGCCGTGAGGTACACTTCTCCAAACACAGGCTATTTGCTCAGTTTGCTAATTGCCAGTCTTTGGT
TTTTCTCCCGATACCAATCGGCTGGTGAATACCACATCCCTCCTTCTTGTGTGTGTGAAGATCCATCTC
TCAGAGGAAATGCTGATAGATGAGAGGCAGTGATAGACCCAGCCCCAGTCCTCAGGGTCTCAGGCCCAG
CTTATCATGCTCTGACACAAGTCCAGACATCCTTAGGGAAAAACACAACAACAGCAGCCAACCCACCAC
CACCCTAAGCAGTCCACTTCCTGTTGTTGTTTTTGAAATGGCCACTATGAGCTTCTTCCTCAGCTGCTG
ATCATTTCCTTCACAGAGACCATGGTCCCAGAGAAATTACTTTAAGGAGCCCAGTGGCTTCTAAGTTTC
CTTGCCTTCCTTTGAACTAAATTAACTTGAATTGTCTTGTCGATCCAATTTATGAATGAAGGTTTATTC
CCAGAATAGCTGCTTCCCTCCTGTATCCTGAATGAATCTACCTAGAACCTTTTCCTTCATTGTCAATGC
CTATTTTAATTGGCGCCAAGTCTTGTACCATGGTAGGCTGCGTTGGAAGTTATTTCTAAGAACAGAAT
AACCAAAGTCTGAATCTTTTCCTTACTCTTGACTCTAATTAAAGAAAAATTAAATCATAATATGCGCTG
TTATCTCTTTCTTATAGCCAAGCTGTCTCAGTGACAAACCCATACCCTTGTGAAGAATGGAGAAGTGTG
GAGGACTTCCAGGGAGGAAATAAAATTGAAGTTAATAAAAATCAATTTGCTCTAATTGAAGGAAAAAAC
AAAGTGAGTTTGAAGTTTTAAAATTTGAAAATCTCTCTCTCTTTAATGGAAGGATGGTACAATAATATG
TGAGGCATATTGGAGATTAATAATCAAATAGTCTGGATGATTAAATAGAGCGTATTAAGTCACTTTGAA
AATACCATTGACTTTTAGCAGTACCATTAACTTATTAATAGCTTATCAGAGAAAAATAAAAACATCTAT
GACATTAAATCTATGCATCTGTGTAGGGTGATTCTGATTTTATAAACATGAGAATGAAAAAATGTGTAT
CATATCATATTAAAACACATCATTAGTTTCATGGCTTCCAAAGCCCTTTTTATATAATGTGTGAGCTCC
ACAGCAGCATAATTATACAAATTGAGTAAATATCCCAAACCTAAAAACCCCAAATCCAAAATGCTCCAG
ATTCTGAACCTTTTTGAGTGCCGACATGGTGCTCAAAGGAAACGCTCGTTGGAGCATTTTGGATTTTCA
GATTAGGGATGCTCAACTGGTAAGTATACAATGCAAATATTCCAAAATCCAAAAAAAAAAATCCAAAAT
CCAAACCACTTTTGGTCCCAAGCGTTTTGAGTAAGGGATACTCAACCTGCAATTGCATAAATTTGAGCG
TGTCCAACCGCTGCAGAAGTGGGAATGGCATAGGCAGGTTGGAGTGATTGTGGAGACTGCTGGACTGAG
TGCTTGTGCACAAACAGCCGCGTTGTTTATGGCCTGGGATTTGTTTTTTCCCCGCACAGACTGTAAGTA
CCCTTGTTATCCAAGCGGCAAATGTGTCAGCTTTGTACAAATGTGAAGCGGTCAACAAAGTCGGGAGAG
GAGAGAGGGTGATCTCCTTCCACGTGACCAGTAAGTACTCTTCTCTGGAGGTTTGGGTTGGATCACTCA
CACAGTGGGTACTAAGCTATGTAATTCCCTCTTCTTTTTGCCATTCATGTGAGTGGCATGGCATTTAGG
AAAGAGGACTTGGATTGATCATTGATGCTTTCATTCATAAATTACAACTTCTCAGGTATCTCCTGGGCT
TATGTGAAGTCAGTGCGTCTAACTACACTGGAGAGAATGGTTTCACAGATGCTTTAAACCACAAGCT
CTGTGTGGTATTTACATCTCAGTCTTCAGAGTCTGGCACAGTGCCTGGCTTATTGAGCTTCAGTACATA
TTGGTGGGCTTGCTGTGGAACAGTTGATGAGGGTGGGCTTTATGGAGGCAATCAGAAGGACATAGGAGC
AGTGCCCTCCCAATGCTGCCGATTTTGCCTGTGCATCTTAGTTTTATGGATAAGCTTTAGCTGATTGTG
CTGAATGGAATATTATAGCCAGGGCTAATTCATTGGCATAAATGTAGCTTTCATATCATTGAGTGTTAG
TGTTAATGAAGACCTAATTTTAAAATTCTGTTAGAATTAGAGATTTTGCTTTGGATTTTTAATATATTA
AACATTGCGTAGAGCTCATAGTGGAGATGTGGTAAATATCTGAGGAATTCGTTTACATTTTCAAGTAAT
GTGTTTGGCCAAATAAGATATTTTGGGACCTGAATTGTCTAGTTTGTTTGTCAAGTTGTAGTACATCAC
CTGGAACGGATAGAGCTTCATTTCTTTTGGTACTTTGTAGTAGTCTGAAAGCAGCAAGATGATAGTGAG
CTGTACCAAGTTAAATCACCATTCAATAACTATCCCCTCTTCATTTTAGGGGGTCCTGAAATTACTTTG
CAACCTGACATGCAGCCCACTGAGCAGGAGAGCGTGTCTTTGTGGTGCACTGCAGACAGATCTACGTTT
```

-continued

```
GAGAACCTCACATGGTACAAGCTTGGCCCACAGCCTCTGCCAATCCATGTGGGAGAGTTGCCCACACCT

GTTTGCAAGAACTTGGATACTCTTTGGAAATTGAATGCCACCATGTTCTCTAATAGCACAAATGACATT

TTGATCATGGAGCTTAAGAATGCATCCTTGCAGGACCAAGGAGACTATGTCTGCCTTGCTCAAGACAGG

AAGACCAAGAAAAGACATTGCGTGGTCAGGCAGCTCACAGTCCTAGGTAGGGAGACAATTCTGGATCAT

TGTGCAGAGGCAGTTGGAATGCCTTAAATGTAGTGCAATTCAGGTGCTATGCAAAGATTACTGTCCTCT

AGGAGATTATGTTGTAAACTGGTGCACACTTCTTCACCGAAAGTCCTTGAGGAAGAAAGAAGCTAATAA

TAATGAAATGATATATCGAAAGGAGAAAATAACAAAACCTGATGATGGAGTAATTCACTAGTATATGCA

AGGGATATTAGCTTGAACCAGGGAAACTTCTGCCTTATCTTGGGCATCCATTTATTTAAATAGACAAAT

ATTTGTGGAATGCCTGCTATGAGCTAGGAGAGTGTCAGAAATTCACAGTGGTAAACATGAAGGAAAGGA

GGAGAACATAGGCAACCACTGGGAAGTCACAGCACAGTGAGGTCTCTGTGTCCATGAGAACAGGAATTG

TTCTCTGTTTTGCTCCCTGCTATAGCTCTAGTCATAGAGCATAGCAGCATATACTAACTGCTCAATAAG

GCACCTGCTGCATGAAGAGTGGGATGATGGGCTGCGTTTAAGACCTAGAAGACTCCATGGGAAGGAAGC

TACATTCACTGTCTGTACCTCTGGGTCATCCCACATGATCCAGCGTAGCCCAAGGTCAATGGGACGATC

ACTTCAGTGAGCAGATAGCTCTGTAAATTCCTCCATAGAGGCACTGTCTACCCCTTGTCTAACCTCATG

CCTTGTGCAAAAGCTGGGCAGCCATGGCTTTGTCTGTGGGAAAATCAGGCAAATTTGGGGAGCGTCTCT

TTGTGCCACTTCTCTCCATTTTCTCCTCTTGTGGTGTCCCTTTCCAATTCCTAGGATATATGTGCCCTC

TGTTTTTTTTTTACTGTTAGGAAGGAAATTGCCCAAGTAAATTCATCTATACCACAGTTTTAGAGGGTA

ACGTCTTCATCAGAGGCCTTGGCGTATTTGAAGAGGCACCTTCTGACAGACACTAGCATAAAGTTCCCT

AGTTTTAAGACTCAGGTGTCATAATAAGAGATACTTTGGGGTCAAGTCATCCCCAGCATCCTTCAAGTC

ACACCACATAGATCACATGGATTTTCTGTTGGCTTGTCTGGCTTCAAGGTTATGGCAGAATTGAGAAAG

AGATGTGAAGTAGGCTCCTGGCCTAGCTGTGCCCAGAAAATATGTGCTCGCAGTTAGCTGCTTTCCTTC

CCTAAGGACTCCTAACTTGTTTTCCTAAAACCTATTCTTAGAAATAGGCTAGAATCCAGTACATTTCCT

TAGACTTCAATGTAGTACGCTGTTGAGGTAATCTCATTTTGCTAAGTGTTGACGTGGATTTTTTCAGCA

TGATTCCTTTTGATGTTCAGTTGGTTGGGACAAGATATTTCCACAGCACTTTGATGATCTGAAGAAAGA

ATAAATCTAAAGTGTTCTTGTACACTTAAACAAATACTCATGGGCTTCATTTTCTTTAAATCCAAGACT

TCCCTTAGGGTATTGTTGTTTGTTTGTGTTTTAGTGGAAATAGCACTGAACTGGTCTTTTAGCCTCAC

CAGATTCTGTAAACAGTTCAACTGTTTACTTAGTTGCAGGGACATGGACAAGTGGTTTAATGTCGCTGA

ACATCATTTATTTCATCTGTGAGATAACGCTAACAGTCCTATTCTGCTCATTACATAAGATCACTAGTG

AGGAACACAAATTGTGTAAACAAGTTTTATAAGAATTGCCAAATAAATGTAAGGCATTATTGGTTGAAT

GATACTAAAATTTGGCACTTCCAAGAGAAATTTGAAGGGATTCTAGGGTATTATTGACTAGAATCTTCA

TGGGAGGGAAGTTTTCACCTGGGGAGGCTGTGTCTAATTAGAGGAAAAATCCATAAAGGTGACCCTGAA

CCTTTCTTTTGTGATGGGATTACCAGCTAGTATCACTAATATGAATGTTAAAAGCCATTAATCTGTTTG

CAGTGTCCTGACTGACTTGTTTCATTTAACTTTACCCAGTGACCAGTGTATTTTCCCAGAAGTTAATAT

ATCAACAAGTTCCTTTTTACTAAATTTAAACTGTTTAAAAGTTTGCTGATACCAGAACCATTTCAAAAG

TTATAATTCCATGTTCTGTGATTTTCTTTTTGTGTGTCTAGAGCGTGTGGCACCCACGATCACAGGAAA

CCTGGAGAATCAGACGACAAGTATTGGGGAAAGCATCGAAGTCTCATGCACGGCATCTGGGAATCCCCC

TCCACAGATCATGTGGTTTAAAGATAATGAGACCCTTGTAGAAGACTCAGGTAAATAGAATTTGGCTAT

CACTCTTGGGTTGCAGAACTTTCCCAGGGATGTTATCTAAAAAGCCATATTATTTCTTGATGTAATGTA

GAAAAAAAGCAGTATTGGTGTCCATGACCTGGCTCATTTCACAGACTTAGAATTGGAGTATGGGGCCCT

GTTGAATTTTCATGAAAGCCATATAGGAGATTAGTCAGCAGTAGATCCCATGTGACTCTACAGAGTTAG
```

-continued

```
ATAATAGAACAAGATGAAGGGCAGCATTTATATTTTCTAAATTTCCCTGAAAAACTTCACAGACTACAT
CATCATAAATGAGAATGATCGTTTTCTTCCTCTGTTAGGCATTGTATTGAAGGATGGGAACCGGAACCT
CACTATCCGCAGAGTGAGGAAGGAGGACGAAGGCCTCTACACCTGCCAGGCATGCAGTCTTCTTGGCTG
TGCAAAAGTGGAGGCATTTTTCATAATAGAAGGTCAGTGGGATAAAAAAAAATGTGGTACATATACACC
ATGGAATGCTATGCAGCCGTAAAAAGGAATCTGATCATGTCCTTTGCAGCTGCATGGATGGAGCTGGAA
GCCATTATCCTCAGCAAACTAACACAGGAACAGAAAACCAAACGCCACACATTCTCACTTATAAGTGGG
AGCTGAACAATGTGAACACATAGACACAGGGAAGGGAACAACACACACTGGGGCCTACTGTGGGTTGGG
GAGAAGGAGAGCATCAGGAAAAATAGCTAATGCATGCTGGGCTTAATACCTAGGAGATGGATTAATAGG
TGCAGCAAATCACCATGGCACATGTTTACCTGTGTAACAAACCTGAGCATTCTGCACATGTATCCCGGA
ACTTAAAAGAAAAAAGAAGGTCAGTGGGAAGTCATAGATACATCCTGTGGTTTTTGAAGATTAGTTTG
TATCTTATAGACACACATTCACTTTGAATAGGGCAACGACAGATGATTTTTAATATTCTTTGTACTTTG
TAAATTTTCTCAGTGAGTATGTATTCTTTTAACCAGCAAACATAATTAATGTTGTTATAATTCTGCTTG
CATCACATTTCCTATTCCTGCAGTTCTTATTGTGGAAAAATTCTTAATCAGGCAGGATGAATAGCCTCT
TCTCCCTGATTCTGTCTTTGTTTGAATGGCTTGATTAACTTATAGAAATGATGCCTTTATATTTATTTG
GAAAAACATTAGAATTGCTGCCTAATCATGGCAGTCAATGCTATCCAGATAGTCACAAGGATTCCGAGT
TTTAATTGGACTAGAGATAATTAAGATTCACTTGTGAACAATAGACCATTGCTCTTCTGACATGGAAAA
TTTTTGGTTTTTATCTCAATACGTGTGTATGCAGAAGTGATGTGAAATCTGTCATTTTCTTAGCTAGGA
AAAGTAATTTGTGGCAGAATATTTTATCTTAAGAAGTATATTCCTATGGCTTTTTTTTTATAGCCCAC
CAGGGAAAGAATAAAACTGTGTTGTGGGGTAAAAGAATGGTATGCAAGGGTAAGAAAGAAGTATGGTGA
TAGAAGGGATCGATGGATTTCTATGAACTCATCCTAACTTGTCTCTCAAAGTCTAGATTTTGGTCCCTT
TACTCTGCCAAATCTATGATGCCAAGTATTGCATCGAGATATGTTGACATATTTTCAAATGTATAAGCT
TATTAGCATTTCATAAACTACACTTGCAAATAAAGATTTCAAAGACCATGGCGGTTTTGTCATTTCCAA
AGTGATTCATGTTTTAGGGCAAATCCGCAGAATGACGTCTAGATTGTCTCTGATGCTCTGCATTACCTC
TTGTTGGTGGCCTGCAGCTGGTTACAGATGCCTAACTAGGTAACACTGGCACAGAGATTATAGTTACTT
CTTACCTGGAGTGAATGCTAAGAAAGGCAGAGCTAGATATTTAATACTCCTGCTGGGTTCCCAAATGTT
ATGCGAGAATATTAATATACAAACACATAGAAAACAGACTCTTTGAACTTTTTATCCTCTATGTTCAAC
TGGACTTTTAAATCTGTGTGTATAAATAGAGAATTACTTCCCTAGGACCACCAGAGAAACAAAATTTAC
TCCAAGCATAATTGTGCTTGTCTCTCAATGGTTAAGTTAACTTTTATTTTGCAAACCAATTTGTTACTT
ATTTTGCAAACCAGTTTCTTACTTGTCTTCTTCTCTCTTGAGGCCGTAGTGGGCCATCCGCACAGCTTG
TGGCCCGGTTTGATTCTCCTTGCACTCTTCTGATGGGAGGCCCCAAGTGATGACTGCTTCCTTATCATC
TCTTTGCTAATCACTCTTAGTGGAAAGCCTGTTTCTGTATTTTGTTTCTTCCACTCAGAGCTGTCCTCT
GAAGCCCTGAGCATCTGCAGCTTTGCTTGCTGACTTCTAGTTTCCTCTTCTCTTTCCTTTCATGAGTGA
TTTGAAACTCCCATTACCAGGCCATGCGTGATGTGCTCATCTTGGCTCTTCCTCTTCTCCTCACTCAGA
CTCCTGCCACAAGGGATGGGGTAGTGTATGTAATGGTTAGTTCATGTTGGACAGGCCTCTTTATCTCTT
GACTGAACCACTGACTAGCTGTGTGCCCTCAGTCAAGTAGCTTAAGCTCTCTGGTCTTCTGTTTCTTCA
TCTGAAAACTGAGAGTTGTTGAGGAGATTAAGTGGAATGGCATATTTAAAGTGATGAGTGCATAGTAGA
TACATGGTCATTAGTAACTCTCAGGTCAAAAAATTTTGTTTATTTCCCTACTTGGTTTCTTATGTGATC
CTTTTGCAAACTCTGCACAGATCAAAATATTGACTATCAGTTTAAAAGAAGACTTTTGTTTTCCTCAAA
TAGAAATATTTTTTTTTCTCTGTAGAGAATGATCTGTTTTCTTTCCATCAAAGACTGCTCTTCCTCTAA
TAAGTTTACATGAGCAATGTTTTGCAAGCTTTAAATTTTCCATTAACAATTCTGTAGGCCAGGTGTGGT
GGCTTATGCCTGTAATCCCTGCACTTTGGGAGGCCAAGGCAGGGGGGATGGCTAGAGGCCAGGAGTTCG
```

-continued

```
AGACTAGCCTGGGCAATGTAGTGAGACCCTGTCTCTACAGAAAATAAAAGAAAAATTAGCTGGGCTTGG

TGGTATGCACCTGTAGTCCCAGCTACTCGGGAGGCTGAGGGGGGAGAATCGCTTGAGCCTAGGAATTGG

AGGCTGCAATAAGCTATGATTGTGTCATGGTACTCCAGCCTGGAACATAGAAAGAAACCCTGTCTCTAA

AAATAAATAAATAAATAAATAAATAAATAAATAAATAAATAAATAAATTAAATTCAAAAAAAGAATTCT

GTAGACTCCATTCAAGTTACGGGTGTGTAACTGTTGTCCTCTAGGATTTTTCCAAGTTGGTAAGCTTGG

GATTTTGCTTTAGTGCTAAAATTTGTCATCTTACAAACAAAAAGTATAAGTTTCCAACTGTTGATACTC

ATTCAATTGTGTCTTTCCAGGTGCCCAGGAAAAGACGAACTTGGAAATCATTATTCTAGTAGGCACGGC

GGTGATTGCCATGTTCTTCTGGCTACTTCTTGTCATCATCCTACGGACCGTTAAGCGGGTAAAAAAATA

ATTTCCCTTCTGCCCATGCACATTGGTTTTCATGATTAATGAAAACTGACTGGGGTTCTTTGAGTTGTT

TCTTCCCATTGTTATTGGCTCAATGGGCACATTTTTATTTCAATACAATAACGTTCCTGCCCACTTTCT

TTTGGCTGGATCTCAGGGATTTAATTGATAGAAGCCACTAGAGAGGAAAAGGGCTTGGACTGTCTAGTG

TAATTAAGCTTTAAAACCTTAATTCTGAGCTCCTTTGGGGGACAAGGGAAACTAGAAGCAGGGTTATAA

TAGGACCACTCTCAAACTCCATGAGTTTTATTGGAAAATGAGACAGGAATGAGGCTCCAATAAACAGCA

ATAACAAGCACACAAAACAACAGCCAAACAACAGTGTGTTTATGACTGGAAGGATTGATGCTTTCCAGG

CCAATGGAGGGGAACTGAAGACAGGCTACTTGTCCATCGTCATGGATCCAGATGAACTCCCATTGGATG

AACATTGTGAACGACTGCCTTATGATGCCAGCAAATGGGAATTCCCCAGAGACCGGCTGAAGCTAGGTG

CATTTTCAATTGCTATTAATTTGATATTGTGTTTACCAGGCCATCTCTTCCTCCATTAGAATGATGACA

AATGTGGTGTATTCAGATGTTGGATTCTGGTTTAGAAATATTAATTCCATTTCTTGAATTTGTATAATC

ATTCATATAGCCACTTAGAGGTAGGGTCCCTATGTAATCATCCAAAGCAGGACATTTGGAGAGTGAAGG

GGGAGTTATTAAATAATTAAGCCAGGACAAAGGAGTAAACTGGACTATCCATGTTAAATTGGGATGTAT

GGTCACCCTATCTAGTTGATGTCTCTGCGTATCACTTTGGTTGTATAGTAATCCAAGTCTGTTTTCTTG

TTGCTGTTGTTGTTGACTCTAGGTAAGCCTCTTGGCCGTGGTGCCTTTGGCCAAGTGATTGAAGCAGAT

GCCTTTGGAATTGACAAGACAGCAACTTGCAGGACAGTAGCAGTCAAAATGTTGAAAGGTAAAAGCAAA

GCCTTTGGAATTGACAAGACAGCAACTTGCAGGACAGTAGCAGTCAAAATGTTGAAAGGTAAAAGCAAA

ATTATGTGGTGATCTATCTTTCTGTTTTATCTAGTCTTTAAATATGTTGCAAGGCTTGTATCAGTAGCT

TTGTGCTTATGTGGGCCTACTAGCCACACATGCAGTCAGCCTAAATAATGCCCTTGTGCAAATTGGAAA

AAGGATCCTCCTTTGTAGCTTTATGCCAGGATGCATGGTCTGGCAAGCAAAGTTGGGAATGGCTTTCAC

CTTCTTGCCTGGTTACCCTCGTGCAGGGCTCAGCCAACACAGTTGTACTTAGTGGTTCTGGGTACAGGG

AAAAAGGACTGTGGTTATATTAAAATTGTTTCTTAATATATTGTGGAATCAGATAATTATAGACCATCT

AGAGACATGGAAAGGAAGATAGTGAAATACAAAAATAGCATGTTCTCCAGAATTGGAATATGTAAAAGA

TGTTCATATGTAAAAGATAATTTGCAAACAAGAATGGTTGTGTTAGAAAAAATATAATGGGTTATAT

TTTTTAAATTAAAAGCTTTATAAATAATTGTTAATTCTAATAGTAACGGAATTCTGGTCTGGCCATTTT

CATTTTAGGAGGTTAGACAGTAAAGCTTCTTTCTTCAATTGTGATGTTCTTTCATTGATGAAGGCAGTG

CCAATGACCCTTTGCCAATAGGTTTTGTGCATTTCAAAGCTATCTTTCTCCATCTGCCTTTTTTCTCTT

GTGGCCAAGGGAGTGTGTAATTTTGAGGTGGCTCATCAGAGCCTTAGATGTGGACCATGCCTGTGAATT

AGTGGGAAGTGTAGCAGTCCATACAGGATCAAACACATAGTCTTAGTGCCATCAGCCTCATGTGCCAAC

TGGTCTTTCCAGCTGGCCTTAATTCGCCTGCACAGATCGGCACAGATTGGCTGGAACATTCGGTATAGC

CCCTAACACGTGAAGATATTTAATACATGGTGTTGCTTCCTTATGAGGAAGTGCTGAAATGATCAGACC

CTCAGAATCATAGTGAACCTGAAATGCAAAAATCCAGTTTTGCAGAAGAAGAGAATCTGGGCATGATTC

CACTGCAGATGTATTCTCCGCTTTGCAAAAGGTTTCACAATGGGTTCCTTTAAATATCAAACTTTCTGG
```

-continued

```
CTCACTTAAAATATGAATTTTATTTCAAATTAGAAAATAGAATTTACACTTCACTTTTGAGGAAATGCA
TGTGGTCTGTAAACTAGGTCACAGCTGTGTTACCCCGGAGGGTAAGTTGTATAGTGGCATGCAGGGAGG
GAGGGACCCCAATTATTGAAGGAAATGTCCATACCTATGATTTCCCTCTTTGTACTGTATTTGTAGAAG
GAGCAACACACAGTGAGCATCGAGCTCTCATGTCTGAACTCAAGATCCTCATTCATATTGGTCACCATC
TCAATGTGGTCAACCTTCTAGGTGCCTGTACCAAGCCAGGAGGTGAGTAACTGTGGGTGGTTTTGGTCA
CCCAATTTTAACATGCCTCTCTGATAGTGTTTGAGGGAAAGCAGTCAACTCCTCTGGCCTTGATTTTCT
TAGCTTAGAATACTTTGCGGATTCCTAGGAATAAATATATTTCATGGAGGTTTAATTGGCACTAGAATT
AAATTATTGTAAAACTTTCTCTGAATTAAGAAATGTCATGCTACTATGATACAGTTTGTTACTTGTGTA
ACAGATGTCCAGAGAAGAGTAAACTTCCCTAAAACTTGAAAGCTTAAGGGTAGTTACCCCCAAAATGGA
ATCATATCAGGAGATTGCACTGAAAAGCAAGTAGATGGGTGGGTTTTCTTCTGAAATTTTGGTTAATCT
TGTGAAAATGTGTTCTGGAAAAAGAAAAGCTACAATATAAGGGGATTGGGACCAGCTGATTTCTACAC
TCCTGTCCCAATGAAAGGTTGTAGCCTTCTTCTAAGGTGTTTTTGGGTTCATCACTATATTAAACGCTT
AGTGAGGAATATGAGTGAAAACCCATTTTCCTTCCTGGACATGCTGCCTGCAGGGCCACTCATGGTGAT
TGTGGAATTCTGCAAATTTGGAAACCTGTCCACTTACCTGAGGAGCAAGAGAAATGAATTTGTCCCCTA
CAAGGTATGTCATCTCCTAATCCTGCTCTGGCCATGTTATAAAATGAAGGGAAACTCAAAATGGTACAG
GTTAGTTTTTTAGTTGAAATTTTGTGAAGAACTTGTGAGGAATCTTCTCATATTACCTCTTGGCTGTTG
TAACTTCCTCTTTTACCTTCTGGGGGCCATATGTTTCTGTTTTATGTATGTGATTTTAATCTACTGACC
CATTACAGAGTGTGGACATGGGGGAGAAGGCAGGTATGAGCGAGGAAAGGGGAGGGCAGAGGGTAGGAC
ATCTCTGGGTTATTCTGTCTCTCCCCTAGCCATATTTGGCCCCGTGGAGTGTAAATCCCTCTGTGAAGA
GCATCCTAATGCTGAAAGTGTGTCTGAATGCAACTCAAAATGTGGCATTTGTCACTTTAAGCTAAAGAA
GGAGCTAGGCTTTGTGGAAGAAACCCTATTATGCACAAAACTTGCCCCAAGTTTCAGCTCAGAGATTGC
ATAATCCTGAAATTGATGTCCTCCTTGTCTGCTTTTTAGTAGTTTCAATTATCTCCATGGTTTACTACA
TTTTAAAGGTTGTAAACTTTTAAAGACTCATTTTGTATTCAAGGAGTTTGTTTGTTCCTTTGCTTTTTT
ATAGACCAAAGGGGCACGATTCCGTCAAGGGAAAGACTACGTTGGAGCAATCCCTGTGGATCTGAAACG
GCGCTTGGACAGCATCACCAGTAGCCAGAGCTCAGCCAGCTCTGGATTTGTGGAGGAGAAGTCCCTCAG
TGATGTAGAAGAAGAGGAAGGTACTGGCTAGTGCTTCCTGCATGCTATGGCATGCTCTTGTCAGAGCAG
ACAGGGTGATAGGGTGTTACAAGGAATTTGATCATGGGAAAAGTCCAATACTACCTCATAATTTGAAAG
AGACCTGAATTTCTATAATAGACTGCCTCCATTCTGTCTCCCCAAAAGTGAAGTGTGGAAGCCCTAGAC
TGGGAAGTGAAGCAGGGCTAGCCTGAGAAATCTGGGTAGTCCAAGTGGGCTAAGCAGTCGGCTACAACC
ACAGCAGTGTTCTTAAAATACTGGTTCAGCATTTATTAGTGAGAGAGGCCACAAGTTTTCTGGTAGTTG
ACTAGCCTCTCCATTGCCTTGGAGAGCCCCAGAGTGGTTTGCCCCACGTTGCATGCTTTACCTGTGCAA
AAGTCTTTTCATTATACCTAACCTTCTCAAAGGCAGTTTAGGAGCCATCTGTTGTTTCTACCCTACCCC
AAGCGGCTTATCAAGTCTTCCTTCCAACCATACTTCCTCAGGCGAGTCTTGATAAATATCCTGGCCTTT
ATTAAGTTATGTTTCCAGTGATATTTTATTTATTTGTTTTTATGTTTATTTTTATTTTTTGAGGTGGA
GTCTCATGCTGTTGCCCAGGCTGGAGTGCAATGGTGCGATCTCGGCTCACTGAAACCTTCGCCTTTTGG
GTTCAAGTGATTCTTGTGCCTCAGCCTTCCGAGTAGCTGGGATTACAGGTGCCTTCCACCATGCCCAGC
TAATTTTTTTTTTTTGTATTTTTAGTAAAGATGGGGTTTCACCATGTTGGCCAGGCTGGTCTCGAAC
TCCTGATCTCAGGTGATCCGCCTGCCTCAGCCTCCCAAAGTGCTGGGATTATAGGCGTAAGCCTCCGTG
CCTGGCCTGAGTGTATATTTAGTGCTCTTTTTGGGTGGAGCTGTGGTCCCAGCCTAACTTCCAGGACTT
CAGCCGGCTCCAGGACACACTGTATTTCTGCCTCCTTCAGAAGGAGCAGAGATAGCGTTGTGGATGTAG
AGATGGGTGACAGGCTGGCTCCCCTTGAGGCATAAGTCTAGAAGAATAGTGGAAGAAACCCACTCTGTT
```

-continued

```
TCCCTTGACATGAGGCTACAGAGAGAATTTGCATTTAACTCCTTTTCCTTAGAAGCTGAGAAGGTAGTG

TGAGGCTGGGACTTGGTCTAGAAGCACATGGGGAGGTGGTCTAGGCTTCATTTAGCTGGGCCCACACTG

AGTGGTGCTGCCTCTACCCTGCTCTTTGTCTTTCAAAAAACAGTGGCCAGTGAGCCAGAAACCTAAGAG

ATTGAGTTGTTGAGAAAAAGGCTCACAGCCTTTTAAATACTTACGAATTTATTACTACAACTAAGTTTT

TGTTTACTCTGGTATTTGTCTCCAGGAAAGAAGCCATAAGTCTTATCTGACCAAAGAGATGATTTTGAA

ACACCCATTTAATATCTTAGTGTTTATTTGTACCAGTTGCACTGAAGTAAATACCACCAATTTACGTAA

ATTTATCTTTCCATGTTTCTGTTATCTCTCAGGAAAAAACACCCTCCCAGGCCAGATTTAATGTATTTA

CAGCACTTTTTAAGTTTGAAAATGAATTAAATATATTTCTAGTATTTTTAGTTATCTATTGCAGATTAT

AGTTTGACTTTTGGCCTTTGTCCCAGGACAAAACCTGGAGAGAAGAGATTCAATGACCCTGAATATTGT

TGTTTTATTTTTAGAGTTCTTGATATGAAACTATTGTTTATCCCTCTGGGTACATGACAAAAACAGTG

TAAGTGGCAAATTTGGAAATGTCCTCTTTATTTCCCAGATTATCTAGGTCAGTGTTACCTTATTCTACC

TCCTGGATTTACTGGTTCAATTTGGCTAAAATGGAAAAACCAGTATTGTTCCTAAGGGGTATGATGAA

GGCTAATGATACTGGGATTCAGGAGATTTACAGAAGATAGAAGCATTGACTCTCTGCTTCTATTTCCTA

AAAACTTAACTCCCAAGTCTTAAAAAGATTATTACTCTAGCAAACTTAGAAACATCACACTAACTCATG

GAAATACTGATCTCCATCCTCCTGCCTCTTTGGACAGCTCCTGAAGATCTGTATAAGGACTTCCTGACC

TTGGAGCATCTCATCTGTTACAGCTTCCAAGTGGCTAAGGGCATGGAGTTCTTGGCATCGCGAAAGGTA

AGAAAGGTTGAGGGGAAATCAGCTATCTTTTCAGATCACAGGTTTGGAAATAAGATGTCCAGTGTCAGC

CATTGGTGCTTGTTTGGGATTGTAATTCATTCACCACTTCTACGTCTTTTAGAAGAGCTCTACTGGGGA

GGCTCTGTTTCTGCTGAGTAAGAGTGGTTAAGGAGTTCATGAAATTAAGCTGTATAATAAAGGCTTGTC

AAGCATCTACTAAGTGTGAGGCAGTCTTCTGAGCACTGAGGATACTGTGGTGAACAATCAGGCAAAGCT

CTTCACCTTCATGGAGTTTACAGTTCTAGTGGGTAGAGCAAACAATAAGCAATATAAACAAGTAAAACG

TGTTGTAGGTTAGATGAGAGTAAATGCTATGGGGAAATAAAGCAAGAAAGGGTTATAGAATACACAGGA

GCAATGCACTTGTGTATGTTTATGCTTCTCTGTGTGTGTACATCTACTTTAAACAAGGTAGACGAGGAA

GGCTTTACTAAGAACTTGACATTTGAGCAATGACCTGGAAAGGGAGGGGCTGAGCCTTACAGATATCT

TGGCATGAGAATCATTTTTAATTTATTTTACATTCATCAACATCCATCAAAAAGTATTTGTTAGGAGTA

TAATTAGAAACGAGGAAGGACAGGCTTCAGATGAGAGCGATTAAAAGAGCTAAAATTAGAAAAGTAGGC

CAAACAAAGGCTGAGATGGGGACGTGACAAGTTACAACTATTCCAAAGGTTGTAAACACCAAGCGGGGA

GCAAGGCTGGTGGCAGTGATTCCCCTGGAAAGGATAAAAGGTGTAATTTTATATTAGGTAACAATACTT

CAAATTAAGGATCAGGAAGAACTATCAGTTGACAGAATGTATTCATGCAGCTTAATGAAGAAAGAAAGA

CTTAAGTCATATTTTTTTTGTTTTTCCTAAATTAGAATGAAATCTTCAACCCATGTTTTCCCCTTCTC

ATAGCATTAAAGGCCTCAGGCTCTTTGATGTTTCTGCTAGGTAGCTCTTATGTTCTCTCTCCCAAGGGG

AAGGAGGAGAACTGGGACCTTATAGGGTTTTCCCAAAGAGAAAGGCCCTTTACACTTCTTGGAGATTAT

GACTTATTATTACCATTTTTTATGGCCGGAATTCGCCACTTAGTCAGGGTTCCTTTTGGGGACTAGGA

AGAGAATGGAAATGAATGTGGGAATGCTTTAACTTTCCTTACATCTACCAGACTATTTCTTGAATCCAC

TTGGTTGTCGGGTTAAAAAAGGAAACTTTTTGTTTGGGGGGAAAAGTCAAAAACACTGTCTGTTTTTTG

GAATTGCCAGTGTTGCTCAATTGTGCTAGATAATGTGCTTCTGAATATGCCTTGTTCAGAGGAGAGTGC

CATACAGATTTGAGGTGTGGGAAGGTCAGCAATGCCTGGCTTACATGATCACTTCTCCAATGATTTAAG

AATTCTCCTTTTGGCCAGGTGTGTTGGCTCATGCCTGTAATTCCAGCACTTTGGGAGGCCAAGGTGTGT

GGATCACCTGAGGTCAGGAGTTTGAGACCAGCCTGGCCACCATGGTGAAACCCCGTCTCTACTAAAAAT

ATAATAATTAGCTGGGCGTGGTGGCACACCTGTGGTCCCAACTACTTGGGAGGCAGAGGCAGGAGAATC
```

-continued

```
ACTTGAACCTGGGAGGTGAAGGTTGCAGTGAACTGAGATTGCACCACTGCACTCCAGCCTGGGCGAGAG
TGAGATTCCTTCTCAAAAAAAAAAAAAAAAAAAAAAAAGTTTTCTTCTAAGCCATTGATTCATTTCTT
GTGCTCCCCAAGACTCATTTTCTTACAAAATATCATGTGGAGCTAAAGCTGCCGAGTAGTAGGAAGTTA
GCTGAAGTTTGGAGGATACAGAGAAAGGAGAAACTGAGAAGCTAAAAGGAAGAGAAAGAAGTCAAGATG
AATCTCATTGTACTATTAATGCACTAGAAAATCAACCTGACTTGTGATAGGCTGAAATTGCCTTAATAG
ACCTTTATAATAACCCAGCACTTTGAAATCAGGGGAAGCCACATTGGGAATTGTTTATCAGAGCCAGTC
TGGCTTCAGCTTCATACGGAAGGGGGAAACCAACAAAGAGCACTAAACCAATGAGAGCCCCTTGTTTCT
GATTTCCGTGCATTCATTCAAAAAACAAATCCCGTTCTCGGACCTCCTTAGAATAACACGTTTTAAACC
AAATATGGGGCCAGGTAAAAGGAATGTGTGGATGTGACCAGAAACACACTCTTTTGTGTCCTAGAGGAG
CCTATTTATGATTCCATCATCATATTATAACTTAATTATTTAACTCCAAAGGCTGGGGCTGTTTATGGA
ATAAGCAGATGTGTGTCTCAGCAAAGCTCACAGACTTTTTTCCTGAAGTGTTGATAAAAGATACTAACC
CAGTCCTTGTTAATCAGTTGGCTTTCTGATGTGGGATTTTTTTTTGATGCATGAGGTCACAACAGATGT
GAAAGAGATCAGCTGTGCCGAGACCTAATGCACACATGATTCTCTTTGCAGTGTATCCACAGGGACCTG
GCGGCACGAAATATCCTCTTATCGGAGAAGAACGTGGTTAAAATCTGTGACTTTGGCTTGGCCCGGGAT
ATTTATAAAGATCCAGATTATGTCAGAAAAGGAGATGTAAGTTTCAAATATGAACCCAGTGCTTGGTTA
AGTAACAGAATTAAAACTCCTCGTAGAGAGCTTCAGGACCTGTGTTCAGGAACAGAGGAAGTTTTTTTC
TTCAGATATTTGCTAATTTGGGTTCTGAATCCTTGTCTTCTACCCCTGTAGGCTCGCCTCCCTTTGAAA
TGGATGGCCCCAGAAACAATTTTTGACAGAGTGTACACAATCCAGAGTGACGTCTGGTCTTTTGGTGTT
TTGCTGTGGGAAATATTTTCCTTAGGTAAGTCATTTCTTTTTGTCCTTCCATCCAGACTCCAAAGAGGA
AGACAAAAGTTGTCTTTTCCTCTCCTGTACTTCATGTCTATCAGGCAAAACTTCTCGGAAGCTTTGAAA
AAAAAAATAGATACATAGGTGATGAGGATGTGCAAGATTCAGGCTCAGGGTTTTCTATAAGAGAAAATC
AAATCAAAGAATGTCTCCTCCCTGTTTTATTCTAGGTGCTTCTCCATATCCTGGGGTAAAGATTGATGA
AGAATTTTGTAGGCGATTGAAAGAAGGAACTAGAATGAGGGCCCCTGATTATACTACACCAGAAATGTA
AGACTTTAAGAAGTATTCCTGTGTTCTCTTTCTTTGCTCGCAAATTCTCCTTGCCTGGAAGACTTTCCA
TTATATAGACCTTCTTCATTGCCCAGTTAGTGTCCTGCTTTTACTTTGGGGCCTTTCTTGATAATTTCA
AGCATGGAGTCATCACTTCTTGAAAAGATAGTACTTTATTATTCAAAGCAACCAGTTAGTTTTTATTAG
ATGTTGCTTTAAATGTTTTCTATACACATTGAGCCTCTGGAGTATGGGACTCTGTGTCTTACACAGTTT
TGTATCCTTATTTAGCATCTCACCTCGTCAGCTCTTTACAAATGTGTACTCATTTAAGTGCTTATTTTC
AGCATTCAGGAAGAAAGAGGCATTTAATGAAATCAGTGTTTTGCTTCTCTAGGTACCAGACCATGCTGG
ACTGCTGGCACGGGGAGCCCAGTCAGAGACCCACGTTTTCAGAGTTGGTGGAACATTTGGGAAATCTCT
TGCAAGCTAATGCTCAGCAGGTTTGTCACCTCCATCCAAGAAGCACCTACAAAGAGTACTTAGATGTCA
AGGACTTTCCTACTGCCTGAACTGTCTCATGGCTACCATGCCATCCTCTCAGCCATTGAATAATCTACT
GTATTCTTCTACATCTGAGTAATAATGCTTTTCTAAAAGCTGTAATTACCCTTTTAGACAGATAGGATT
CTAATTTATAACCCGGGAGCAGACCACTCTGATTTCTACCTACTTATCTTTTTGTTATATTTTCAAATC
CTCTTCTAAAGTTAAAACAAAGAAAAAATCTGGTTGATCCACAGAAGATCAACAATGGAAGAAATTTCA
AGAAATTTTTAATAAATTCTGCAGGCAAAAATACATCTAAGCTATGCAAAAGAGATGGTTTCTGTCTTG
GTATCATCCCAGGTTCTTATAACTTCCACTGGAAGATTTTAGAGTTGTAGTGTTTACTATTAGAATGTT
ATTTAATCTCTAGTCAATGCCTCTTACTACAATGGAAGTGAATTTCCTCTTTCTTTTCTTTTGAACAGC
TGGGGGACGATAGGTCAGCTCTATTTTTATCAATAAACCTTCCAAACATTTACAGATATCAAATAGCCC
TTTATTTCTTTTTCTTGATGCAATAATATTAAGTTGTGCAACCTTTTCTCAAAAGACCCATTTTCCTAC
CCATTTGTTGCTTTTCTTTAGACTGTCATCAGTTTTTCCATTGCCTTGAAATGTGGTGGCTAAAACTGG
```

```
ATGCCATGCCCTTTGAAGGGCTTGGCTCGTGTGGTTAGGGCTTTGTGAATGAGTGATTTTTTGTTCTAT

GTAGCTCCTTGTGTTCTGTTGTTACCTCTCTGACCACAGCCTGCTTTCTCTTCATTGTAACTGCACTTC

CCTGTGGGCTGCTTACCCATCTTGTTTTTAGTTCTCTCCTTTAATATACCTTCCATTTCAACAGCTTTT

TGTTTCTGACACATGATTTGTATTGTTGTCTTAAAGTTCTATGTTCAGATATGAAAGCCACACACCCTA

TGTAGCCAAGAAGTCCCTGTGCCCTTTGTTTTTAATGAAAAGGCACTTGAAGAACTGAAGCCATAACAA

CAGTCTTCTGTGTTTATTGTTTCAGGATGGCAAAGACTACATTGTTCTTCCGATATCAGAGACTTTGAG

CATGGAAGAGGATTCTGGACTCTCTCTGCCTACCTCACCTGTTTCCTGTATGGAGGAGGAGGAAGTATG

TGACCCCAAATTCCATTATGACAACACAGCAGGAATCAGGTACTGTATATGGCCTAACATCCCCCGGGG

GAGGGTGACTTCAAGGCCATCTCGGGAGGGGATTGGAAGTGGAAGGAAGACCTTGTCTAAGGCTGTTG

CATCCCACTTCCACATAACCTTAGCCCTGAGGTTAACATAATGGGGAATGCTCCTGGAAGAGGGCCTGG

GTAGGTGTGCTTCCTCCCATCTGTAGCCCACGCTGCTGCCACAGCATTGCCTTTAAGAATTCCAAGCCC

TGCAGCTGCAATAGCTGGAATGCCACAGTTTGCTAATTTCCAGAATAAAGAGACGAGTTTTACAAAGAC

ATCTGCATTTAAATTATCCCCGTGTATGCTTTTATTAATGTGAATTAAATGGCTTAGGAGAGATTCAGA

AAGGAAGAGTTCTGTGCTTGCATGAGAACATGCTTATGGCTCTCTGGCAAGGATACAGAAAGCCATGGG

TCTGTGTCCGGAATTAGACTGGACACTGCATCTCAGAAGCCCCTCCCACGTCTGATTTTCAGCATTTTA

TTTGCATAATGGGATGTCTGGGCTTATTTAAAACACATGCACTGCAGTCCTTTCCTGATTTGCAGAGGG

GTTCTAAAGGCAGCTTTCTTTTTTCTCTCTCCCAGCACCTGTGCATAAGGAAAGAGTTGGTGTGGTTTT

CTACAATATGATATTAAAATTGCCCTTTACTAAGGCTGGGACTACTTCATTTTGCTTTGTTTCTTTCCT

AACCCGTTTGGGTGTTTTCCTGCTTTAATGGAACCCCTGACAGCATGGGTCCAGCCTGCCAGCCCGAGT

GTGCCTGGGCTGCAGGGAGGGGCAGGGAGCTCTCTCATGTCCAGAACTTGGCCAGGTTGCCACATGGCA

GGGGATGCTAAGGAGAAACTCGTGGACAGTTTGCCCTCTAGAGTCGTGTGGGGCAGCAGAAACACTGAT

GGGAAGGAAGAAAGCTTAGAAGCCAGCAAGACAGCTGACCGTTCCATTGAAGTCAAAAGCATTAGGCAT

ATTTTTAAAGAACTTTGCCGTATATTATCAGATGTTGCCCACATCATGACACTCAGAGTCAGGCAAGGT

AGAAACAATGATCTTTTTTTTTGATGTATTATTGAACATGAGGCTCAGTTCTATTACCTGAGGGCAGTA

CAAACTTGTAGTTAAAGATCAGGTATTAGAGTCAGATAGAAATGAGTAGGACCCCCAAGTCTGTCTTGT

AGCAGCTGTGCAACTTGGGGCAAATCATCTACCCTCTGCCTCAGTTTCTTTATCTGTGAAATGAGACAA

GGTCAGTGGTGCTGTTTGAAAATGGCTGTTTTGAGAGTTATAAGATATAATCTATTTCTAAGCACCTGG

CCCTTGAAAGCACTCAGTAAAAGATACCTATTAAGTGAGCTGCTTAAAATCACATCCTTGAGATGAATC

CAGTTCCTCTGACCCCTAAGTCCATGTTGTTTCCTCCCATGCCAAGGAGGGCCCTCAGAGAGAAACAGT

AATGAGATGAGACTACAATTCCACTCCTGTGTTTACACATTTCCAGTTCAAGTTGAGCTGGCCTTTTAG

TGTGACAGTTGTTCCCACACACCATTATTGCCTCCCCCTTTATCAGAAAGCCATTTGATCATGAACTAC

ATTCCATGTGTTTTCTGTGACCAAGTAGAGTGATGATCCGAGTCGGCAGCCTCCTGGCTCACCGGGTGC

TTTGCATATGGTGCTGAGCAGGAGAAGAAATCATGTTTGTGTAATGGAAGCACCAAATACGATGTTGGA

TATATAGAAGGGCTGCTAACGTTTATCCCCAGAAGCGTGGACAAATGTGACACCACACTCCCAGCACAG

GCCTGGCTCCTATTTTCTGTCTGTGATTTTTGAATTGGTTTTTCCAGCCCAGTTTCTCTTTTATCCAGC

CATAATTTGAAAAATAAATGGAAATTGGAATCTTTTGTCTGCATCTCCTCTCCACCTCCTCCACCTTT

TTTCCTTTCTATAAAATAAAACTCACGGTCACATTTTAATCATCTGGTTTTGAAGAAAAGCAGATAGAG

GCATTTGCACACGGCATGCTTCATTCTGTTGCTCTCCTGGGGTTCTGTTTCTCTGGGGAGAATGAGTTG

AGGCTGGGGTACTTCTCAGGGAGCTTGTTCTATCCTCTTACGCATTTCTGGCCAAGTACAAAAGCTGAG

CAGTCTTTCTCCTTCTAATTTTCAATTCTATTGCATTATAAATAGAGTTGGACAGAGATATCACTGTGG
```

-continued

```
GAGCTAGCTTCATGATTTGTTGCCCCTTTAAACCATTTGAAAAATATTTACTTAGCATTTATTTAGAGA

AAAGGCTGAGAAGTGTGTGGGGGAGGGACCACTCATGTCTAGACTTAGCTTTGCCTCTAATTTCCCCTG

TGGACCAGCTCTGGCCTCAAGTTTGCATGCTTCCTGCAAGAAAACACATACTTGCTGGGCTCATCTTTC

TTTGAGGGCAGTTTGGGGACCATCGGCAATTGCTCTGTCATTTTCCCTGGGAGTTTCACCTCACACATC

AAGCAGCTTATCAAAAATTTCTTTGCAGTTCTCTCTTAGAGAAAGGTTTTGGTACATACCATTTTCTTC

ATTTTGTAATTGTTAGGGATGATTAAATGGCCCTTGTAGATTGATGCTTGGGGCAGCCTGCTAGCTAGG

TATTCCTGAGTTTGGCTCTACCATTAGACTGTTTGCAGTGGGACTGTCCTTTCTGCACTTTTTGTCTGT

TTCATACCCCGTACTTACACCCCTGACCCTGCTACTGCATGATCAGTGCATGCATGACAAGAGAACAGT

GCTGTGCACATACTGGGTGCTTAATAATGGCTTGAACAATTGTGTCTGCTGTTTTCTTCTTTCTTTTCC

CTCCTGATACTCTTCCAAGGGAGTCTGTATGGAGTAGAGTAAAACAAAACAAAAACTTCACATGGGCTT

TAGTGTCTGAAGGCCTAAGTTTGAGTCCCAGTTCTACCTTTTATTAGCCATTTTCTCCCTAATCCTTGA

CTCCCTCATCTCCAAAGGGGAAATAGTTAAAAGACCTGTTTCTCCGTCTTAGGAGAAACAGATGCACCA

TTGTCTGTGAAAATGCTTTGTCAATCATGAGAGGATCATGCCATTTAAAAAATTACTGGATTAAGAATT

TAAGGAGCTGTCCTTTCTAAGGCAGCTGAATTATTGTCCAAACTCGCCAACCCTAGTTGATTCTATCCC

CTAGATATCTCTAGAATGAGCCCATGTCTCCAAACCTCATGGGCATTCCCTTTTTCTAGCCAAGCTGCC

TTTCTTTCTCCTGAAGAAGTGCAGTATTTGTCTCTTGGGTCTTATGCCTCTAGTCTTATTCTTTTCAAT

CCAGAGTCAATTCTCTAAAGGGCATATCTGATCTTGTCAATCCCATGCCTAAAATCCTTCAGTGGCTCT

TCATTGCCCTCAAAATAATAATCCAAACATTCCAGTTATGTGATTTTGGATAAGTTCCTCAAATTTTCT

ATGCCTTGGTTTCCTCATCTGAAGAGTTGGGATAGTAATACTCACCCCTAGAGAGGTACCGTGGTGAAC

ACATCATGAGATGCTGCTTAGACAGCTTCTGGCACAGTGTCAGGCTTGCGGCAGATTATCAGTGAGGGC

TTCCTGAACAAGTGAATGCAGGAATGATTGACTACGGTACCAGTAGTGTTTGACAACTGTTACTTTTAG

GGGTTGGACTTAGAAAGTAGGCTTTGCTTGCACCCTGTGTATCATATCCTCTTAACTTGTGGAGTTTCC

TGAGTGAGGATGTCACCGGAAAATCTCATTCTCTCCTCTCTCTATAGGGAGGAACCAGCCTCTTGGGGT

AGGGGAGAGAGAATTAATTTCCATTCTTCTCCTTTGGCCCAAGGTCTATGCAGCATGTTCCAGAAGTCT

GCTTGTAGTGGGAAGTAGGCTGGTATAGGAATGAAGAATGTATTTTCTGTCTCGGTGGGCCCTTCCAGT

GAATAGGACTTCCCTTCCCTCCACTTGGGCTGTAAGTGATTTTGATAGCATCAACTAGACTCACCCAAA

GCCACACGGCCGGGAAGGAGCATTCTCAAGAAGGAGAGGATCTGTTGTTCAACAAGTCTTATCTTTGG

ACTCCTGAAGGAAGCTTTGGAAGTCAAAGGAGAAAAATGAGCTTTGTTTGAAGAGGGCATTATTCTTCC

TAAGAGCAATAAGCCCAACATTCTCTATGTCATTCATCTTCCCAACATCCCTGTGAGCTGGGGAGGGAG

TGCTACTGCCAACACATCTTATAGATGGGACAAGAGGGTCACAGAAATATTCATGACTTTCTCAAGTTT

CTGCAGTCAGTGGTAGACTCTGAAATAGGCAAAATATCTTGTTATTCTCAAACCACTGCTCTTTCCTGA

GACAGCAACTCTGGGGGCGAAAACGAGGGGACAGTGAGACTCAGCCCACCTTCTCTTTGCACACCAAGC

CTCTGTTACATGGAGGAGGAAGAGGTTGTCTTCAAATCACTGCTGGGTTCAGTATCCTTTAAGGAGACC

TTCAGATGTTTCCTCTGCCTATCTTTCATTGAATGGTTGCTCTGTGAGCATTATCCAGAAAAACTTTCC

CAGGAGATGGCCAGACAGATGTGAAACACTCAGTAATATATCCAGAGCTCGATGGAGGAATCCCATGCA

ATCAGGAAGCCAAGTAGAAGGCAGTTGATCACTCCATCTGCTGTTGTTGTCTTTAGTCCAGAACTGGAC

CTCAGAAGTAGGATTCAAAAGAACAGGCTCATCGAGACTCCTCAGTTATATTATACTTTTAAATGTACT

TTCTCAGGAAATTAAGCCTTCCATGTGTGCTAGCAGAGAAAGATTTTTATTTTGTTTTGTTTTTCTAAA

GGATGTTTTGAAGGTTGCTATTAAGTTTGTGGTTGAAAGATAATGAACTTAGGTAGCCGATCTGCAGTC

AAATATACCACCACTAAAATATAAATATTTGTTCTTTTGCAGTCAGTATCTGCAGAACAGTAAGCGAAA

GAGCCGGCCTGTGAGTGTAAAAACATTTGAAGATATCCCGTTAGAAGAACCAGAAGTAAAAGTAATCCC
```

```
AGATGTAAGTACGTCTTTTAAAAATAGTCTTAGAAATAATACAAAGGATGAAACACTAGCTAGATAAAT

ATTAGCCTAAGCATTAAAGTTTTGGAGCCTCATTAGAAGGCTGCCCTCGAGTGTGTGTATCATGGGGTC

ATTATGGAGATGGAACTTTGTTTTTTTCATAAGTAAAGCCCTTGGTCCAAGGTTCAAGACAGTGTAGCT

TTCTGACCAATTTCACTAAAGTGCAAGTAGTGTCATAGTGAAGCAGCGATGGTAACAGGCATTCTCAG

CTGCTGATTTGTAAATTTTCTCTTCTCCCTGGCCTGTGTCTACTCATAGGAAGCAGTTGCTTCCTTTTG

TAGCTTGGACAATTTGTGGCTATGATACCTTTATGTTCTTCCACAGGACCTTATTTGATAGACATGATA

GATGGGTTGAGAAATCAGCTTAATTAAATAGTTGGTCATTTTATATGCTCAATTAACTGTGCCATCTCA

TTGTCTCTTAAAAAGGACAACCAGACGGACAGTGGTATGGTTCTTGCCTCAGAAGAGCTGAAAACTTTG

GAAGACAGAACCAAATTATCTCCATCTTTTGGGTAAGACTCAGCCATATTAAAAAGACAAATTTCAATA

GGAATTTTTGGAAGGAACTTAGGACTTTCAGTGTAAGTGCAGAATTTTCCCTATGGGGTCTTTGTTGGT

TGGAGAAATTAGCATCAATTTAACAAATAAAGAATGGAAACTAACCACACAATAAAATTAAGTGATAAA

TCTAAAAATAATCTGAAATAAATTAGAGAATTTGGTCAATTTTTATGAGAATTCATGAATACTAGGGAA

TTTCTGTGTATATTTACTGTGGTCAGTAATGGCTAAATGAAAAGGTGATTGGATGTGATCCGTAAAGC

TGTCAATATGATTACAATCTTTGTGGACTCTGAAGAATTTTTAAGTCTGTATACAAATGGGTGCATCTG

TGCTTAAGAAGTATGATATATAAATAAGCCAATATCTATTTGTTTGAGACATTTAAATATTATTGTCTG

AATTCGAAGTATTTCATTGTGAGAAAAGTATTAAAATTAGTTTTAAATATAATCTCCCTTCTATGGCTC

AGTAGGAATTTGTAGGTGTCTTGAATACGTGTACGTTCTCTTAACATAACAAATCAATGAAAATCTATA

TTTATAAGAATAATAGAATAAGTGTAGTTATGTATTTGCTGGAGTTTATTTGCTAGAGTATTCTTACCT

AAAGGTAAGAATAGAGGAGGTTTTGATCTGCTTATAATCTTTTATATAAAATGGGAATACTCATGGGTT

TTTGAATAATGCTCATACCAAAAAGAAAACAAACAAAAAAAACCCCAACATATTAAAAGGTGCCATTGT

GCTATTTTATTGTTTTCTTTAAGGCCCAAGGTAAGAAATTGTGAAAGTCAATGATATGTTTCATTCATT

GATTCAAAAAATGTTTATTCGGCAAGTATCATGTGCAGAGCACCATGCCATTGCTTGAGACACCTACAT

TAGTTTTGTTGGGGTTGAATTGAAAGAAAAAATTGTATTTCTCATTATTTGAAGTAACTTTTAAACTAT

GTATAAACACGAGTTACTAAAATTCCCTTTTGCAGTTTTAACATGAAGAAGTTGGGGAAAACACCTATT

ACCGGGAAAAAACACCTTAGAATGGCTTGTGAAAGTGTAAATCCTGAAGTTTTAGATCAACACAGCCTG

CATTTCTAGGCTTTGACATGATTACCGTCTGTCAGGATTCCATGCCATTGAAAACATTTTCTAGTTGCT

GCTGAGTGACAGGGGTTCTCAGTCCTTCCAAGGAATGTGGTTTTGATGAGTAAAAAGCAGCGTTTGATA

TGTCTGGCTTGACTGCACACATGCTTCAAGTTATTAAAGTTTAAAGTTGCTCAAGAGCTTTATTACAAC

CATACACATGCCCCGTAATTCCCAAATTGCCACAATAGGAAAAGCACAAGTGAAATTTAAGAACATCCC

AATTTCCTTGAATATCATGCAAGTGGCCCTTTGGCGCCTGTCACTGTATACAAATTTGTCAATCTGCGA

GGCCATAAACATGTTCCATCAGTTGGGGCCTTTGCATAACTCGAGAGAACTGCCTTTCATCTCATTTGA

GGCTTGAAAGACTTGGACCTGAGTAAGAGGACTTATCTGCAACTACTAATTCATGCGAGTACCTGAAAA

TAGACCTTGTCCCTGTAAACCTGCTATGCTGATTAACAACTGGGAGAGATACGGGGCTGCGGTCTCCAG

GGAGATGGCAGCCATATGGAGTTGGGAATGGGGTGAGGGTAAAAAGCAAAGAATTGTCTTCTCTCTGC

CAACTCCTTTGTTTGCCATTTCTTCTGCAGTGGAATGGTGCCCAGCAAAAGCAGGGAGTCTGTGGCATC

TGAAGGCTCAAACCAGACAAGCGGCTACCAGTCCGGATATCACTCCGATGACACAGACACCACCGTGTA

CTCCAGTGAGGAAGCAGAACTTTTAAAGCTGATAGAGATTGGAGTGCAAACCGGTAGCACAGCCCAGAT

TCTCCAGCCTGACTCGGGGACCACACTGAGCTCTCCTCCTGTTTAAAAGGAAGCATCCACACCCCCAAC

TCCTGGACATCACATGAGAGGTGCTGCTCAGATTTTCAAGTGTTGTTCTTTCCACCAGCAGGAAGTAGC

CGCATTTGATTTTCATTTCGACAACAGAAAAAGGACCTCGGACTGCAGGGAGCCAGTCTTCTAGGCATA
```

-continued

```
TCCTGGAAGAGGCTTGTGACCCAAGAATGTGTCTGTGTCTTCTCCCAGTGTTGACCTGATCCTCTTTTT

CATTCATTTAAAAAGCATTTATCATGCCCCCTGCTGCGGGTCTCACCATGGGTTTAGAACAAAGACGTT

CAAGAAATGGCCCCATCCTCAAAGAAGTAGCAGTACCTGGGGAGCTGACACTTCTGTAAAACTAGAAGA

TAAACCAGGCAATGTAAGTGTTCGAGGTGTTGAAGATGGGAAGGATTTGCAGGGCTGAGTCTATCCAAG

AGGCTTTGTTTAGGACGTGGGTCCCAAGCCAAGCCTTAAGTGTGGAATTCGGATTGATAGAAAGGAAGA

CTAACGTTACCTTGCTTTGGAGAGTACTGGAGCCTGCAAATGCATTGTGTTTGCTCTGGTGGAGGTGGG

CATGGGGTCTGTTCTGAAATGTAAAGGGTTCAGACGGGGTTTCTGGTTTTAGAAGGTTGCGTGTTCTTC

GAGTTGGGCTAAAGTAGAGTTCGTTGTGCTGTTTCTGACTCCTAATGAGAGTTCCTTCCAGACCGTTAC

GTGTCTCCTGGCCAAGCCCAGGAAGGAAATGATGCAGCTCTGGCTCCTTGTCTCCCAGGCTGATCCTT

TATTCAGAATACCACAAAGAAAGGACATTCAGCTCAAGGCTCCCTGCCGTGTTGAAGAGTTCTGACTGC

ACAAACCAGCTTCTGGTTTCTTCTGGAATGAATACCCTCATATCTGTCCTGATGTGATATGTCTGAGAC

TGAATGCGGGAGGTTCAATGTGAAGCTGTGTGTGGTGTCAAAGTTTCAGGAAGGATTTTACCCTTTTGT

TCTTCCCCCTGTCCCCAACCCACTCTCACCCCGCAACCCATCAGTATTTTAGTTATTTGGCCTCTACTC

CAGTAAACCTGATTGGGTTTGTTCACTCTCTGAATGATTATTAGCCAGACTTCAAAATTATTTTATAGC

CCAAATTATAACATCTATTGTATTATTTAGACTTTTAACATATAGAGCTATTTCTACTGATTTTTGCCC

TTGTTCTGTCCTTTTTTTCAAAAAGAAAATGTGTTTTTTGTTTGGTACCATAGTGTGAAATGCTGGGA

ACAATGACTATAAGACATGCTATGGCACATATATTTATAGTCTGTTTATGTAGAAACAAATGTAATATA

TTAAAGCCTTATATATAATGAACTTTGTACTATTCACATTTTGTATCAGTATTATGTAGCATAACAAAG

GTCATAATGCTTTCAGCAATTGATGTCATTTTATTAAAGAACATTGAAAAACTTGAAGGAATCCCTTTG

CAAGGTTGCATTACTGTACCCATCATTTCTAAAATGGAAGAGGGGTGGCTGGGCACAGTGGCCGACAC

CTAAAAACCCAGCACTTTGGGGGGCCAAGGTGGGAGGATCGCTTGAGCCCAGGAGTTCAAGACCAGTCT

GGCCAACATGGTCAGATTCCATCTCAAAGAAAAAAGGTAAAAATAAAATAAAATGGAGAAGAAGGAATC

AGA
```

Human ICAM2 promoter sequence (bold font indicates sequence described
in Cowan et al., J Biol Chem. 1998 May 8;273(19):11737-44).

(SEQ ID NO: 13)
```
AGACTGACCCCATTCTCTGTCTGTGCCTGGGTTGCTGGGGACTATTATGGGATGCATTTCCTGAGGCTC

TGGGCCTCAAGTTGGCCCTGAATCAGCTGAGTCAAGATCAAGTCTAGGTTGAAAACTGAGTGAGGGCCA

GGTGCGGTGGCTCAGGCCTGTAATCCCAGCACTTTGGGAGGCCAAGGCAGGCAGATCACCTGAGGTCAG

GAGTTCAAGACCAGCCTAGACAACATGGTGAAACCCCATCTCTATTAAAAATACAAAATTAGCTGGGTG

TGGTGACGCGATCCTGTAATGTCAGCTACTCTGGAGGCTGAGGCAGGAGAATTGCTTGAATCTGGGAGG

CAGAGGTTGCAGTGAACCAAAAATTGTGCCACAGCACTCCAGCCTGGGCGACAAGAGTGAGACTCCATC

TCAAAAAAAAAAGAAAAAGAAAAAGAAAAGAAAACTGAGTGGGATGTGAAGGTTTATGCAGAATTGCA

CCAGGCATTTAGCAGGAGAAGCTCAAATTGCCCTCCAGGCTTCCTTAGAAAAGCCCAAGTCACTGTCCC

CTTTTGCTATGGTAACTGCAAGTCCTGGACAGGTCCTGGCCTTTGGATGCTTGTCTCCCAGGCATGACT

CCAACAATGCATCCCATGGGATTTGGGGTTCCCCAGATCTGGGGCTTGTAGGCCTGACTCTCCCCTGTG

CACACGTCTCATACACGCATGCGTGCACCCATTGCCTGCCCCGCCCCTTGCACAGGGAGTCAGCAGGGA

GGACTGGGTTATGCCCTGCTTATCAGCAGCTTCCCAGCTTCCTCTGCCTGGATTCTTAGAGGCCTGGGG

TCCTAGAACGAGCTGGTGCACGTGGCTTCCCAAAGATCTCTCAGATAATGAGAGGAAATGCAGTCATCA

GTTTGCAGAAGGCTAGGGATTCTGGGCCATAGCTCAGACCTGCGCCCACCATCTCCCTCCAGGCAGCCC

TTGGCTGGTCCCTGCGAGCCCGTGGAGACTGCCAGAGATGTCCTCTTTCGGTTACAGGACCCTGACT
```

REFERENCES

1. Senger, D. R., et al. Tumor cells secrete a vascular permeability factor that promotes accumulation of ascites fluid. Science 219, 983-985 (1983).
2. Shima, D. T., et al. Hypoxic induction of endothelial cell growth factors in retinal cells: identification and characterization of vascular endothelial growth factor (VEGF) as the mitogen. Molecular medicine 1, 182-193 (1995).
3. Muller, Y. A., et al. Vascular endothelial growth factor: crystal structure and functional mapping of the kinase domain receptor binding site. Proc Natl Acad Sci USA 94, 7192-7197 (1997).
4. Holmes, K., Roberts, O. L., Thomas, A. M. & Cross, M. J. Vascular endothelial growth factor receptor-2: structure, function, intracellular signalling and therapeutic inhibition. Cell Signal 19, 2003-2012 (2007).
5. Folkman, J. Angiogenesis in cancer, vascular, rheumatoid and other disease. Nat Med 1, 27-31 (1995).
6. Williams, R., et al. Epidemiology of diabetic retinopathy and macular oedema: a systematic review. Eye (Lond) 18, 963-983 (2004).
7. Fraser-Bell, S., Kaines, A. & Hykin, P. G. Update on treatments for diabetic macular edema. Current opinion in ophthalmology 19, 185-189 (2008).
8. Mintz-Hittner, H. A., Kennedy, K. A., Chuang, A. Z. & Group, B.-R. C. Efficacy of intravitreal bevacizumab for stage 3+ retinopathy of prematurity. N Engl J Med 364, 603-615 (2011).
9. Stahl, A., et al. The mouse retina as an angiogenesis model. Invest Ophthalmol Vis Sci 51, 2813-2826 (2010).
10. Chakravarthy, U., et al. Alternative treatments to inhibit VEGF in age-related choroidal neovascularisation: 2-year findings of the IVAN randomised controlled trial. Lancet 382, 1258-1267 (2013).
11. Suzuki, M., et al. Predictive factors for non-response to intravitreal ranibizumab treatment in age-related macular degeneration. Br J Ophthalmol 98, 1186-1191 (2014).
12. Deyle, D. R. & Russell, D. W. Adeno-associated virus vector integration. Current opinion in molecular therapeutics 11, 442-447 (2009).
13. Pillay, S., et al. An essential receptor for adeno-associated virus infection. Nature 530, 108-112 (2016).
14. Jinek, M., et al. A programmable dual-RNA-guided DNA endonuclease in adaptive bacterial immunity. Science 337, 816-821 (2012).
15. Duan, Y., et al. The Clustered, Regularly Interspaced, Short Palindromic Repeats-associated Endonuclease 9 (CRISPR/Cas9)-created MDM2 T309G Mutation Enhances Vitreous-induced Expression of MDM2 and Proliferation and Survival of Cells. J Biol Chem 291, 16339-16347 (2016).
16. Swiech, L., et al. In vivo interrogation of gene function in the mammalian brain using CRISPR-Cas9. Nature biotechnology 33, 102-106 (2015).
17. Tabebordbar, M., et al. In vivo gene editing in dystrophic mouse muscle and muscle stem cells. Science 351, 407-411 (2016).
18. Chitranshi, N., Gupta, V., Kumar, S. & Graham, S. L. Exploring the Molecular Interactions of 7,8-Dihydroxyflavone and Its Derivatives with TrkB and VEGFR2 Proteins. Int J Mol Sci 16, 21087-21108 (2015).
19. Dai, C., McAninch, R. E. & Sutton, R. E. Identification of synthetic endothelial cell-specific promoters by use of a high-throughput screen. Journal of virology 78, 6209-6221 (2004).
20. Ellis, B. L., et al. A survey of ex vivo/in vitro transduction efficiency of mammalian primary cells and cell lines with Nine natural adeno-associated virus (AAV1-9) and one engineered adeno-associated virus serotype. Virology journal 10, 74 (2013).
21. Grieger, J. C., Choi, V. W. & Samulski, R. J. Production and characterization of adeno-associated viral vectors. Nat Protoc 1, 1412-1428 (2006).
22. Huang, X., et al. Editing VEGFR2 Blocks VEGF-Induced Activation of Akt and Tube Formation. Invest Ophthalmol Vis Sci 58, 1228-1236 (2017).
23. Connor, K. M., et al. Quantification of oxygen-induced retinopathy in the mouse: a model of vessel loss, vessel regrowth and pathological angiogenesis. Nat Protoc 4, 1565-1573 (2009).
24. Lambert, V., et al. Laser-induced choroidal neovascularization model to study age-related macular degeneration in mice. Nat Protoc 8, 2197-2211 (2013).
25. Maguire, A. M., et al. Safety and efficacy of gene transfer for Leber's congenital amaurosis. N Engl J Med 358, 2240-2248 (2008).
26. Bainbridge, J. W., et al. Effect of gene therapy on visual function in Leber's congenital amaurosis. N Engl J Med 358, 2231-2239 (2008).
27. Hauswirth, W. W., et al. Treatment of leber congenital amaurosis due to RPE65 mutations by ocular subretinal injection of adeno-associated virus gene vector: short-term results of a phase I trial. Human gene therapy 19, 979-990 (2008).
28. Jessup, M., et al. Calcium Upregulation by Percutaneous Administration of Gene Therapy in Cardiac Disease (CUPID): a phase 2 trial of intracoronary gene therapy of sarcoplasmic reticulum Ca2+-ATPase in patients with advanced heart failure. Circulation 124, 304-313 (2011).
29. Gaudet, D., Methot, J. & Kastelein, J. Gene therapy for lipoprotein lipase deficiency. Curr Opin Lipidol 23, 310-320 (2012).
30. Gaudet, D., et al. Efficacy and long-term safety of alipogene tiparvovec (AAV1-LPLS447X) gene therapy for lipoprotein lipase deficiency: an open-label trial. Gene Ther 20, 361-369 (2013).
31. Bergers, G., et al. Matrix metalloproteinase-9 triggers the angiogenic switch during carcinogenesis. Nat Cell Biol 2, 737-744 (2000).
32. Giraudo, E., Inoue, M. & Hanahan, D. An aminobisphosphonate targets MMP-9-expressing macrophages and angiogenesis to impair cervical carcinogenesis. J Clin Invest 114, 623-633 (2004).
33. Zhang, F. CRISPR-Cas9: Prospects and Challenges. Human gene therapy 26, 409-410 (2015).
34. Cox, D. B., Platt, R. J. & Zhang, F. Therapeutic genome editing:
prospects and challenges. Nat Med 21, 121-131 (2015).
35. Ruan, G. X. & Kazlauskas, A. Axl is essential for VEGF-A-dependent activation of PI3K/Akt. EMBO J 31, 1692-1703 (2012).
36. Lei, H., et al. RasGAP Promotes Autophagy and Thereby Suppresses Platelet-Derived Growth Factor Receptor-Mediated Signaling Events, Cellular Responses, and Pathology. Mol Cell Biol 35, 1673-1685 (2015).

37. Saint-Geniez, M., et al. PGC-1alpha regulates normal and pathological angiogenesis in the retina. Am J Pathol 182, 255-265 (2013).
38. Lei, H., Romeo, G. & Kazlauskas, A. Heat shock protein 90alpha-dependent translocation of annexin II to the surface of endothelial cells modulates plasmin activity in the diabetic rat aorta. Circ Res 94, 902-909 (2004).
39. Kawamoto, A., et al. Therapeutic potential of ex vivo expanded endothelial progenitor cells for myocardial ischemia. Circulation 103, 634-637 (2001).
40. Giani, A., et al. In vivo evaluation of laser-induced choroidal neovascularization using spectral-domain optical coherence tomography. Invest Ophthalmol Vis Sci 52, 3880-3887 (2011).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating an ocular disease associated with angiogenesis in a subject, the method comprising administering to the subject a CRISPR/Cas9 editing complex comprising a guide RNA targeting a VEGFR2 gene, wherein the guide RNA targets SEQ ID NO:14, and wherein the administering is using an adeno-associated virus 1 (AAV1) vector.

2. The method of claim 1, wherein the AAV1 vector comprises
   (i) a sequence encoding *Streptococcus pyogenes* (SpCas9) under the control of an endothelial cell-specific promoter, and
   (ii) a sequence encoding the guide RNA targeting the VEGFR2 gene.

3. The method of claim 2, wherein the endothelial cell-specific promoter is an ICAM-2 promoter.

4. The method of claim 1, wherein the AAV1 is administered by intraocular injection.

5. The method of claim 1, wherein the subject has proliferative diabetic retinopathy (PDR), retinopathy of prematurity (ROP), or wet age-related macular degeneration (AMD).

6. A composition comprising:
   (i) an AAV1 vector comprising a sequence encoding *Streptococcus pyogenes* (SpCas9) under the control of an endothelial cell-specific promoter, and
   (ii) a sequence encoding a guide RNA targeting a VEGFR2 gene, wherein the guide RNA targets SEQ ID NO:14.

7. The composition of claim 6, wherein the endothelial cell-specific promoter is an ICAM-2 promoter.

8. The composition of claim 6, wherein the AAV1 is formulated to be administered by intraocular injection.

* * * * *

SEQUENCE LISTING

```
<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: mK22 target sequence

<400> SEQUENCE: 1
gtcccggtac gagcacttgt                                               20

<210> SEQ ID NO 2
<211> LENGTH: 23
<212> TYPE: DNA
<213> ORGANISM: Artificial Sequence
<220> FEATURE:
<223> OTHER INFORMATION: control sgRNA sequence

<400> SEQUENCE: 2
tgcgaatacg cccacgcgat ggg                                           23

<210> SEQ ID NO 3
<211> LENGTH: 32
<212> TYPE: DNA
<213> ORGANISM: Artificial Sequence
<220> FEATURE:
<223> OTHER INFORMATION: PCR primer forward

<400> SEQUENCE: 3
cgtctagagt agaacgagct ggtgcacgtg gc                                 32

<210> SEQ ID NO 4
<211> LENGTH: 29
<212> TYPE: DNA
<213> ORGANISM: Artificial Sequence
<220> FEATURE:
<223> OTHER INFORMATION: PCR primer reverse

<400> SEQUENCE: 4
ggaccggtcc aagggctgcc tggagggag                                     29

<210> SEQ ID NO 5
<211> LENGTH: 23
<212> TYPE: DNA
<213> ORGANISM: Artificial Sequence
<220> FEATURE:
<223> OTHER INFORMATION: top oligo

<400> SEQUENCE: 5
accgtcccgg tacgagcact tgt                                           23
```

```
<210> SEQ ID NO 6
<211> LENGTH: 20
<212> TYPE: DNA
<213> ORGANISM: Artificial Sequence
<220> FEATURE:
<223> OTHER INFORMATION: sequencing primer

<400> SEQUENCE: 6
ggactatcat atgcttaccg                                              20

<210> SEQ ID NO 7
<211> LENGTH: 20
<212> TYPE: DNA
<213> ORGANISM: Artificial Sequence
<220> FEATURE:
<223> OTHER INFORMATION: PCR primer forward

<400> SEQUENCE: 7
gctcctgtcg ggtcccaagg                                              20

<210> SEQ ID NO 8
<211> LENGTH: 20
<212> TYPE: DNA
<213> ORGANISM: Artificial Sequence
<220> FEATURE:
<223> OTHER INFORMATION: reverse

<400> SEQUENCE: 8
acctggactg gctttggccc                                              20

<210> SEQ ID NO 9
<211> LENGTH: 23
<212> TYPE: DNA
<213> ORGANISM: Artificial Sequence
<220> FEATURE:
<223> OTHER INFORMATION: off target sequence

<400> SEQUENCE: 9
ctcacggttg gagcacttgt agg                                          23

<210> SEQ ID NO 10
<211> LENGTH: 22
<212> TYPE: DNA
<213> ORGANISM: Artificial Sequence
<220> FEATURE:
<223> OTHER INFORMATION: forward primer P25F

<400> SEQUENCE: 10
agcttcattc agtgtctctg gg                                           22

<210> SEQ ID NO 11
<211> LENGTH: 23
<212> TYPE: DNA
<213> ORGANISM: Artificial Sequence
<220> FEATURE:
<223> OTHER INFORMATION: reverse primer P25R

<400> SEQUENCE: 11
gggtatttgt aaggtgctgt tga                                          23

<210> SEQ ID NO 12
<211> LENGTH: 47337
<212> TYPE: DNA
<213> ORGANISM: Homo sapiens
```

<400> SEQUENCE: 12

```
actgagtccc gggaccccgg gagagcggtc aatgtgtggt cgctgcgttt cctctgcctg      60
cgccgggcat cacttgcgcg ccgcagaaag tccgtctggc agcctggata tcctctccta     120
ccggcacccg cagacgcccc tgcagccgcg gtcggcgccc gggctcccta gccctgtgcg     180
ctcaactgtc ctgcgctgcg gggtgccgcg agttccacct ccgcgcctcc ttctctagac     240
aggcgctggg agaaagaacc ggctcccgag ttctgggcat ttcgcccggc tcgaggtgca     300
ggatgcagag caaggtgctg ctggccgtcg ccctgtggct ctgcgtggag acccgggccg     360
cctctgtggg taaggagccc actctggagg aggaaggcag acaggtcggg tgagggcgga     420
gaggacctga agccagatc taactcggaa tcgtagagct ggagagttgg acaggacttg      480
acattttgcg atctttcatt taccagtggg gaaactgagg ctcagagact ggcccaagat     540
tacccagcga gtctgtggtc gcctgtgctc tagcccagtt cctttttctag gactctggtt     600
tgcgacaggg acctcggctg gagcatgtcc tgagatgccg acacccctc aggctcttgg      660
gaggctgggg tgggaaggcg cctggggttg gcaggcagga ggtgcctccg caggcgagaa     720
caggcggtga aaagttgtct ggctgcgcgc aacatcctag tccgggcccg gggaagaaaa     780
ccttgccgga atctcaggcc gggtctcccg gatcggacgg tacactcggt tctgcctctt     840
tgcgggaccc ggcccgttgt tgtcttcatg ctcgaacaca cttgcacacc actgtgtgaa     900
gtggggtctg gagcggagag aaacttttt tccttccttg gtgcaggacg ccgctctcct     960
tgcagagcga agaagggggg gaatagggac ttgtcctggg ggctttgaca gcttccccaa    1020
gggtctccaa gtaacagcca actgtcctgc gtaaagcatt gcacatcttt caaagcgctg    1080
tggtccttgg tgtaagcgca tagtcagaag ttcaagctcc gaaaaccttt cctgtgggcc    1140
ttggtaccta gctttagtgc cattccttcc tctccctgcc gcctaaaatt tccgtctcct    1200
tcaattagga acacacacgt tcttcatgca atagctgtct gtcttttctt cctcactttc    1260
ctttctctct caacccctta gataatattt cttttcctgca gccagtttgc tgatatccag    1320
atttccaccc tttgcagggt gagaaagggg aaagggtcag agaaagaaaa aaaaaagtc     1380
gaataattca gggaaaaaaa tttcttactc cctaagacaa gaatcacatg tcttagaaga    1440
cactcacacc cacatacagt accaggatca tctgtccatg gttactgaat tttctttata    1500
atgacttggt tcaacgggtc cagtccacca tggacactc tttgtcccag acaagccctc     1560
tctctccccc tttctgggca gagaatgaag gtctggaaca tgtggttgct ctgtattcca    1620
caaagaagtg agttgctttt aagcctgggg tgtttcctag cgtagtagta acggcaggcc    1680
ggtcgccctg aatataatgg tgaacttgcc cttttggagt gcattacttg cttaattgga    1740
ttgggctgta attggtgcca tcaaattcta gagacagagg cactgttgtt tttccttccc    1800
gtctttgagc tggaagggta acagtgcaca aattaattaa tattggttat gggatttgaa    1860
catagaaggg cttttattg agtagtagca tgtgtacctc ttacagttat ttctttagaa    1920
ctttctgaag agtccagctc aagcttgcca atgaaaacga atgacattta atggagcaaa    1980
aacaaaaaac aaaaaactat gttggtctac aaatatgaat ttgaagttat tgagagcctt    2040
gttgaataga ttttgttgt aaacgtgtct ctagaatagt atggcatagt ctcagcttcc     2100
tatgaatgaa ggacatacct tttcttttt aaaatatttg ttacacagga aagtgtgtct     2160
agaatgtgat ctgtggcaat aaattatgag agaccttcaa gagtttctga ttttggtagc    2220
cgagtgggca cagtttattg agaatcattt ttactgccat ttgttttctc acaagaatgt    2280
```

```
gcccaaataa tggttttttt ctcatttgga tggcagtgtg aattgtacat catgttttca    2340
gcatctttct caacctagtg ttccccagtc aagtttgaaa tctgtgttat ccaaatgaat    2400
tgttttcatt ttccttttct tagacaaagt gggactccag gtttcatttt gcttttaaac    2460
attttggttt tttgtttgcc tgttttgggg gcagttattt ctttcatatt aaaaagtact    2520
gtgcaggctg ggtgcagtgg ctcattcctg taatcccagc acttagggaa gcagaggcag    2580
gaggatcgct tgagtccagg agttcaagaa gtgcctgggc aacatagcga accccattc     2640 tctatttaaa acataaatgt aaccccgtt ccacgcacaa agtactgtgc aaattaatta     2700
aacatgacca cccagaccag caactgtcca agagtggccc atagaccatc tgtggtagga    2760
taatttgaaa tgcttgttaa aatgcagatt tgtagaccca gggatattct gacagagtct    2820
aaagtcttaa gaacaaaact gttctaaaca taagtcagta ccaatgccag ttaatttctg    2880
agatatattg ataaacttta gtttccagtt ttttaaaaac catattattg acttaaaaac    2940
catgatattg accagttatg tcagtaactt attttgcaca tctgtgtggt gtgtgagaac    3000
atgtgcagtc acttattcat tttgcctgca tttgttcata ttgggatcct cagattcaat    3060
gcactggatg tttgcactgg gtatttactt atactctctc tatttattcc gtctcatact    3120
tcgtcctatt tgttcatact ctcttatttg cccagcaagg tcaatgccag tttaggccta    3180
gggagtcatt ttttcttagt tgatatgact tagaaagctt gggagcctgc ccaacatcaa    3240
ttactttttt aaagctggta ttttctaggt cttgatattt attaagaccc tagcatagtg    3300
gacaattttt ctttctctca tgctttttca cacctcata gctcttcaca tttagttgac     3360
agagaattca gttatcttgc tgtagagtga cccatggtga ggaatctatg ccatggtact    3420
tttctggttc ttatccctta taggtaaaga caagtttctt atgtctgaag cttgatgtca    3480
ggatgagttc agggctttga tgaataagtt cagatctccc aattgtaatt cattagcatt    3540
gcacttaaaa aaatttatat acgttttaa aaaagggtaa tgctaatgaa ttacaataga     3600
gagaaaagta cattagtttg catgtatgtg tgaaactggg aaaattttc acgaaaatat     3660 tcatatactt tttaaaaaaa gggtaatgct aatgaattac agtagacaga aaagtatatt    3720
aatttgcaca tatgtgtaaa attgggaaaa ttccacacat acataaaagt atattaatat    3780
gcatgtatgt gtggaattgg ggaatgtttt ctcttcctca gtttctctcc cttgctttta    3840
atgtacagtc tttatgagcc attatttcag ctgtggcagt ttggttacca ggggaagcgc    3900
actagaaaat tgataaagga aaatgagaca aggtcataga ttctctcact cccttcaggg    3960
tacgtagatg aactatataa aaatccgtct aagtgggatt cgttaatcag caatttagtc    4020
aaatgtgtac atcctatgtt ctataagaaa tgtcagtggg tcctttccca agggagtgag    4080
atcatcagat gaaggttcat ttggtttcaa tgtcccgtat cctttgtaa gaccttgaag     4140 ttggcaatgc aggaaaacag gaactccacc ctagctccat gaattgcaga actgttgtgt    4200
tggtttatga ccatctgccc attcttcctg ttatgacaca gcttgtgaac ttttactgag    4260
aatggtgaaa agtaaattcc cagttttata caatgaattg ctgaagaggc cttttaaagt    4320
atagagtatg cattgtttat ggaaggtgtt tcctattagg tctaactcag tggcaactac    4380
attcatttat ttaatttgtt tctaggtttg cctagtgttt tcttgatct gcccaggctc     4440 agcatacaaa aagacatact tacaattaag gctaatacaa ctcttcaaat tacttgcagg    4500
taaggattca ttctagatct agatttcttg tgttaagtaa ctgattgttt attgagtgga    4560
aataatttcc agtagagcag aattataata gagcttgtag taattgttca taagtggtga    4620
ggtttctaag aactgatgta ataatggaaa atgagaagaa ttttctctca aaaattctgt    4680
```

```
acaattttgc tggtgttttt atactattct ctgccaacat gcatacacac acacacacac    4740
acacgcacac aaatacacac ccacacccac attccaataa ccagtacagc cacctggcgt    4800
atagtagaca tacgctcaat aaatatgaat gaataaatga agttgagggc atacatttaa    4860
ggaatagagt tgaaaaaatt tgggactata tttattatgc ttggtatgat tcttgaacac    4920
ttattatccc tttccaaaaa ctttgcttta taagaaattt attactataa ttacttaggc    4980
agtaatattt aatagcaatt taatatttag tgggtaatat tactgagcgc atgatctaca    5040
taaataatgg acttcgggcc ctgccttgat attctggaat gcatctttcc ccacttgcta    5100
gcaagaagtc atgctattga tttttgataa ctggagaagt agacttcttt gtcaagaaga    5160
agaggccttt aaattttgcc tttcaaccct taccccagga cgaaagatag aagacccttg    5220
ggtttaacat agtgatcaca cacgaaaggc atggagcctt cttaggacct gtgtgttttt    5280
ggtagagact gtgacaagtg gaggtgatgt taccctcctg gaagagtgct gggggtccac    5340
aaaggacctt gggtaggtta ttgccattgc ttcatacttg ttgaatacta agcattaaac    5400
cgaatgacat acatctattt tagactgcag tataaagaat accctagccc cttaccaata    5460
cccagccctt gggaaaaaac acagtagcag gtgctgtttc tctagcttta cttgtttaag    5520
acacatttcc cattagattt tccttttacc gaccctcgat aacaaggtta tttgaaatcc    5580
ccaaggatcc catgctccct ttttaaaact ctgcataaac atttcttatg ttctgaaaaa    5640
aaccatggag tgtgttaaaa gtaacttcat tgatttagct gcaacttcct ggaaatttta    5700
agttctttga atgaagggcc aataatgtta cattcttctt gatgttgact atcttcttat    5760
cttccttggg gccttgtaga gaaatgctgc agtacaagcc atctatgttt taatgcgagg    5820
tccttacaag gtcctgaggg actcttactt gcacctcctt ccttcctaac ctcacttctt    5880 actcccettt gctcactctt acctggctgc tctggtttcc tggctgttcc cttaatactc    5940
cagatatgca cctgctccag ggcctttcca tgtgctgttt ttgctcctgt aatactgctc    6000
ttcatgatgt tcctatggct agcttatca agaccacctc ctgcaaaatt ctttactctt    6060
ttctttgtat cttctatatt tttctccata gtactaaaca ctatctttta tacaataaac    6120
tttccttact ttttaattgc ctgttttctc cagttagact gaggttccat aaaggcattg    6180
atttttgtct gatttgttca ctgctctttc tctagtcctt aacaagtttg gcacatagta    6240
gatgcttaat agatatttgt tgaaagaaag aatgcattaa ttaatggaaa actcaggaat    6300
ctttataagt gacttctgaa gctgagttta taacttttca tcatatgtca atctgacttg    6360
ttggtagaag acttttgtttt ttttttttg aggcagggtt gccctcttgc ccaggctgaa    6420
gtgcagtggt gtgatttggg ctcactgcaa cctccacctc ccgggttcaa gcaattctca    6480
tgcctcagcc tcctgagtag ctgggattac aggcatgcgc caccacacct ggctcatttt    6540 tgtatttta gtagagacag ggttttacca tgttgcccag cctggtctcg aactcctggc    6600
ctcaggtgat ccatccgcct tggcctccca aagtgctggg attataggca tgagccacca    6660
tgcctggccg gtagaagact gactgtgtct gttgaagagt ttatttaagt ttcaaaacca    6720
aattttctct tttcttagaa atagcctcac agtctggcac ttcatattaa tacctccctg    6780
aaattaattt ttcaggggac agagggactt ggactggctt tggcccaata atcagagtgg    6840
cagtgagcaa agggtggagg tgactgagtg cagcgatggc ctcttctgta agacactcac    6900
aattccaaaa gtgatcggaa atgacactgg agcctacaag tgcttctacc gggaaactga    6960
cttggcctcg gtcatttatg tctatgttca aggtaagtgg tgaaataaaa ttcatttccc    7020
```

```
acgtctcttt accagttata aaagacaata ggctcaaaga agaattgagt acaacaaagg    7080
gcttgctcta aaggctgttt gccaagagga atacacacaa ttcttctctc ctgaggcttt    7140
ctctgagaaa taagactcat tgattctgga gcttgggccg tgttacctct tttttgccca    7200
gttagtttgg gtctgatctt tgtttccaag gtaaatctgt gttcactgtt ggccattgag    7260
acttataaaa agtcttccta tgtttgagaa gaaaacctaa aattcttgaa atcgaggaag    7320 atttggggt gaattatgga gaaatttctg tggagagata agttatctac agcagagtag    7380
gagattttcc caagaatgca taggaaagca ttttttgcca agggctctgg agttttttgc    7440
acataggaac cttttttttct tactagtatt tcataaaaaa caattcccat actcatgtgc    7500
aaataaagac attgcttcag actcttttca ggacaatgtt tctttccttt gcttgtttgg    7560
tctgagatct tggatgatat gctgtatctt tctaggatgt gcagtttggg attgatatta    7620
tgaaggctga cttaacatcc atagtata aaataaatgt cacacatatt ctgcatttat    7680
aatgagttat gcattctttt gtgtttcaaa aatcttacac tatcttatct tttctgtgaa    7740
aacctaactt aactaatgag atccctatga tataaattta aggaatgtaa gggctgcatc    7800 atagttggt tggatgtacc aaatatttt cttttcagtg aagataaaca gacattttat    7860
gtatttacgt atatgccttt ttacatccca gagtatttga gacaggtgaa gatgacttag    7920 actttttcc cagaagcagc ttttacaggg caagaatttc atcagctttg ggaaacacac    7980
ttgcatatct ctgcttacat ttcagtagtg taatatggtc agtgcaatga aaaagtggag    8040
accacatcaa aataacctat gccactggat tcacaatgtt tgagaaatat cttgcccag    8100 agtaagcact gtcaaagata gaattctgtg ccctcctcct tccctccaca agatttgaaa    8160
gagacaaggc tcacatcttg gagaatttct ggctccttt gacctggcag tcttgagaga    8220
tgcagctcgg tcagaagatt gcaaggattt cctgctttca gcctgtctag aaatactaca    8280
agatgaacat ccccccatatc tcattattta cttcttccta agtcaggaaa cttggagaca    8340
tgtgaaaatt catttcatga gtttcagtaa atatttatt ttgagaggct gggtggtggt    8400
ttgggtttct tttgtttatt tccttttttt gagataccga aatagaattg atttactaaa    8460
taggtttagt cttacgtcaa agggttaatt tagcttccaa aggcttgctc tgtaagcaag    8520
ttatgtaata tttcataaca tgtggatgaa aggtaggcaa tattaagaag tggcaatccc    8580
tagcactgtt tattggtaca ctgcctgtct ttgggtatac cattaaattc tgcttcctgt    8640
ctaagcttaa agttctagga gttgggctgt ccaagatttt ggccatgaag ttaaacaatg    8700
ggaaaggaaa cactgaagta ttctctatgg ataggtgttt aatgtcccct ctggtcgcca    8760
ccttacttcc ctagtcttct gacccccattc tcttcagcaa tggatggagc caggaagtga    8820
gccctggcct cataagataa tggctatggc atgtggtggg ctagattggc tgcttttctg    8880
tgctttccag ctgggaagga aatcaaactt ctgctgttgc agggaattag ctgcctttgt    8940
cccctgtggt ttaattaact cttttcttcac tttgactgac tattatgaag cactctgaga    9000
atgcttgatg ggatgtgttg ggcatagcaa tgtgaaatgt tatctctctg agatttcaag    9060
catgactcca caccacatca tctctatctc tgaggaatgg actaggtttc cagcagcatg    9120
ttaacattgt atgagtaatg tttgattggc cttgaaatct tttttttttt tttttttga    9180 gacggagttt tgctcttgtt gcccaggcta agtgcagtg gtgctatctc agctcactgc    9240
aacttctgcc cccggttca aatgattctc ctgcctcagc ctctgaaata gctgggacta    9300
caggtgcgtc ccatcatgcc tggctaattt tttgtatttt tcgtagagat ggggttttgc    9360
cacgttggtc aggctggtct caaactcctg acctcaagtg atccacctgc ctcagcctcc    9420
```

```
caaagtgctg ggattacagg cgtgagccaa gaacccagtc agaatctctt cagttttctt    9480
ctcagtcttt ggagtggtga cttttcaaat gtttgtcatt gaagatatca atgactgcta    9540
aatgttaaac taaatgcaaa aacaattaaa catggtttta gaaagaatca tatccctagt    9600
cttcagaatc ttaaaatgct cacatgaatg gtcctcttga ataaccaaat tcaaaagtgt    9660
tagctgtttc ctgttaatct aaagatcctt tgggatccat tcatttattt tcatggaatt    9720
tacattattt acctaaagag agagcacatg agtattttaa atattagtaa aacttgtcgg    9780
taaagtgtat agatttaact ttaaatttta aagtaaatat tatccttcat tttgaaaaaa    9840
ttataatgat taatctttta aaatgtgaaa tctataaaaa tatattctgc ttgtcaataa    9900
accttgtgaa aggagtcaat ctcaattggg agttttttt caaaatttt atacacacag      9960 atatatacac atgcatgtgc atgcacaaac acacacacac acatacacac acccctcat    10020 gtagcacaga tatctatcag cagaataatc tgtggatgcc tttggttgtg tgaggtgtcc   10080
cttccagtca ttcacttgtc tggttagagt ttaggaacct gaaaaatgac caacttttct   10140
agtaaatact attaactcat taataaaact aaattttctt ctagattaca gatctccatt   10200
tattgcttct gttagtgacc aacatggagt cgtgtacatt actgagaaca aaacaaaac    10260 tgtggtgatt ccatgtctcg ggtccatttc aaatctcaac gtgtcacttt gtgcagtaag   10320
ttgcatctcc tccaatcgtc tcttaagttt ttataatttt aagctaatat taagatgggt   10380
aacctgttta taatattcac aatgagtttt aaggatcctt taggaagggt caaatgcaat   10440
gaataaaact aattagtatt cttaaaaata agatgaattc ttcagtgatc attgtacatg   10500
gctctcattt ttggtactgg attaaatatt tgatatgtct ttttattacc cagagatacc   10560
cagaaaagag atttgttcct gatggtaaca gaatttcctg ggacagcaag aagggcttta   10620
ctattcccag ctacatgatc agctatgctg gcatggtctt ctgtgaagca aaaattaatg   10680
atgaaagtta ccagtctatt atgtacatag ttgtcgttgt aggtaagagg catttccttt   10740
tccatatcat taataacata tccttgtatt aagatcttgg agataacaac atagagtgaa   10800
gaaggatatt gaaagtata ggaactcagg atatggtgtt gggcaattca tctgctcttc    10860
tctaccaaat aaacccatgt gcaattgagg ttgtctcttt tcttgccaag attaaggaag   10920
aaaaagaaaa cttttaaaa aaaggatgaa agcgaatggt attactcgag cacattttat    10980
gaagaattca atgttcagag cattgcttgc tatcaattat ttcaattatg actattttat   11040
ggaaacttca gcaatttgct aaagctggcc ctactggcct agggctactg accactgaaa   11100
gtttactact tttctgtcca ctgggttaca acatctttga gatctgtgaa ggtagtgctt   11160
tgtaaacctc tgttggccat tttcctggga gctaccaagt attggtgagg cctgcaggga   11220
aaaacaatgt ggcatgtttt aaagttgcat tactttaaaa aataaatctg tgcaaagtta   11280
taggcttatt tgctctctca tgttctgttt tttcaattta cttgctctag ggtataggat   11340
ttatgatgtg gttctgagtc cgtctcatgg aattgaacta tctgttggag aaaagcttgt   11400
cttaaattgt acagcaagaa ctgaactaaa tgtggggatt gacttcaact gggaataccc   11460
ttcttcgaag gtaacgctaa tgattcaaag ccagacctcc aaatacttag ataataagcc   11520
ccagtgaagt ttgcttgaga gatagggggcc tctttggcca gataaaatgt aagagcctta   11580
aacacacaca catacacacc cactcacaca cacatacaca cacacacaat ttaagggaat   11640
tgcagaacag atagcaccca ccaaaaggtg aaataccagg aattttgtcc tattctgcaa   11700
tagccaggct atgaatatta gttttctcta ggtgattaca tctttccaca ttatgtcatt   11760
```

```
tctctgttct ccaaagtttt tgatctacat tccttttaag ggaatttctc tttaagaggt    11820
ggcatgagat acactgctcc ttaaacagtg gtcacattta cttgtgtttc tgcagtttat    11880
atccatctca ctttcaccac gtgaggtttt aaaaatccta attcagttgg ttccatttat    11940
ttctcctgaa acaaaatata tttgttgtct gcatgaggtt aaaagttctg gtgtccctgt    12000
ttttagcatt aaataatgtt taccaaagcc cagatttaat tctgtgtgtt actagaagtt    12060
attgggtaat gttatatgct gtgctttgga agttcagtca actctttttt tcagcatcag    12120
cataagaaac ttgtaaaccg agacctaaaa acccagtctg ggagtgagat gaagaaattt    12180
ttgagcacct taactataga tggtgtaacc cggagtgacc aaggattgta cacctgtgca    12240
gcatccagtg ggctgatgac caagaagaac agcacatttg tcagggtcca tggtaagcta    12300
tggtcttgga aattattctg tgccttgaca agtgagataa tttaaataaa tttaggtcac    12360
ttagtgattc ctatttttgtt cattcagaag atagtttcta gttttcttg ttagggaggc    12420
cacatgacct agaggtcaag agcatagctt tgtagtcagg aacttgggtt caaacctcaa    12480
ctttaaagat gagatgtgct gatatacagt aagagttcat ttagtattac ttattatagt    12540
tattgctgct attaggattg ttactatgat aaatagtatt agctaaggta gttttttaaat    12600
tttcatttta ttgcaaggct gagaggccta cttgaataag catgagcttt gcaaactggg    12660
gaaacattta gcaatataca gttgacctgt gagcaactca gggattgggg gaactcaggg    12720
gagttccccct aactttccct cctctgcagt caaaaatcca tgtataggcc gggcgcggtg    12780
gctcacgcct gtaatcccaa cactttggga gtctgaggtg ggtggatcac ctgagatcag    12840
gagttcgaaa ccagcctggt caacatgtg gaacccatc tctactaaaa atccaaaaaa    12900
ttagccgtgg gtggtggtgg agcttgtaa tcccagctac tcaggaggct gaggcaggag    12960
aattgcttga acccaggagg tggaggttgc agtgagccaa gatcgtgcca ttgtaccca    13020
gcctgggcaa caagagtgaa actccttctc aaaaaaaaaa aaaaaaaaa aatcaaggta    13080
taactttga cttccacaaa acataactaa tggcctactg ttgactggaa gccctactga    13140
taacataaac agtcaattaa cacatatttt atatgttata tgtattatat actgtattct    13200
tccaataaag ctagagaaaa gaaaatgtta ttaagaaaat tgtaaggaag agaaaatata    13260
tttactattc attaagtgta agtggatcat cataaaggtc ttcatccttg tcttcacgtt    13320
gagtaggctg aggaaaaggg ggaagaggag ggggtggttt tgctgtctca ggggtggcag    13380
aggtggaaga aaatctgctt ataagtggac tcatgtagtt caagtttgtg ttatttaagg    13440
gtcaactgta attgaactgg aattaaattg aactggcctt gagaaaatca ccttaatttt    13500
ttgtttattc tctttcattt acataaatgt ctgagtttac atggtaattt gtgtggcatc    13560
ctacttataa gccttggaaa ggattttgga gtttatatta tgagaatgca tcaatacagt    13620
gaaatttttaa aaatacctta gataatgcta tttattagag ttgtaatcat aaaagtggca    13680
acaactataa caagtatgat ttagtgagca cttactttat tagctcatct catctttgaa    13740
gctgagattg gaactcaagt tcctgactac aaagctatgc tcttgacctc taggtcacgt    13800
ggcatcccta gcaagaactt gaaaatttct tctgaatgaa caaaatagaa atcactaagt    13860
gtcctaaatt tatttaaatt atttcacttg ccaagatgca cttgtcaaaa tacacagaga    13920
gagatgtgct ctggcttatg ttttttataga attacttttg ttttccagaa tacttcaggg    13980
aaatagggcc agaaataagg aggtcagttg ggaggctaat tgcagttatc caagtgagag    14040
ttgaggggtg gcttagacaa gggtagttga ggtgggaggta gtgagaggtg atctgcttct    14100
ggatatattt tgaaggtaga gtcaacaggg tccgctgatc aattcattgg ttgtggagta    14160
```

```
taagagaaaa agagtggaag atgactcgag cgttagcatg agcaactgag taaatgatgg    14220
tgttatttac tgagatggca agatcgaga aggcagtgag atttagggaa acagtgttag    14280
atatgtttat ctggagatgc ctgttaaaca tccaagtgga gatatttaac atatcaaccc    14340
ggaacccaga ggagtcaggg cagaagataa cacatttagg aggtacgtga atgatacttt    14400
aaacctgagg ctagaggaag gtgtaaataa agaggaggtc tgaggactga gtcctggggc    14460
ctcatggtgg aagaggtgtg tggaggctgt catgggagca gaggagaagg agcacccaag    14520
catccctggg ggacttagag aaagctgcac agaggagcaa gtgtttgagt tgagacttga    14580
gcaatcacta ggcttgtggg agtgcactag cggggagaga aaagcaaatg caaacacagg    14640
aggtgtggga gaaacacggg aggtgtggga gaagctgaaa agtgacccac tgaaagatag    14700
tacaggaaat cttggaactg cagctactca gaccctcaag gtctttgacg tttcacttga    14760
aatgaaaaac taaatcaaat gaccatttac agtaagttga cctttttttt tttttatttt    14820
cttccagaaa aacctttgt tgcttttgga agtggcatgg aatctctggt ggaagccacg    14880
gtgggggagc gtgtcagaat ccctgcgaag taccttggtt acccaccccc agaaataaaa    14940
tggtaactac tggaaataaa tgcaaagcat catttcgtgt gagagcaaat cctttgacta    15000
tactaattcc tgagaatttt ttttcatagg tataaaaatg gatacccct tgagtccaat    15060 cacacaatta aagcgggca tgtactgacg attatgaaag tgagtgaaag agacacagga    15120
aattacactg tcatccttac caatcccatt tcaaaggaga agcagagcca tgtggtctct    15180
ctggttgtgt atggtgagtc cattcaattt tcctctctgc ccaagattta ttatgataca    15240
ttgtcttcca aatcagccaa accaccgttc ctctgcctcc tgctgcttca ctcatatcat    15300
ggctgggcct gcgtacaaaa gtcatctggc gtggtgaagc tgaagtgaaa cgtaggacca    15360
tgtgctctgg ccatgtttgt ttaagaggcc gtgtaaatga gctttgtggt ggacaaatgc    15420
aagattaaag tagtgatacc ctcgatagct aaatgttgtg aaataagaat gcccacaggg    15480
acagttgtca agctaagtta tactaccatg ttcccctctc atggaattgc ccacctggta    15540
cacagatgtg taagacccct ctccttagat tttgtgcaaa gcttctagtt tgatgttgta    15600
gttgatgtat cagagatgtg caggcacgtt ccaactctga aggcttttga agttgacact    15660
gttggcttgg ttgggagctt ttctttttc cttttgaca ggagttcagg atctgatttt    15720
gagtctgtaa aggaaagata gtaagttttt gatgtaaaga taatttgaac tttgttttct    15780
gaaactgaaa ggtacaaata agtgtttgga atggagtggg gagaagggtg ccatggtcaa    15840
gtgagtgtga gaggtgctaa ggtgatgtgt agatgtgtaa caggtttctt tattgcagga    15900
cttcgcagaa ccttttatat gctaatgtat attggtattc tccaggagga gagacataga    15960
gtattcaagg tttaacaaac ctatttgacc agagcacctt ttttcccctg agcaaattca    16020
ttaatctctc actccaaaca gtttgagaaa tgcttctctg ttgtaattct ttgttccccc    16080
ttctggtacg gcatattaaa acttcaggat attttcccat gacattaagg tgcttcccta    16140
cgtgtcctga tactcttctg taggccgctg aacttggctt tattattttt tttcagggaa    16200
tattttaaag ataggctggg tgccgtggtt tgcatctgta atcccagcac tttgggaggc    16260
cgaggcggat ggatcacctg aggtcaggag ttcgagacca gcctggccaa catgatgaaa    16320
acccgtctct actaaaaata taaaaattag ccaggcatgg tggtgggcac ctgtaatccc    16380
agctacttgg gaggctgagg caggagaatc acttgaaccc aggaggtgga ggttgcagat    16440
agccgagatc gcaccattgt actccagcct ggtgacaaga gcaaaactcc gtctcaaaaa    16500
```

```
aaaagttaac aggttccaaa aaggttgttt agaagcagca taggtgtagg ggactgggga      16560
gaggagaaac tggaaagtgt ataagtagga tgggaggagg aaatgaacag gaaataaaaa      16620
caaaacacgg acagcaaata gcccatttca tcagttcatg aagccactaa atattttatt      16680
cactttagca aattctctgc tatatgaaat aaacataaaa aagaagtcaa gtcttcaaag      16740
cataatctga ggctttaggt tgacagtaat aaggaaatag ttttgacttt ggagtcaaaa      16800
aagaaagaaa ggaaaaaggg agagaagaaa gaaggaagtg agagaaggga gaaggaagaa      16860
aggggaagag ggaaagggag tggagaggga gggagggagg aagagggaga gagaatgaaa      16920
aactcagatg atggtggcag gaatgcattc tctaaagatt tacaccttcc tttaacatga      16980
ggtggtttac gtgtttgggt tcagaagtca gagtgtctag gtttgttcca ggttttgccg      17040
ttcgttaact gagtgacctt gggcgagtca ttttttctg tttcatttt ttctcacgta       17100 taaagctgtg gacagtaata gtggttgtga ggattaagtg aatgaattca tgcaaagcac      17160
ttcaaacaat gcttggcaca taataaatgt atttactgtg ctatttcagc tgttttctgt      17220
agcctttccc tgatctccta aacttgagag gacagagaga actatctctg taatacagat      17280
gagaggcaca ggatttcaac acttccataa agtcattcag cttgttagtt tattattat      17340 attagcttat tgtcattttt attttatttc gttactttat tccttttttt ttttttggt      17400 agagatgggg tctcaccatg tggcccaggc tggtcttgat ctcctgggct taagcgatcc      17460
acctaccttg gcgtcccaaa atactgagat tacaggcata agcccccatg cctggctagt      17520 tgttatttt atgagtatca ctagaactca ggtctcttgt ttccacatct aggtgttctt      17580 cgaaaagaa agtggaagca aaatcatatg cttaaagaaa gtcagcttta gttgctaaaa      17640
tcctctattt cccattcttc aaagctgact gacaattcaa aagttgtttt tcccatcttc      17700
agtcccaccc cagattggtg agaaatctct aatctctcct gtggattcct accagtacgg      17760
caccactcaa acgctgacat gtacggtcta tgccattcct cccccgcatc acatccactg      17820
gtattggcag ttggaggaag agtgcgccaa cgagcccagg tgagtaaggc cacatgctct      17880
ttgctttcct gccatcttgc atttcttaca gctgagctat gatatgactc catcctaaat      17940
ggagaagcct aaaccaaaaa aagttttctc tcaagaggta gcctgaatct ccatccatct      18000
ttctctgtgt cttacatttt aggggatgtc tttgcttgga gtatcctcct ttggggttag      18060
ctaagctcag ccttgttagg ttagccgtga ggtacacttc tccaaacaca ggctatttgc      18120
tcagtttgct aattgccagt cttggtttt tctcccgata ccaatcggct ggtgaatacc       18180
acatccctcc ttcttgtgtg tgtgaagatc catctctcag aggaaatgct gatagatgag      18240
aggcagtgat agacccagcc ccagtcctca gggtctcagg cccagcttat catgctctga      18300
cacaagtcca gacatcctta gggaaaaaca caacaacagc agccaaccca ccaccaccct      18360
aagcagtcca cttcctgttg ttgttttga aatggccact atgagcttct tcctcagctg      18420
ctgatcattt ccttcacaga gaccatggtc ccagagaaat tactttaagg agcccagtgg      18480
cttctaagtt tccttgcctt cctttgaact aaattaactt gaattgtctt gtcgatccaa      18540
tttatgaatg aaggtttatt cccagaatag ctgcttccct cctgtatcct gaatgaatct      18600
acctagaacc ttttccttca ttgtcaatgc ctatttttaa ttggcgccaa gtcttgtacc      18660
atggtaggct gcgttggaag ttatttctaa gaacagaata accaaagtct gaatcttttc      18720
cttactcttg actctaatta aagaaaaatt aaatcataat atgcgctgtt atctctttct      18780
tatagccaag ctgtctcagt gacaaaccca taccccttgtg aagaatggag aagtgtggag      18840
gacttccagg gaggaaataa aattgaagtt aataaaaatc aatttgctct aattgaagga      18900
```

```
aaaaacaaag tgagtttgaa gttttaaaat ttgaaaatct ctctctcttt aatggaagga   18960
tggtacaata atatgtgagg catattggag attaataatc aaatagtctg gatgattaaa   19020
tagagcgtat taagtcactt tgaaaatacc attgactttt agcagtacca ttaacttatt   19080
aatagcttat cagagaaaaa taaaaacatc tatgacatta aatctatgca tctgtgtagg   19140
gtgattctga ttttataaac atgagaatga aaaaatgtgt atcatatcat attaaaacac   19200
atcattagtt tcatggcttc caaagccctt tttatataat gtgtgagctc cacagcagca   19260
taattataca aattgagtaa atatcccaaa cctaaaaacc ccaaatccaa aatgctccag   19320
attctgaacc tttttgagtg ccgacatggt gctcaaagga aacgctcgtt ggagcatttt   19380
ggattttcag attagggatg ctcaactggt aagtatacaa tgcaaatatt ccaaaatcca   19440
aaaaaaaaaa tccaaaatcc aaaccacttt tggtcccaag cgttttgagt aagggatact   19500
caacctgcaa ttgcataaat ttgagcgtgt ccaaccgctg cagaagtggg aatggcatag   19560
gcaggttgga gtgattgtgg agactgctgg actgagtgct tgtgcacaaa cagccgcgtt   19620
gtttatggcc tgggatttgt tttttccccg cacagactgt aagtacccct gttatccaag   19680
cggcaaatgt gtcagctttg tacaaatgtg aagcggtcaa caaagtcggg agaggagaga   19740
gggtgatctc cttccacgtg accagtaagt actcttctct ggaggtttgg gttggatcac   19800
tcacacagtg ggtactaagc tatgtaattc cctgttgttt ttgccattca tgtgagtggc   19860
atggcattta ggaaagagga cttggattga tcattgatgc tttcattcat aaattacaac   19920
ttctcaggta tctcctgggc ttatgtgaag tcagtgcgtc taactacact ggagagagaa   19980
tggtttcaca gatgctttaa accacaagct ctgtgtggta tttacatctc agtcttcaga   20040
gtctggcaca gtgcctggct tattgagctt cagtacatat tggtgggctt gctgtggaac   20100
agttgatgag ggtgggcttt atggaggcaa tcagaaggac ataggagcag tgccctccca   20160
atgctgccga ttttgcctgt gcatcttagt tttatggata agctttagct gattgtgctg   20220
aatggaatat tatagccagg gctaattcat tggcataaat gtagctttca tatcattgag   20280
tgttagtgtt aatgaagacc taattttaaa attctgttag aattagagat tttgctttgg   20340 attttttaata tattaaacat tgcgtagagc tcatagtgga gatgtggtaa atatctgagg   20400
aattcgttta cattttcaag taatgtgttt ggccaaataa gatattttgg gacctgaatt   20460
gtctagtttg tttgtcaagt tgtagtacat cacctgaaac ggatagagct tcatttcttt   20520
tggtactttg tagtagtctg aaagcagcaa gatgatagtg agctgtacca agttaaatca   20580
ccattcaata actatggcct cttcatttta gggggtcctg aaattacttt gcaacctgac   20640
atgcagccca ctgagcagga gagcgtgtct tgtggtgca ctgcagacag atctacgttt   20700
gagaacctca catggtacaa gcttggccca cagcctctgc caatccatgt gggagagttg   20760
cccacacctg tttgcaagaa cttggatact cttttggaaat tgaatgccac catgttctct   20820
aatagcacaa atgacatttt gatcatggag cttaagaatg catccttgca ggaccaagga   20880
gactatgtct gccttgctca agacaggaag accaagaaaa gacattgcgt ggtcaggcag   20940
ctcacagtcc taggtaggga gacaattctg gatcattgtg cagaggcagt tggaatgcct   21000
taaatgtagt gcaattcagg tgctatgcaa agattactgt cctctaggag attatgttgt   21060
aaactggtgc acacttcttc accgaaagtc cttgaggaag aaagaagcta ataataatga   21120
aatgatatat cgaaaggaga aaataacaaa acctgatgat ggagtaattc actagtatat   21180
gcaagggata ttagcttgaa ccagggaaac ttctgcctta tcttgggcat ccatttattt   21240
```

```
aaatagacaa atatttgtgg aatgcctgct atgagctagg agagtgtcag aaattcacag    21300
tggtaaacat gaaggaaagg aggagaacat aggcaaccac tgggaagtca cagcacagtg    21360
aggtctctgt gtccatgaga acaggaattg ttctctgttt tgctccctgc tatagctcta    21420
gtcatagagc atagcagcat atactaactg ctcaataagg cacctgctgc atgaagagtg    21480
ggatgatggg ctgcgtttaa gacctagaag actccatggg aaggaagcta cattcactgt    21540
ctgtacctct gggtcatccc acatgatcca gcgtagccca aggtcaatgg gacgatcact    21600
tcagtgagca gatagctctg taaattcctc catagaggca ctgtctaccc cttgtctaac    21660
ctcatgcctt gtgcaaaagc tgggcagcca tggctttgtc tgtgggaaaa tcaggcaaat    21720
ttggggagcg tctctttgtg ccacttctct ccattttctc ctcttgtggt gtccctttcc    21780
aattcctagg atatatgtgc cctctgtttt tttttactg ttaggaagga aattgcccaa    21840
gtaaattcat ctataccaca gttttagagg gtaacgtctt catcagaggc cttggcgtat    21900
ttgaagaggc accttctgac agacactagc ataaagttcg ctagttttaa gactcaggtg    21960
tcataataag agatactttg gggtcaagtc atccccagca tccttcaagt cacaccacat    22020
agatcacatg gattttctgt tggcttgtct ggcttcaagg ttatggcaga attgagaaag    22080
agatgtgaag taggctcctg gcctagctgt gcccagaaaa tatgtgctcg cagttagctg    22140
ctttgcttcc ctaaggactc ctaacttgtt ttcctaaaac ctattcttag aaataggcta    22200
gaatccagta catttgctta gacttcaatg tagtacgctg ttgaggtaat ctcattttgc    22260
taagtgttga cgtggatttt ttcagcatga ttccttttga tgttcagttg gttgggacaa    22320
gatatttcca cagcactttg atgatctgaa gaaagaataa atctaaagtg ttcttgtaca    22380
cttaaacaaa tactcatggg cttcattttc tttaaatcca agacttccct tagggtattg    22440
ttgttttgtt tgtgttttag tggaaatagc actgaactgg tcttttagcc tcaccagatt    22500
ctgtaaacag ttcaactgtt tacttagttg cagggacatg gacaagtggt ttaatgtcgc    22560
tgaacatcat ttatttcatc tgtgagataa cgctaacagt cctattctgc tcattacata    22620
agatcactag tgaggaacac aaattgtgta aacaagtttt ataagaattg ccaaataaat    22680
gtaaggcatt attggttgaa tgatactaaa atttggcact tccaagagaa atttgaaggg    22740
attctagggt attattgact agaatcttca tgggagggaa gttttcacct ggggaggctg    22800
tgtctaatta gaggaaaaat ccataaaggt gaccctgaac cttctttttg tgatgggatt    22860
accagctagt atcactaata tgaatgttaa aagccattaa tctgtttgca gtgtcctgac    22920
tgacttgttt catttaactt tacccagtga ccagtgtatt ttcccagaag ttaatatatc    22980
aacaagttcc tttttactaa atttaaactg tttaaaagtt tgctgatacc agaaccattt    23040
caaaagttat aattccatgt tctgtgattt tcttttgtg tgtctagagc gtgtggcacc    23100
cacgatcaca ggaaacctgg agaatcagac gacaagtatt ggggaaagca tcgaagtctc    23160
atgcacggca tctgggaatc cccctccaca gatcatgtgg tttaaagata atgagaccct    23220
tgtagaagac tcaggtaaat agaatttggc tatcactctt gggttgcaga actttcccag    23280
ggatgttatc taaaaagcca tattatttct tgatgtaatg tagaaaaaaa gcagtattgg    23340
tgtccatgac ctggctcatt tcacagactt agaattggag tatggggccc tgttgaattt    23400
tcatgaaagc catataggag attagtcagc agtagatccc atgtgactct acagagttag    23460
ataatagaac aagatgaagg gcagcattta tattttctaa atttccctga aaaacttcac    23520
agactacatc atcataaatg agaatgatcg ttttcttcct ctgttaggca ttgtattgaa    23580
ggatgggaac cggaaccctca ctatccgcag agtgaggaag gaggacgaag gcctctacac    23640
```

```
ctgccaggca tgcagtgttc ttggctgtgc aaaagtggag gcattttcca taatagaagg    23700
tcagtgggat aaaaaaaaat gtggtacata tacaccatgg aatgctatgc agccgtaaaa    23760
aggaatctga tcatgtcctt tgcagctgca tggatggagc tggaagccat tatcctcagc    23820
aaactaacac aggaacagaa aaccaaacgc cacacattct cacttataag tgggagctga    23880
acaatgtgaa cacatagaca cagggaaggg aacaacacac actggggcct actgtgggtt    23940
ggggagaagg agagcatcag gaaaaatagc taatgcatgc tgggcttaat acctaggaga    24000
tggattaata ggtgcagcaa atcaccatgg cacatgttta cctgtgtaac aaacctgagc    24060
attctgcaca tgtatcccgg aacttaaaag aaaaaaagaa ggtcagtggg aagtcataga    24120
tacatcctgt ggttttgaa gattagtttg tatcttatag acacacattc actttgaata     24180
gggcaacgac agatgatttt taatattctt tgtactttgt aaatttttctc agtgagtatg    24240 tattcttta accagcaaac ataattaatg ttgttataat tctgcttgca tcacatttcc     24300
tattcctgca gttcttattg tggaaaaatt cttaatcagg caggatgaat agcctcttct    24360
ccctgattct gtctttgttt gaatggcttg attaacttat agaaatgatg cctttatatt    24420
tatttggaaa aacattagaa ttgctgccta atcatggcag tcaatgctat ccagatagtc    24480
acaaggattc cgagttttaa ttggactaga gataattaag attcacttgt gaacaataga    24540
ccattgctct tctgacatgg aaaatttttg gtttttatct caatacgtgt gtatgcagaa    24600
gtgatgtgaa atctgtcatt tccttagcta ggaaaagtaa tttgtggcag aatatttat    24660 cttaagaagt atattcctat ggctttttt tttatagccc accagggaaa gaataaaact    24720
gtgttgtggg gtaaaagaat ggtatgcaag ggtaagaaag aagtatggtg atagaaggga    24780
tcgatggatt tctatgaact catcctaact tgtctctcaa agtctagatt ttggtccctt    24840
tactctgcca aatctatgat gccaagtatt gcatcgagat atgttgacat attttcaaat    24900
gtataagctt attagcattt cataaactac acttgcaaat aaagatttca agaccatgg     24960 cggttttgtc atttccaaag tgattcatgt tttagggcaa atccgcagaa tgacgtctag    25020
attgtctctg atgctctgca ttacctcttg ttggtggcct gcagctggtt acagatgcct    25080
aactaggtaa cactggcaca gagattatag ttacttctta cctggagtga atgctaagaa    25140
aggcagagct agatatttaa tactcctgct gggttcccaa atgttatgcg agaatattaa    25200
tatacaaaca catagaaaac agactctttg aacttttat cctctatgtt caactggact    25260
tttaaatctg tgtgtataaa tagagaatta cttccctagg accaccagag aaacaaaatt    25320
tactccaagc ataattgtgc ttgtctctca atggttaagt taactttat tttgcaaacc    25380 aatttgttac ttattttgca aaccagtttc ttacttgtct tcttctctct tgaggccgta    25440
gtgggccatc cgcacagctt gtgcccggt ttgattctcc ttgcactctt ctgatgggag    25500
gccccaagtg atgactgctt ccttatcatc tctttgctaa tcactcttag tggaaagcct    25560
gtttctgtat tttgtttctt ccactcagag ctgtcctctg aagccctgag catctgcagc    25620
tttgcttgct gacttctagt ttcctcttct cttccttc atgagtgatt tgaaactccc      25680
attaccaggc catgcgtgat gtgctcatct tggctcttcc tcttctcctc actcagactc    25740
ctgccacaag ggatggggta gtgtatgtaa tggttagttc atgttggaca ggcctcttta    25800
tctcttgact gaaccactga ctagctgtgt gccctcagtc aagtagctta agctctctgg    25860
tcttctgttt cttcatctga aaactgagag ttgttgagga gattaagtgg aatggcatat    25920
ttaaagtgat gagtgcatag tagatacatg gtcattagta actctcaggt caaaaaattt    25980
```

```
tgtttatttc cctacttggt ttcttatgtg atccttttgc aaactctgca cagatcaaaa    26040
tattgactat cagtttaaaa gaagactttt gttttcctca aatagaaata ttttttttc     26100 tctgtagaga atgatctgtt ttctttccat caaagactgc tcttcctcta aacactttct    26160
atgtttggct tttaagacat tactacttct atgcttaatt acttaagaat tttattgttg    26220
taagtttaca tgagcaatgt tttgcaagct ttaaattttc cattaacaat tctgtaggcc    26280
aggtgtggtg gcttatgcct gtaatccctg cactttggga ggccaaggca gggggatgg     26340 ctagaggcca ggagttcgag actagcctgg gcaatgtagt gagaccctgt ctctacagaa    26400
aataaaagaa aaattagctg ggcttggtgg tatgcacctg tagtcccagc tactcgggag    26460 gctgagggg gagaatcgct tgagcctagg aattggaggc tgcaataagc tatgattgtg      26520
tcatggtact ccagcctgga acatagaaag aaaccctgtc tctaaaaata aataaataaa    26580
taaataaata aataaataaa taaataaata aattaaattc aaaaaagaa ttctgtagac      26640 tccattcaag ttacgggtgt gtaactgttg tcctctagga ttttccaag ttggtaagct      26700 tgggattttg ctttagtgct aaaatttgtc atcttacaaa caaaaagtat aagtttccaa    26760
ctgttgatac tcattcaatt gtgtctttcc aggtgcccag gaaaagacga acttggaaat    26820
cattattcta gtaggcacgg cggtgattgc catgttcttc tggctacttc ttgtcatcat    26880
cctacggacc gttaagcggg taaaaaata atttcccttc tgcccatgca cattggtttt     26940
catgattaat gaaaactgac tggggttctt tgagttgttt cttcccattg ttattggctc    27000
aatgggcaca ttttatttc aatacaataa cgttcctgcc cactttcttt tggctggatc     27060
tcagggattt aattgataga agccactaga gaggaaaagg gcttggactg tctagtgtaa    27120
ttaagcttta aaaccttaat tctgagctcc tttgggggac aagggaaact agaagcaggg    27180
ttataatagg accactctca aactccatga gttttattgg aaaatgagac aggaatgagg    27240
ctccaataaa cagcaataac aagcacacaa acaacagcc aaacaacagt gtgtttatga     27300
ctggaaggat tgatgctttc caggccaatg gaggggaact gaagacaggc tacttgtcca    27360
tcgtcatgga tccagatgaa ctcccattgg atgaacattg tgaacgactg ccttatgatg    27420
ccagcaaatg ggaattcccc agagaccggc tgaagctagg tgcatttttca attgctatta    27480 atttgatatt gtgtttacca ggccatctct tcctccatta gaatgatgac aaatgtggtg    27540
tattcagatg ttggattctg gtttagaaat attaattcca tttcttgaat tgtataatc     27600 attcatatag ccacttagag gtagggtccc tatgtaatca tccaaagcag gacatttgga    27660
gagtgaaggg ggagttatta aataattaag ccaggacaaa ggagtaaact ggactatcca    27720
tgttaaattg ggatgtatgg tcaccctatc tagttgatgt ctctgcgtat cactttggtt    27780
gtatagtaat ccaagtctgt tttcttgttg ctgttgttgt tgactctagg taagcctctt    27840
ggccgtggtg cctttggcca agtgattgaa gcagatgcct ttggaattga caagacagca    27900
acttgcagga cagtagcagt caaaatgttg aaaggtaaaa gcaaaattat gtggtgatct    27960
atctttctgt tttatctagt ctttaaatat gttgcaaggc ttgtatcagt agctttgtgc    28020
ttatgtgggc ctactagcca cacatgcagt cagcctaaat aatgcccttg tgcaaattgg    28080
aaaaaggatc ctcctttgta gctttatgcc aggatgcatg gtctggcaag caaagttggg    28140
aatggctttc accttcttgc ctggttaccc tcgtgcaggg ctcagccaac acagttgtac    28200
ttagtggttc tgggtacagg gaaaaggac tgtggttata ttaaaattgt ttcttaatat     28260
attgtggaat cagataatta tagaccatct agagacatgg aaaggaagat agtgaaatac    28320
aaaaatagca tgttctccag aattggaata tgtaaaagat gttcatatgt aaaagataat    28380
```

```
ttgcaaaaca agaatggttg tgttagaaaa aaatataatg ggttatattt tttaaattaa  28440
aagctttata aataattgtt aattctaata gtaacggaat tctggtctgg ccattttcat  28500
tttaggaggt tagacagtaa agcttctttc ttcaattgtg atgttctttc attgatgaag  28560
gcagtgccaa tgacccttg ccaataggtt ttgtgcattt caaagctatc tttctccatc  28620 tgccttttt ctcttgtggc caagggagtg tgtaatttg aggtggctca tcagagcctt  28680
agatgtggac catgcctgtg aattagtggg aagtgtagca gtccatacag gatcaaacac  28740
atagtcttag tgccatcagc ctcatgtgcc aactggtctt tccagctggc cttaattcgc  28800
ctgcacagat cggcacagat tggctggaac attcggtata gccctaaca cgtgaagata  28860 tttaatacat ggtgttgctt ccttatgagg aagtgctgaa atgatcagac cctcagaatc  28920
atagtgaacc tgaaatgcaa aaatccagtt ttgcagaaga agagaatctg gcatgattc   28980 cactgcagat gtattctccg ctttgcaaaa ggtttcacaa tgggttcctt taaatatcaa  29040
actttctggc tcacttaaaa tatgaatttt atttcaaatt agaaaataga atttacactt  29100
cacttttgag gaaatgcatg tggtctgtaa actaggtcac agctgtgtta ccccggaggg  29160
taagttgtat agtggcatgc agggagggag ggaccccaat tattgaagga aatgtccata  29220
cctatgattt ccctctttgt actgtatttg tagaaggagc aacacacagt gagcatcgag  29280
ctctcatgtc tgaactcaag atcctcattc atattggtca ccatctcaat gtggtcaacc  29340
ttctaggtgc ctgtaccaag ccaggaggtg agtaactgtg ggtggttttg gtcacccaat  29400
tttaacatgc ctctctgata gtgtttgagg gaaagcagtc aactcctctg gccttgattt  29460
tcttagctta gaatactttg cggattccta ggaataaata tatttcatgg aggtttaatt  29520
ggcactagaa ttaaattatt gtaaaacttt ctctgaatta agaaatgtca tgctactatg  29580 atacagttg ttacttgtgt aacagatgtc cagagaagag taaacttccc taaaacttga  29640
aagcttaagg gtagttaccc ccaaaatgga atcatatcag gagattgcac tgaaaagcaa  29700
gtagatgggt gggttttctt ctgaaatttt ggttaatctt gtgaaatgt gttctggaaa  29760 aaagaaaagc tacaatataa ggggattggg accagctgat ttctacactc ctgtcccaat  29820
gaaaggttgt agccttcttc taaggtgttt ttgggttcat cactatatta aacgcttagt  29880
gaggaatatg agtgaaaacc cattttcctt cctggacatg ctgcctgcag ggccactcat  29940
ggtgattgtg gaattctgca aatttggaaa cctgtccact tacctgagga gcaagagaaa  30000
tgaatttgtc ccctacaagg tatgtcatct cctaatcctg ctctggccat gttataaaat  30060
gaagggaaac tcaaaatggt acaggttagt tttttagttg aaattttgtg aagaacttgt  30120
gaggaatctt ctcatattac ctcttggctg ttgtaacttc ctcttttacc ttctggggc   30180 catatgtttc tgttttatgt atgtgatttt aatctactga cccattacag agtgtggaca  30240
tgggggagaa ggcaggtatg agcgaggaaa ggggagggca gagggtagga catctctggg  30300
ttattctgtc tctcccctag ccatatttgg ccccgtggag tgtaaatccc tctgtgaaga  30360
gcatcctaat gctgaaagtg tgtctgaatg caactcaaaa tgtggcattt gtcactttaa  30420
gctaaagaag gagctaggct ttgtggaaga acccctatta tgcacaaaac ttgccccaag  30480
tttcagctca gagattgcat aatcctgaaa ttgatgtcct ccttgtctgc ttttagtag   30540 tttcaattat ctccatggtt tactacattt taaaggttgt aaacttttaa agactcattt  30600
tgtattcaag gagtttgttt gttcctttgc ttttttatag accaaagggg cacgattccg  30660
tcaagggaaa gactacgttg gagcaatccc tgtggatctg aaacggcgct tggacagcat  30720
```

```
caccagtagc cagagctcag ccagctctgg atttgtggag gagaagtccc tcagtgatgt    30780
agaagaagag gaaggtactg gctagtgctt cctgcatgct atggcatgct cttgtcagag    30840
cagacagggt gatagggtgt tacaaggaat ttgatcatgg gaaaagtcca atactacctc    30900
ataatttgaa agagacctga atttctataa tagactgcct ccattctgtc tccccaaaag    30960
tgaagtgtgg aagccctaga ctgggaagtg aagcagggct agcctgagaa atctgggtag    31020
tccaagtggg ctaagcagtc ggctacaacc acagcagtgt tcttaaaata ctggttcagc    31080
atttattagt gagagaggcc acaagttttc tggtagttga ctagcctctc cattgccttg    31140
gagagcccca gagtggtttg ccccacgttg catgctttac ctgtgcaaaa gtcttttcat    31200
tatacctaac cttctcaaag gcagtttagg agccatctgt tgtttctacc ctaccccaag    31260
cggcttatca agtcttcctt ccaaccatac ttcctcaggc gagtcttgat aaatatcctg    31320
gcctttatta agttatgttt ccagtgatat tttatttatt tgtttttatg tttattttta    31380 ttttttgag gtggagtctc atgctgttgc ccaggctgga gtgcaatggt gcgatctcgg    31440
ctcactgaaa ccttcgcctt tgggttcaa gtgattcttg tgcctcagcc ttccgagtag    31500
ctgggattac aggtgccttc caccatgccc agctaatttt tttttttttt gtattttag    31560 taaagatggg gtttcaccat gttggccagg ctggtctcga actcctgatc tcaggtgatc    31620
cgcctgcctc agcctcccaa agtgctggga ttataggcgt aagcctccgt gcctggcctg    31680
agtgatattt tagtgctctt tttgggtgga gctgtggtcc cagcctaact tccaggactt    31740
cagccggctc caggacacac tgtatttctg cctccttcag aaggagcaga gatagcgttg    31800
tggatgtaga gatgggtgac aggctggctc cccttgaggc ataagtctag aagaatagtg    31860
gaagaaaccc actctgtttc ccttgacatg aggctacaga gagaatttgc atttaactcc    31920
ttttccttag aagctgagaa ggtagtgtga ggctgggact tggtctagaa gcacatgggg    31980
aggtggtcta ggcttcattt agctgggccc acactgagtg gtgctgcctc taccctgctc    32040
tttgtctttc aaaaaacagt ggccagtgag ccagaaacct aagagattga gttgttgaga    32100
aaaaggctca cagcctttta aatacttacg aatttattac tacaactaag ttttttgttta    32160 ctctggtatt tgtctccagg aaagaagcca taagtcttat ctgaccaaag agatgatttt    32220
gaaacaccca tttaatatct tagtgtttat ttgtaccagt tgcactgaag taaataccac    32280
caatttacgt aaatttatct ttccatgttt ctgttatctc tcaggaaaaa acaccctccc    32340
aggccagatt taatgtattt acagcacttt ttaagtttga aaatgaatta aatatatttc    32400
tagtattttt agttatctat tgcagattat agtttgactt ttggcctttg tcccaggaca    32460
aaacctggag agaagagatt caatgaccct gaatattgtt gttttatttt tagagttctt    32520
gatatgaaac tattgtttat ccctctgggt acatgacaaa aaacagtgta agtggcaaat    32580
ttggaaatgt cctctttatt tcccagatta tctaggtcag tgttaccttta ttctacctcc    32640 tggatttact ggttcaattt ggctaaaatg gaaaaaccag tattgttcct aagggggtat    32700
gatgaaggct aatgatactg ggattcagga gatttacaga agatagaagc attgactctc    32760
tgcttctatt tcctaaaaac ttaactccca agtcttaaaa agattattac tctagcaaac    32820
ttagaaacat cacactaact catggaaata ctgatctcca tcctcctgcc tctttggaca    32880
gctcctgaag atctgtataa ggacttcctg accttggagc atctcatctg ttacagcttc    32940
caagtggcta agggcatgga gttcttggca tcgcgaaagg taagaaaggt tgaggggaaa    33000
tcagctatct tttcagatca caggtttgga aataagatgt ccagtgtcag ccattggtgc    33060
ttgtttggga ttgtaattca ttcaccactt ctacgtcttt tagaagagct ctactgggga    33120
```

```
ggctctgttt ctgctgagta agagtggtta aggagttcat gaaattaagc tgtataataa   33180
aggcttgtca agcatctact aagtgtgagg cagtcttctg agcactgagg atactgtggt   33240
gaacaatcag gcaaagctct tcaccttcat ggagtttaca gttctagtgg gtagagcaaa   33300
caataagcaa tataaacaag taaaacgtgt tgtaggttag atgagagtaa atgctatggg   33360
gaaataaagc aagaaagggt tatagaatac acaggagcaa tgcacttgtg tatgtttatg   33420
cttctctgtg tgtgtacatc tactttaaac aaggtagacg aggaaggctt tactaagaac   33480
ttgacatttg agcaatgacc tggaaagggg aggggctgag ccttacagat atcttggcat   33540
gagaatcatt tttaatttat tttacattca tcaacatcca tcaaaaagta tttgttagga   33600
gtataattag aaacgaggaa ggacaggctt cagatgagag cgattaaaag agctaaaatt   33660
agaaaagtag gccaaacaaa ggctgagatg gggacgtgac aagttacaac tattccaaag   33720
gttgtaaaca ccaagcgggg agcaaggctg gtggcagtga ttcccctgga aaggataaaa   33780
ggtgtaattt tatattaggt aacaatactt caaattaagg atcaggaaga actatcagtt   33840
gacagaatgt attcatgcag cttaatgaag aaagaaagac ttaagtcata tttttttttg   33900
tttttcctaa attagaatga aatcttcaac ccatgttttc cccttctcat agcattaaag   33960
gcctcaggct ctttgatgtt tctgctaggt agctcttatg ttctctctcc caaggggaag   34020
gaggagaact gggaccttat agggttttcc caaagagaaa ggcccttac acttcttgga    34080 gattatgact tattattacc attttttat ggccggaatt cgccacttag tcagggttcc    34140 tttgggac taggaagaga atggaaatga atgtgggaat gctttaactt tccttacatc     34200
taccagacta tttcttgaat ccacttggtt gtcgggttaa aaaaggaaac ttttgtttg    34260 gggggaaaag tcaaaaacac tgtctgtttt tggaattgc cagtgttgct caattgtgct    34320
agataatgtg cttctgaata tgccttgttc agaggagagt gccatacaga tttgaggtgt   34380
gggaaggtca gcaatgcctg gcttacatga tcacttctcc aatgatttaa gaattctcct   34440
tttggccagg tgtgttggct catgcctgta attccagcac tttgggaggc caaggtgtgt   34500
ggatcacctg aggtcaggag tttgagacca gcctggccac catggtgaaa ccccgtctct   34560
actaaaaata taataattag ctgggcgtgg tggcacacct gtggtcccaa ctacttggga   34620
ggcagaggca ggagaatcac ttgaacctgg gaggtgaagg ttgcagtgaa ctgagattgc   34680
accactgcac tccagcctgg gcgagagtga gattccttct caaaaaaaaa aaaaaaaaa    34740 aaaaaagttt tcttctaagc cattgattca tttcttgtgc tccccaagac tcattttctt   34800 acaaatatc atgtggagct aaagctgccg agtagtagga agttagctga agtttggagg    34860
atacagagaa aggagaaact gagaagctaa aaggaagaga aagaagtcaa gatgaatctc   34920
attgtactat taatgcacta gaaaatcaac ctgacttgtg ataggctgaa attgccttaa   34980 tagacctta taataaccca gcactttgaa atcagggaa gccacattgg gaattgttta    35040
tcagagccag tctggcttca gcttcatacg gaaggggaa accaacaaag agcactaaac    35100
caatgagagc cccttgtttc tgatttccgt gcattcattc aaaaaacaaa tcccgttctc   35160
ggacctcctt agaataacac gttttaaacc aaatatgggg ccaggtaaaa ggaatgtgtg   35220
gatgtgacca gaaacacact cttttgtgtc ctagaggagc ctatttatga ttccatcatc   35280
atattataac ttaattattt aactccaaag gctgggctg tttatggaat aagcagatgt     35340
gtgtctcagc aaagctcaca gacttttttc ctgaagtgtt gataaagat actaacccag     35400 tccttgttaa tcagttggct ttctgatgtg ggatttttttt ttgatgcatg aggtcacaac   35460
```

```
agatgtgaaa gagatcagct gtgccgagac ctaatgcaca catgattctc tttgcagtgt   35520
atccacaggg acctggcggc acgaaatatc ctcttatcgg agaagaacgt ggttaaaatc   35580
tgtgactttg gcttggcccg ggatatttat aaagatccag attatgtcag aaaaggagat   35640
gtaagtttca aatatgaacc cagtgcttgg ttaagtaaca gaattaaaac tcctcgtaga   35700
gagcttcagg acctgtgttc aggaacagag gaagtttttt tcttcagata tttgctaatt   35760
tgggttctga atccttgtct tctacccctg taggctcgcc tccctttgaa atggatggcc   35820
ccagaaacaa ttttttgacag agtgtacaca atccagagtg acgtctggtc ttttggtgtt   35880
ttgctgtggg aaatattttc cttaggtaag tcatttcttt ttgtccttcc atccagactc   35940
caaagaggaa gacaaaagtt gtcttttcct ctcctgtact tcatgtctat caggcaaaac   36000
ttctcggaag ctttgaaaaa aaaaatagat acataggtga tgaggatgtg caagattcag   36060
gctcagggtt ttctataaga gaaatcaaa tcaaagaatg tctcctccct gttttattct   36120
aggtgcttct ccatatcctg gggtaaagat tgatgaagaa ttttgtaggc gattgaaaga   36180
aggaactaga atgagggccc ctgattatac tacaccagaa atgtaagact ttaagaagta   36240
ttcctgtgtt ctctttcttt gctcgcaaat tctccttgcc tggaagactt tccattatat   36300
agaccttctt cattgcccag ttagtgtcct gcttttactt tggggccttt cttgataatt   36360
tcaagcatgg agtcatcact tcttgaaaag atagtacttt attattcaaa gcaaccagtt   36420 agttttttatt agatgttgct ttaaatgttt tctatacaca ttgagcctct ggagtatggg   36480
actctgtgtc ttacacagtt ttgtatcctt atttagcatc tcacctcgtc agctctttac   36540 aaaatgtgtac tcatttaagt gcttattttc agcattcagg aagaaagagg catttaatga   36600
aatcagtgtt ttgcttctct aggtaccaga ccatgctgga ctgctggcac ggggagccca   36660
gtcagagacc cacgttttca gagttggtgg aacatttggg aaatctcttg caagctaatg   36720
ctcagcaggt ttgtcacctc catccaagaa gcacctacaa agagtactta gatgtcaagg   36780
actttcctac tgcctgaact gtctcatggc taccatgcca tcctctcagc cattgaataa   36840
tctactgtat tcttctacat ctgagtaata atgcttttct aaaagctgta attaccctt   36900 tagacagata ggattctaat ttataacccg ggagcagacc actctgattt ctacctactt   36960
atctttttgt tatattttca aatcctcttc taaagttaaa acaaagaaaa aatctggttg   37020
atccacagaa gatcaacaat ggaagaaatt tcaagaaatt tttaataaat tctgcaggca   37080
aaaatacatc taagctatgc aaaagagatg gtttctgtct tggtatcatc ccaggttctt   37140
ataacttcca ctggaagatt ttagagttgt agtgtttact attagaatgt tatttaatct   37200
ctagtcaatg cctcttacta caatggaagt gaatttcctc tttcttttct tttgaacagc   37260
tgggggacga taggtcagct ctattttat caataaaccct tccaaacatt tacagatatc   37320
aaatagccct ttatttcttt tcttgatgc aataatatta agttgtgcaa ccttttctca   37380
aaagacccat tttcctaccc atttgttgct tttctttaga ctgtcatcag ttttccatt   37440 gccttgaaat gtggtggcta aaactggatg ccatgcccctt tgaagggctt ggctcgtgtg   37500
gttagggctt tgtgaatgag tgatttttttg ttctatgtag ctccttgtgt tctgttgtta   37560
cctctctgac cacagcctgc tttctcttca ttgtaactgc acttccctgt gggctgctta   37620
cccatcttgt tttagttct ctcctttaat ataccttcca tttcaacagc tttttgtttc   37680
tgacacatga tttgtattgt tgtcttaaag ttctatgttc agatatgaaa gccacacacc   37740
ctatgtagcc aagaagtccc tgtgcccttt gtttttaatg aaaaggcact tgaagaactg   37800
aagccataac aacagtcttc tgtgtttatt gtttcaggat ggcaaagact acattgttct   37860
```

```
tccgatatca gagactttga gcatggaaga ggattctgga ctctctctgc ctacctcacc   37920
tgtttcctgt atggaggagg aggaagtatg tgacccccaaa ttccattatg acaacacagc  37980
aggaatcagg tactgtatat ggcctaacat cccccggggg agggtgactt caaggccatc   38040
tcgggagggg gattggaagt ggaaggaaga ccttgtctaa ggctgttgca tcccacttcc   38100
acataacctt agccctgagg ttaacataat ggggaatgct cctggaagag ggcctgggta   38160
ggtgtgcttc ctcccatctg tagcccacgc tgctgccaca gcattgcctt taagaattcc   38220
aagccctgca gctgcaatag ctggaatgcc acagtttgct aatttccaga ataaagagac   38280
gagttttaca aagacatctg catttaaatt atccccgtgt atgctttat taatgtgaat    38340 taaatggctt aggagagatt cagaaaggaa gagttctgtg cttgcatgag aacatgctta   38400
tggctctctg gcaaggatac agaaagccat gggtctgtgt ccggaattag actgacact    38460 gcatctcaga agcccctccc acgtctgatt ttcagcattt tatttgcata atgggatgtc   38520
tgggcttatt taaaacacat gcactgcagt ccttttcctga tttgcagagg ggttctaaag  38580
gcagctttct tttttctctc tcccagcacc tgtgcataag gaaagagttg gtgtggtttt   38640
ctacaatatg atattaaaat tgccctttac taaggctggg actacttcat tttgctttgt   38700
ttctttccta acccgtttgg gtgttttcct gctttaatgg aaccctgac agcatgggtc    38760 cagcctgcca gcccgagtgt gcctgggctg caggagggg cagggagctc tctcatgtcc    38820
agaacttggc caggttgcca catggcaggg gatgctaagg agaaactcgt ggacagtttg   38880
ccctctagag tcgtgtgggg cagcagaaac actgatggga aggaagaaag cttagaagcc   38940
agcaagacag ctgaccgttc cattgaagtc aaaagcatta ggcatatttt taagaactt    39000 tgccgtatat tatcagatgt tgcccacatc atgacactca gagtcaggca aggtagaaac   39060
aatgatcttt tttttgatg tattattgaa catgaggctc agttctatta cctgagggca    39120
gtacaaactt gtagttaaag atcaggtatt agagtcagat agaaatgagt aggaccccca   39180
agtctgtctt gtagcagctg tgcaacttgg ggcaaatcat ctaccctctg cctcagtttc   39240
tttatctgtg aaatgagaca aggtcagtgg tgctgtttga aaatggctgt tttgagagtt   39300
ataagatata atctatttct aagcacctgg cccttgaaag cactcagtaa aagatcccta   39360
ttaagtgagc tgcttaaaat cacatccttg agatgaatcc agttcctctg accccctaagt  39420 ccatgttgtt tcctcccatg ccaaggaggg ccctcagaga gaaacagtaa tgagatgaga   39480
ctacaattcc actcctgtgt ttacacattt ccagttcaag ttgagctggc cttttagtgt   39540
gacagttgtt cccacacacc attattgcct cccccttat cagaaagcca tttgatcatg    39600
aactacattc catgtgtttt ctgtgaccaa gtagagtgat gatccgagtc ggcagcctcc   39660
tggctcaccg ggtgctttgc atatggtgct gagcaggaga agaaatcatg tttgtgtaat   39720
ggaagcacca aatacgatgt tggatatata aagggctgc taacgtttat ccccagaagc    39780
gtggacaaat gtgacaccac actcccagca caggcctggc tcctattttc tgtctgtgat   39840
ttttgaattg gttttccag cccagtttct ctttatcca gccataattt gaaaaataaa     39900
atggaaattg gaatcttttg tctgcatctc ctctccacct cctccacctt ttttcctttc   39960
tataaaataa aactcacggt cacattttaa tcatctggtt ttgaagaaaa gcagatagag   40020
gcatttgcac acggcatgct tcattctgtt gctctcctgg ggttctgttt ctctggggag   40080
aatgagttga ggctgggta cttctcaggg agcttgttct atcctcttac gcatttctgg    40140
ccaagtacaa aagctgagca gtctttctcc ttctaatttt caattctatt gcattataaa   40200
```

```
tagagttgga cagagatatc actgtgggag ctagcttcat gatttgttgc ccctttaaac   40260
catttgaaaa atatttactt agcatttatt tagagaaaag gctgagaagt gtgtggggga   40320
gggaccactc atgtctagac ttagctttgc ctctaatttc ccctgtggac cagctctggc   40380
ctcaagtttg catgcttcct gcaagaaaac acatacttgc tgggctcatc tttctttgag   40440
ggcagtttgg ggaccatcgg caattgctct gtcatttttcc ctgggagttt cacctcacac   40500
atcaagcagc ttatcaaaaa tttctttgca gttctctctt agagaaaggt tttggtacat   40560
accatttttct tcattttgta attgttaggg atgattaaat ggcccttgta gattgatgct   40620
tggggcagcc tgctagctag gtattcctga gtttggctct accattagac tgtttgcagt   40680
gggactgtcc tttctgcact ttttgtctgt ttcatacccc gtacttacac ccctgaccct   40740
gctactgcat gatcagtgca tgcatgacaa gagaacagtg ctgtgcacat actgggtgct   40800
taataatggc ttgaacaatt gtgtctgctg ttttcttctt tcttttccct cctgatactc   40860
ttccaaggga gtctgtatgg agtagagtaa acaaaacaa aaacttcaca tgggctttag    40920
tgtctgaagg cctaagtttg agtcccagtt ctacctttta ttagccattt tctccctaat   40980
ccttgactcc ctcatctcca aaggggaaat agttaaaaga cctgtttctc cgtcttagga   41040
gaaacagatg caccattgtc tgtgaaaatg cttttgtcaat catgagagga tcatgccatt   41100
taaaaaatta ctggattaag aatttaagga gctgtccttt ctaaggcagc tgaattattg   41160
tccaaactcg ccaaccctag ttgattctat ccctagata tctctagaat gagcccatgt    41220
ctccaaacct catgggcatt ccctttttct agccaagctg cctttctttc tcctgaagaa   41280
gtgcagtatt tgtctcttgg gtcttatgcc tctagtctta ttcttttcaa tccagagtca   41340
attctctaaa gggcatatct gatcttgtca atcccatgcc taaaatcctt cagtggctct   41400
tcattgccct caaaataata atccaaacat tccagttatg tgattttgga taagttcctc   41460
aaatttttcta tgccttggtt tcctcatctg aagagttggg atagtaatac tcacccctag   41520
agaggtaccg tggtgaacac atcatgagat gctgcttaga cagcttctgg cacagtgtca   41580
ggcttgcggc agattatcag tgagggcttc ctgaacaagt gaatgcagga atgattgact   41640
acggtaccag tagtgtttga caactgttac ttttagggggt tggacttaga aagtaggctt   41700
tgcttgcacc ctgtgtatca tatcctctta acttgtggag tttcctgagt gaggatgtca   41760
ccggaaaatc tcattctctc ctctctctat agggaggaac cagcctcttg gggtagggga   41820
gagagaatta atttccattc ttctcctttg gcccaaggtc tatgcagcat gttccagaag   41880
tctgcttgta gtgggaagta ggctggtata ggaatgaaga atgtattttc tgtctcggtg   41940
ggcccttcca gtgaatagga cttcccttcc ctccacttgg gctgtaagtg attttgatag   42000
catcaactag actcacccaa agccacacgg ccgggaagga gcattctcaa gaaggagagg   42060
atctgttgtt caacaagtct tattctttgg actcctgaag gaagctttgg aagtcaaagg   42120
agaaaaatga gctttgtttg aagagggcat tattcttcct aagagcaata agcccaacat   42180
tctctatgtc attcatcttc ccaacatccc tgtgagctgg ggaggagtg ctactgccaa    42240
cacatcttat agatgggaca agagggtcac agaaatattc atgactttct caagtttctg   42300
cagtcagtgg tagactctga aataggcaaa atatcttgtt attctcaaac cactgctctt   42360
tcctgagaca gcaactctgg gggcgaaaac gaggggacag tgagactcag cccaccttct   42420
ctttgcacac caagcctctg ttacatggag gaggaagagg ttgtcttcaa atcactgctg   42480
ggttcagtat cctttaagga gaccttcaga tgtttcctct gcctatcttt cattgaatgg   42540
ttgctctgtg agcattatcc agaaaaactt tcccaggaga tggccagaca gatgtgaaac   42600
```

```
actcagtaat atatccagag ctcgatggag gaatcccatg caatcaggaa gccaagtaga    42660
aggcagttga tcactccatc tgctgttgtt gtctttagtc cagaactgga cctcagaagt    42720
aggattcaaa agaacaggct catcgagact cctcagttat attatacttt taaatgtact    42780
ttctcaggaa attaagcctt ccatgtgtgc tagcagagaa agattttttat tttgttttgt    42840 ttttctaaag gatgttttga aggttgctat taagtttgtg gttgaaagat aatgaactta    42900
ggtagccgat ctgcagtcaa atataccacc actaaaatat aaatatttgt tcttttgcag    42960
tcagtatctg cagaacagta agcgaaagag ccggcctgtg agtgtaaaaa catttgaaga    43020
tatcccgtta aagaaccag aagtaaaagt aatcccagat gtaagtacgt cttttaaaaa    43080
tagtcttaga aataatacaa aggatgaaac actagctaga taaatattag cctaagcatt    43140
aaagttttgg agcctcatta gaaggctgcc ctcgagtgtg tgtatcatgg ggtcattatg    43200
gagatggaac tttgtttttt tcataagtaa agcccttggt ccaaggttca agacagtgta    43260
gctttctgac caatttcact aaagtgcaag tagtgtcata gtgaagacag cgatggtaac    43320
aggcattctc agctgctgat ttgtaaattt tctcttctcc ctggcctgtg tctactcata    43380
ggaagcagtt gcttcctttt gtagcttgga caatttgtgg ctatgatacc tttatgttct    43440
tccacaggac cttatttgat agacatgata gatgggttga gaaatcagct taattaaata    43500
gttggtcatt ttatatgctc aattaactgt gccatctcat tgtctcttaa aaaggacaac    43560
cagacggaca gtggtatggt tcttgcctca gaagagctga aaactttgga agacagaacc    43620
aaattatctc catcttttgg gtaagactca gccatattaa aaagacaaat ttcaatagga    43680
atttttggaa ggaacttagg actttcagtg taagtgcaga attttcccta tggggtcttt    43740
gttggttgga gaaattagca tcaatttaac aaataaagaa tggaaactaa ccacacaata    43800
aaattaagtg ataaatctaa aaataatctg aaataaatta gagaatttgg tcaatttta    43860 tgagaattca tgaatactag ggaatttctg tgtatattta ctgtggtcag taatggctaa    43920
atgaaaaagg tgattggatg tgatccgtaa agctgtcaat atgattacaa tctttgtgga    43980
ctctgaagaa ttttaagtc tgtatacaaa tgggtgcatc tgtgcttaag aagtatgata    44040
tataaataag ccaatatcta tttgtttgag acatttaaat attattgtct gaattcgaag    44100
tatttcattg tgagaaaagt attaaaatta gttttaaata taatctcct tctatggctc    44160 agtaggaatt tgtaggtgtc ttgaatacgt gtacgttctc ttaacataac aaatcaatga    44220
aaatctatat ttataagaat aatagaataa gtgtagttat gtatttgctg gagtttatt    44280 gctagagtat tcttacctaa aggtaagaat agaggaggtt ttgatctgct tataatcttt    44340
tatataaaat gggaatactc atgggttttt gaataatgct cataccaaaa agaaaacaaa    44400
caaaaaaaac cccaacatat taaaaggtgc cattgtgcta ttttattgtt ttctttaagg    44460
cccaaggtaa gaaattgtga aagtcaatga tatgtttcat tcattgattc aaaaaatgtt    44520
tattcggcaa gtatcatgtg cagagcacca tgccattgct tgagacacct acattagttt    44580
tgttggggtt gaattgaaag aaaaaattgt atttctcatt atttgaagta acttttaaac    44640
tatgtataaa cacgagttac taaaattccc ttttgcagtt ttaacatgaa gaagttgggg    44700
aaaacaccta ttaccgggaa aaaacacctt agaatggctt gtgaaagtgt aaatcctgaa    44760
gttttagatc aacacagcct gcatttctag gctttgacat gattaccgtc tgtcaggatt    44820
ccatgccatt gaaaacattt tctagttgct gctgagtgac aggggttctc agtccttcca    44880
aggaatgtgg ttttgatgag taaaaagcag cgtttgatat gtctggcttg actgcacaca    44940
```

```
tgcttcaagt tattaaagtt taaagttgct caagagcttt attacaacca tacacatgcc    45000
ccgtaattcc caaattgcca caataggaaa agcacaagtg aaatttaaga acatcccaat    45060
ttccttgaat atcatgcaag tggccctttg gcgcctgtca ctgtatacaa atttgtcaat    45120
ctgcgaggcc ataaacatgt tccatcagtt ggggcctttg cataactcga gagaactgcc    45180
tttcatctca tttgaggctt gaaagacttg gacctgagta agaggactta tctgcaacta    45240
ctaattcatg cgagtacctg aaaatagacc ttgtccctgt aaacctgcta tgctgattaa    45300
caactgggag agatacgggg ctgcggtctc cagggagatg gcagccatat ggagttggga    45360
atggggtgag ggtaaaaagc aaagaattg tcttctctct gccaactcct ttgtttgcca     45420
tttcttctgc agtggaatgg tgcccagcaa aagcagggag tctgtggcat ctgaaggctc    45480
aaaccagaca agcggctacc agtccggata tcactccgat gacacagaca ccaccgtgta    45540
ctccagtgag gaagcagaac ttttaaagct gatagagatt ggagtgcaaa ccggtagcac    45600
agcccagatt ctccagcctg actcggggac cacactgagc tctcctcctg tttaaaagga    45660
agcatccaca cccccaactc ctggacatca catgagaggt gctgctcaga ttttcaagtg    45720
ttgttctttc caccagcagg aagtagccgc atttgatttt catttcgaca acagaaaaag    45780
gacctcggac tgcagggagc cagtcttcta ggcatatcct ggaagaggct tgtgacccaa    45840
gaatgtgtct gtgtcttctc ccagtgttga cctgatcctc tttttcattc atttaaaaag    45900
catttatcat gcccctgct gcgggtctca ccatgggttt agaacaaaga cgttcaagaa      45960
atggccccat cctcaaagaa gtagcagtac ctggggagct gacacttctg taaaactaga    46020
agataaacca ggcaatgtaa gtgttcgagg tgttgaagat gggaaggatt tgcagggctg    46080
agtctatcca agaggctttg tttaggacgt gggtcccaag ccaagcctta agtgtggaat    46140
tcggattgat agaaaggaag actaacgtta ccttgctttg gagagtactg gagcctgcaa    46200
atgcattgtg tttgctctgg tggaggtggg catgggtct gttctgaaat gtaaagggtt      46260
cagacggggt ttctggtttt agaaggttgc gtgttcttcg agttgggcta aagtagagtt    46320
cgttgtgctg tttctgactc ctaatgagag ttccttccag accgttacgt gtctcctggc    46380
caagccccag gaaggaaatg atgcagctct ggctccttgt ctcccaggct gatcctttat    46440
tcagaatacc acaaagaaag gacattcagc tcaaggctcc ctgccgtgtt aagagttct     46500 gactgcacaa accagcttct ggtttcttct ggaatgaata ccctcatatc tgtcctgatg    46560
tgatatgtct gagactgaat gcgggaggtt caatgtgaag ctgtgtgtgg tgtcaaagtt    46620
tcaggaagga ttttaccctt ttgttcttcc ccctgtcccc aacccactct caccccgcaa    46680
cccatcagta ttttagttat ttggcctcta ctccagtaaa cctgattggg tttgttcact    46740
ctctgaatga ttattagcca gacttcaaaa ttattttata gcccaaatta taacatctat    46800
tgtattattt agactttaa catatagagc tatttctact gattttgcc cttgttctgt       46860 cctttttttc aaaaagaaa atgtgttttt tgtttggtac catagtgtga aatgctggga     46920
acaatgacta taagacatgc tatggcacat atatttatag tctgtttatg tagaaacaaa    46980
tgtaatatat taaagcctta tatataatga actttgtact attcacattt tgtatcagta    47040
ttatgtagca taacaaggt cataatgctt tcagcaattg atgtcatttt attaaagaac      47100
attgaaaaac ttgaaggaat ccctttgcaa ggttgcatta ctgtacccat catttctaaa    47160
atggaagagg gggtggctgg gcacagtggc cgacacctaa aaacccagca ctttgggggg    47220
ccaaggtggg aggatcgctt gagcccagga gttcaagacc agtctggcca acatggtcag    47280
attccatctc aaagaaaaaa ggtaaaaata aaataaaatg gagaagaagg aatcaga       47337
```

<210> SEQ ID NO 13
<211> LENGTH: 1033
<212> TYPE: DNA
<213> ORGANISM: Homo sapiens

<400> SEQUENCE: 13

```
agactgaccc cattctctgt ctgtgcctgg gttgctgggg actattatgg gatgcatttc    60
ctgaggctct gggcctcaag ttggccctga atcagctgag tcaagatcaa gtctaggttg   120
aaaactgagt gagggccagg tgcggtggct caggcctgta atcccagcac tttgggaggc   180
caaggcaggc agatcacctg aggtcaggag ttcaagacca gcctagacaa catggtgaaa   240
ccccatctct attaaaaata caaaattagc tgggtgtggt gacgcgatcc tgtaatgtca   300
gctactctgg aggctgaggc aggagaattg cttgaatctg ggaggcagag gttgcagtga   360
accaaaaatt gtgccacagc actccagcct gggcgacaag agtgagactc catctcaaaa   420
aaaaaaagaa aaagaaaaag aaaagaaaac tgagtgggat gtgaaggttt atgcagaatt   480
gcaccaggca tttagcagga gaagctcaaa ttgccctcca ggcttcctta gaaaagccca   540
agtcactgtc cccttttgct atggtaactg caagtcctgg acaggtcctg gcctttggat   600
gcttgtctcc caggcatgac tccaacaatg catcccatgg gatttggggt tccccagatc   660
tggggcttgt aggcctgact ctcccctgtg cacacgtctc atacacgcat gcgtgcaccc   720
attgcctgcc ccgccccttg cacagggagt cagcagggag gactgggtta tgccctgctt   780
atcagcagct tccagcttc ctctgcctgg attcttagag gcctgggtc ctagaacgag    840
ctggtgcacg tggcttccca aagatctctc agataatgag aggaaatgca gtcatcagtt   900
tgcagaaggc tagggattct gggccatagc tcagacctgc gcccaccatc tccctccagg   960
cagcccttgg ctggtccctg cgagcccgtg gagactgcca gagatgtcct ctttcggtta  1020
caggaccctg act                                                     1033
```

<210> SEQ ID NO 14
<211> LENGTH: 20
<212> TYPE: DNA
<213> ORGANISM: Artificial Sequence
<220> FEATURE:
<223> OTHER INFORMATION: guide sequence

<400> SEQUENCE: 14

```
ttcccggtag aagcacttgt                                                 20
```

<210> SEQ ID NO 15
<211> LENGTH: 1368
<212> TYPE: PRT
<213> ORGANISM: Streptococcus pyogenes

<400> SEQUENCE: 15

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80
```

```
Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495
```

```
Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910
```

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

```
Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
    1355                1360                1365

<210> SEQ ID NO 16
<211> LENGTH: 1053
<212> TYPE: PRT
<213> ORGANISM: Staphylococcus aureus

<400> SEQUENCE: 16

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg His Arg Ile
50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
290                 295                 300

Val Asn Glu Glu Asp Ile Lys Gly Tyr Arg Val Thr Ser Thr Gly Lys
305                 310                 315                 320
```

```
Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
                340                 345                 350

Lys Ile Leu Thr Ile Tyr Gln Ser Ser Glu Asp Ile Gln Glu Glu Leu
                355                 360                 365

Thr Asn Leu Asn Ser Glu Leu Thr Gln Glu Glu Ile Glu Gln Ile Ser
        370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
                420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
        450                 455                 460

Ile Lys Lys Tyr Gly Leu Pro Asn Asp Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
                500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
                580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
        610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
        690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735
```

Gln Ala Glu Ser Met Pro Glu Ile Glu Thr Gln Glu Tyr Lys Glu
                740                 745                 750

Ile Phe Ile Thr Pro His Gln Ile Lys His Ile Lys Asp Phe Lys Asp
            755                 760                 765

Tyr Lys Tyr Ser His Arg Val Asp Lys Lys Pro Asn Arg Glu Leu Ile
        770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
            885                 890                 895

Tyr Pro Asn Ser Arg Asn Lys Val Val Lys Leu Ser Leu Lys Pro Tyr
        900                 905                 910

Arg Phe Asp Val Tyr Leu Asp Asn Gly Val Tyr Lys Phe Val Thr Val
            915                 920                 925

Lys Asn Leu Asp Val Ile Lys Lys Glu Asn Tyr Tyr Glu Val Asn Ser
930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
            965                 970                 975

Glu Leu Tyr Arg Val Ile Gly Val Asn Asn Asp Leu Leu Asn Arg Ile
        980                 985                 990

Glu Val Asn Met Ile Asp Ile Thr Tyr Arg Glu Tyr Leu Glu Asn Met
        995                 1000                1005

Asn Asp Lys Arg Pro Pro Arg Ile Ile Lys Thr Ile Ala Ser Lys
        1010                1015                1020

Thr Gln Ser Ile Lys Lys Tyr Ser Thr Asp Ile Leu Gly Asn Leu
        1025                1030                1035

Tyr Glu Val Lys Ser Lys Lys His Pro Gln Ile Ile Lys Lys Gly
        1040                1045                1050

<210> SEQ ID NO 17
<211> LENGTH: 39
<212> TYPE: DNA
<213> ORGANISM: Artificial Sequence
<220> FEATURE:
<223> OTHER INFORMATION: mouse VEGFR2-targeted locus

<400> SEQUENCE: 17
tgtcgacgtc ccggtacgag cacttgtagg ctccagtat                    39

<210> SEQ ID NO 18
<211> LENGTH: 23
<212> TYPE: DNA
<213> ORGANISM: Artificial Sequence
<220> FEATURE:
<223> OTHER INFORMATION: neuron-specific promoter

```
<400> SEQUENCE: 18
aacgtcccgg tacgagcact tgt                                              23

<210> SEQ ID NO 19
<211> LENGTH: 23
<212> TYPE: DNA
<213> ORGANISM: Artificial Sequence
<220> FEATURE:
<223> OTHER INFORMATION: neuron-specific promoter

<400> SEQUENCE: 19
aacacaagtg ctcgtacctt tac                                              23

<210> SEQ ID NO 20
<211> LENGTH: 31
<212> TYPE: DNA
<213> ORGANISM: Artificial Sequence
<220> FEATURE:
<223> OTHER INFORMATION: rAAV1-lacZ

<400> SEQUENCE: 20
tgtcgacgtc ccggtacgag cacttgtagg c                                     31

<210> SEQ ID NO 21
<211> LENGTH: 31
<212> TYPE: DNA
<213> ORGANISM: Artificial Sequence
<220> FEATURE:
<223> OTHER INFORMATION: rAAV1-mK22
<220> FEATURE:
<221> NAME/KEY: misc_feature
<222> LOCATION: (25)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t

<400> SEQUENCE: 21
tgtcgacgtc ccggtacgag cactnnnngn n                                     31

<210> SEQ ID NO 22
<211> LENGTH: 28
<212> TYPE: DNA
<213> ORGANISM: Artificial Sequence
<220> FEATURE:
<223> OTHER INFORMATION: fragment

<400> SEQUENCE: 22
tgtcccggta cgagcacttg taggctcc                                         28

<210> SEQ ID NO 23
<211> LENGTH: 27
<212> TYPE: DNA
<213> ORGANISM: Artificial Sequence
<220> FEATURE:
<223> OTHER INFORMATION: fragment

<400> SEQUENCE: 23
tgtcccggta cgagcactgt aggctcc                                          27

<210> SEQ ID NO 24
<211> LENGTH: 29
<212> TYPE: DNA
<213> ORGANISM: Artificial Sequence
<220> FEATURE:
```

```
<223> OTHER INFORMATION: fragment

<400> SEQUENCE: 24
tgtcccggta cgagcacttt gtaggctcc                                    29
```